(12) United States Patent
Pinto et al.

(10) Patent No.: US 6,960,595 B2
(45) Date of Patent: Nov. 1, 2005

(54) 5-6 TO 5-7 HETEROBICYCLES AS FACTOR XA INHIBITORS

(75) Inventors: Donald Joseph Philip Pinto, Kennett Square, PA (US); Renhua Li, Noblesville, IN (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/105,477

(22) Filed: Mar. 25, 2002

(65) Prior Publication Data

US 2003/0018023 A1 Jan. 23, 2003

Related U.S. Application Data

(60) Provisional application No. 60/278,165, filed on Mar. 23, 2001.

(51) Int. Cl.[7] .................. C07D 487/04; C07D 401/04; C07D 401/10; A61K 31/55
(52) U.S. Cl. .................. 514/275; 514/303; 544/330; 544/331; 544/332; 546/119
(58) Field of Search .................. 546/119; 514/303, 514/275; 544/330, 331, 332

(56) References Cited

U.S. PATENT DOCUMENTS 6,506,771 B2 * 1/2003 Pinto et al. .................. 514/303

FOREIGN PATENT DOCUMENTS

| WO | WO 95/01980 | * | 1/1995 |
| WO | WO 00/39131 | * | 7/2000 |
| WO | WO 02/00655 | * | 1/2002 |

* cited by examiner

*Primary Examiner*—Deepak Rao
(74) *Attorney, Agent, or Firm*—Jing G. Sun; David H. Vance

(57) ABSTRACT

The present application describes 5–6 or 5–7 heterobicyclics of Formula I:

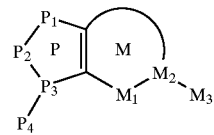

or pharmaceutically acceptable salt forms thereof, wherein ring P is a 5-membered heteroaromatic and ring M is a 6 or 7-membered non-aromatic carbocycle or heterocycle. Compounds of the present invention are useful as inhibitors of trypsin-like serine proteases, specifically factor Xa.

35 Claims, No Drawings

5-6 TO 5-7 HETEROBICYCLES AS FACTOR Xa INHIBITORS

FIELD OF THE INVENTION

This invention relates generally to 5–6 or 5–7 heterobicycles, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO94/20460 describes angiotensin II compounds of the following formula:

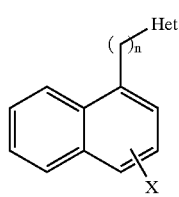

wherein X can be a number of substituents and Het can be a nitrogen-containing heterobicycle. However, WO94/20460 does not suggest Factor Xa inhibition or exemplify compounds like those of the present invention.

WO96/12720 depicts phosphodiesterase type IV and TNF production inhibitors of the following formula:

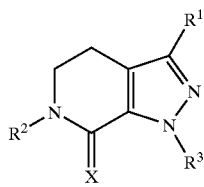

wherein X can be oxygen and $R^2$ and $R^3$ can a number of substituents including heterocycle, heterocycloalkyl, and phenyl. However, the presently claimed compounds do not correspond to the compounds of WO96/12720. Furthermore, WO96/12720 does not suggest Factor Xa inhibition.

WO98/52948 details inhibitors of ceramide-mediated signal transduction. One of the types of inhibitors described is of the following formula:

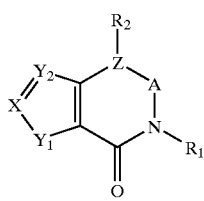

wherein $Y_1$ can be N—$R_6$, $R_6$ can be unsubstituted arylalkyl or unsubstituted heterocyclic-alkyl and $R_1$ can be a substituted aryl group. WO98/52948 does not mention factor Xa inhibition or show compounds like those of the present invention.

U.S. Pat. Nos. 3,365,459, 3,340,269, and 3,423,414 illustrate anti-inflammatory inhibitors of the following formula:

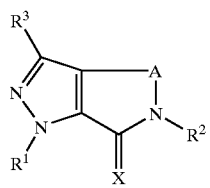

wherein A is 2–3 carbon atoms, X can be O, and $R^1$ and $R^3$ can be substituted or unsubstituted aromatic groups. None of these patents, however, exemplify or suggest compounds of the present invention.

WO99/32477 reports Factor Xa inhibitors of the following formula:

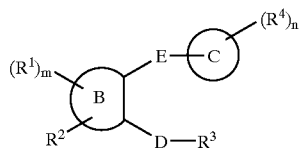

wherein the inhibitors contain at least three aryl or heterocyclic groups (i.e., C, B, and $R^3$) separated by two linking groups (i.e., E and D). Compounds of this sort are not considered to be part of the present invention.

WO00/39131 describes heterobicyclic Factor Xa inhibitors of which the following is an example formula:

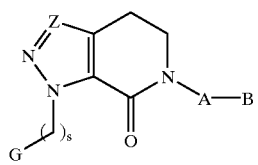

wherein Z is C or N, G is a mono- or bicyclic group, A is a cyclic moiety and B is a basic group or a cyclic moiety. Compounds with this substitution pattern are not considered to be part of the present invention.

WO01/19798 describes factor Xa inhibitors of the following formula:

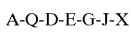

A-Q-D-E-G-J-X wherein A, D, G, and X can be phenyl or heterocycle. However, none of the presently claimed compounds are exemplified or suggested in WO01/19798.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel heterobicycles that are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide a novel method of treating a patient in need of thromboembolic disorder treatment, comprising: administering a compound of the present invention or a pharmaceutically acceptable salt form thereof in an amount effective to treat a thromboembolic disorder It is another object of the present invention to provide a novel method, comprising: administering a compound of the present invention or a pharmaceutically acceptable salt form thereof in an amount effective to treat a thromboembolic disorder.

It is another object of the present invention to provide novel compounds for use in therapy.

It is another object of the present invention to provide the use of novel compounds for the manufacture of a medicament for the treatment of a thromboembolic disorder.

These and other objects, which will become apparent during the following detailed description, have been achieved by the inventors' discovery that the presently claimed bicyclic compounds, or pharmaceutically acceptable salt or prodrug forms thereof, are effective factor Xa inhibitors.

DETAILED DESCRIPTION OF PREFERRED EMBODIMENTS

[1] Thus, in an embodiment, the present invention provides a novel compound of formula I:

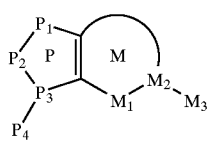

I or a stereoisomer or pharmaceutically acceptable salt thereof, wherein;
ring M, including $M_1$ and $M_2$, is a 6 or 7 membered carbocycle or 6 or 7 membered heterocycle, consisting of: carbon atoms and 0–3 heteroatoms selected from 0, $S(O)_p$, N, and $NZ^2$;
ring M is substituted with 0–2 $R^{1a}$ and 0–2 carbonyl groups, and, comprises: 0–2 double bonds;

alternatively, $M_1$ is C(O) or $CH_2$, $M_2$ is N, and the bridging portion of ring M is $S(O)_2$;
ring P, including $P_1$, $P_2$, $P_3$, and $P_4$ is selected from group:

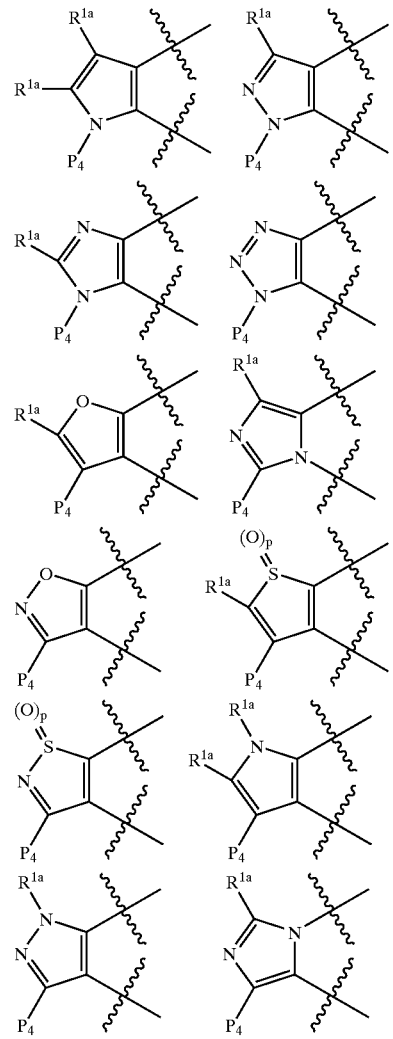

one of $P_4$ and $M_3$ is -Z-A-B and the other -$G_1$-G;
G is a group of formula IIa or IIb:

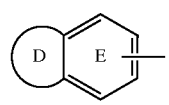

IIa

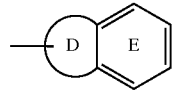

IIb ring D, including the two atoms of Ring E to which it is attached, is a 5–6 membered non-aromatic ring consisting of carbon atoms, 0–1 double bonds, and 0–2 heteroatoms selected from the group consisting of N, O, and $S(O)_p$, and D is substituted with 0–2 R;
alternatively, ring D, including the two atoms of Ring E to which it is attached, is a 5–6 membered aromatic system consisting of carbon atoms and 0–2 heteroatoms selected from the group consisting of N, O, and $S(O)_p$, and D is substituted with 0–2 R;

E is selected from phenyl, pyridyl, pyrimidyl, pyrazinyl, and pyridazinyl, and is substituted with 1–2 R;

alternatively, the bridging portion of ring D is absent, and ring E is selected from phenyl, pyridyl, pyrimidyl, pyrazinyl, pyridazinyl, pyrrolyl, imidazolyl, pyrazolyl, isoxazolyl, oxazolyl, triazolyl, thienyl, and thiazolyl, and ring E is substituted with 1–2 R;

alternatively, the bridging portion of ring D is absent, ring E is selected from phenyl, phenyl, pyridyl, pyrimidyl, pyrazinyl, pyridazinyl, pyrrolyl, imidazolyl, pyrazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the heterocycle is substituted with 0–1 carbonyls, 1–2 R, and having 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_rC(O)H$, $(CR^8R^9)_rC(O)R^{2c}$, $(CR^8R^9)_rNR^7R^8$, $(CR^8R^9)_tC(O)NR^7R^8$, $(CR^8R^9)_rNR^7C(O)R^7$, $(CR^8R^9)_r OR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$, provided that $S(O)_pR^7$ forms other than $S(O)_2H$ or $S(O)H$;

alternatively, when 2 R groups are attached to adjacent atoms, they combine to form methylenedioxy or ethylenedioxy;

A is selected from:
  $C_{3-10}$ carbocycle substituted with 0–2 $R^4$, and
  5–12 membered heterocycle consisting of: carbon atoms and 1–4 heteroatoms selected from the group consisting of N, O, and $S(O)_p$ substituted with 0–2 $R^4$;

B is selected from: Y, X—Y, $(CH_2)_{0-2}C(O)NR^2R^{2a}$, $(CH_2)_{0-2}NR^2R^{2a}$, $C(=NR^2)NR^2R^{2a}$, and $NR^2C(=NR^2)NR^2R^{2a}$, provided that Z and B are attached to different atoms on A;

$G_1$ is absent or is selected from $(CR^3R^{3a})_{1-5}$, $(CR^3R^{3a})_{0-2}CR^3=CR^3(CR^3R^{3a})_{0-2}$, $(CR^3R^{3a})_{0-2}$, $C\equiv C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uO(CR^3R^{3a})_w$, $(CR^3R^{3a})_uNR^3(CR^3R^{3a})_w$, $(CR^3R^{3a})_uC(O)$ $NR^3$ $(CR^3R^{3a})_w$, $(CR^3R^{3a})_u$ $NR^3C(O)$ $(CR^3R^{3a})_w$, $(CR^3R^{3a})_uOC(O)NR^3(CR^3R^{3a})_w$, $(CR^3R^{3a})_u NR^3C(O)O(CR^3R^{3a})_w$, $(CR^3R^{3a})_uNR^3C(O)NR^3(CR^3R^{3a})_w$, $(CR^3R^{3a})_uNR^3C(S)NR^3(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^3(CR^3R^{3a})_w$, $(CR^3R^{3a})_uNR^3S(O)_2(CR^3R^{3a})_w$, $(CR^3R^{3a})_uS(O)_2NR^3(CR^3R^{3a})_w$, and $(CR^3R^{3a})_uNR^3S(O)_2NR^3(CR^3R^{3a})_w$, wherein u+w total 0, 1, 2, 3, or 4, provided that $G_1$ does not form a N—N, N—O, N—S, $NCH_2N$, $NCH_2O$, or $NCH_2S$ bond with either group to which it is attached;

X is selected from $-(CR^2R^{2a})_{1-4}-$, $-CR^2(CR^2R^{2b})(CH_2)_t-$, $-C(O)-$, $-C(=NR^{1c})-$, $-CR^2(NR^{1c}R^2)-$, $-CR^2(OR^2)-$, $-CR^2(SR^2)-$, $-C(O)CR^2R^{2a}-$, $-CR^2R^{2a}C(O)$, $-S-$, $-S(O)-$, $-S(O)_2-$, $-SCR^2R^{2a}-$, $-S(O)CR^2R^{2a}-$, $-(O)_2CR^2R^{2a}-$, $-CR^2R^{2a}S-$, $-CR^2R^{2a}S(O)-$, $-CR^2R^{2a}S(O)_2-$, $-S(O)_2NR^2-$, $-NR^2S(O)_2-$, $-NR^2S(O)_2NR^2-$, $-CR^2R^{2a}S(O)_2NR^2-$, $-NR^2S(O)_2CR^2R^{2a}-$, $-NR^2S(O)_2NR^2-$, $-C(O)NR^2-$, $-NR^2C(O)-$, $-C(O)NR^2CR^2R^{2a}-$, $-NR^2C(O)_2CR^2R^{2a}-$, $-CR^2R^{2a}C(O)NR^2-$, $-CR^2R^{2a}NR^2C(O)-$, $-NR^2C(O)O-$, $-OC$ $(O)NR^2-$, $-NR^2C(O)NR^2-$, $-NR^2-$, $-NR^2CR^2R^{2a}-$, $-CR^2R^{2a}NR^2-$, O, $-CR^2R^{2a}O-$, and $-OCR^2R^{2a}-$;

Y is selected from:
  $C_{3-10}$ carbocycle substituted with 0–2 $R^{4a}$, and,
  5–10 membered heterocycle consisting of: carbon atoms and 1–4 heteroatoms selected from the group consisting of N, O, and $S(O)_p$ substituted with 0–2 $R^{4a}$;

Z is selected from $-(CR^2R^{2a})_{1-4}-$, $(CR^2R^{2a})_qO(CR^2R^{2a})_{q1}$, $(CR^2R^{2a})_qNR^3(CR^2R^{2a})_{q1}$, $(CR^2R^{2a})_qC(O)(CR^2R^{2a})_{q1}$, $(CR^2R^{2a})_qC(O)O(CR^2R^{2a})_{q1}$, $(CR^2R^{2a})_qOC(O)(CR^2R^{2a})_{q1}$, $(CR^2R^{2a})_qC(O)NR^3(CR^2R^{2a})_{q1}$, $(CH_2)_q NR^3C(O)(CR^2R^{2a})_{q1}$, $(CR^2R^{2a})_qOC(O)O(CR^2R^{2a})_{q1}$, $(CH_2)_qOC(O)NR^3(CR^2R^{2a})_{q1}$, $(CR^2R^{2a})_qNR^3C(O)O(CR^2R^{2a})_{q1}$, $(CH_2)_qNR^3C(O)NR^3(CR^2R^{2a})_{q1}$, $(CR^2R^{2a})_q S(CR^2R^{2a})_{q1}$, $(CR^2R^{2a})_qS(O)(CR^2R^{2a})_{q1}$, $(CH_2)_qS(O)_2(CR^2R^{2a})_{q1}$, $(CR^2R^{2a})_qSO_2NR^3(CR^2R^{2a})_{q1}$, $(CH_2)_qNR^3SO_2(CR^2R^{2a})_{q1}$, and $(CR^2R^{2a})_q NR^3SO_2NR^3(CR^2R^{2a})_{q1}$, wherein q+q1 total 0, 1, or 2, provided that Z does not form a N—N, N—O, N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^3$, and $S(O)_pR^{3c}$;

$R^{1a}$ is selected from H, $-(CH_2)_r-R^{1b}$, $-CH=CH-R^{1b}$, $NCH_2R^{1c}$, $OCH_2R^{1c}$, $SCH_2R^{1c}$, $NH(CH_2)_2(CH_2)_rR^{1b}$, $O(CH_2)_2(CH_2)_rR^{1b}$, $S(CH_2)_2(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—N, N—S, N—O, or N—CN bond;

alternatively, when two $R^{1a}$'s are attached to adjacent atoms, together with the atoms to which they are attached, they form a 5–7 membered ring consisting of: carbon atoms and 0–2 heteroatoms selected from the group consisting of N, O, and $S(O)_p$, this ring being substituted with 0–2 $R^{4b}$ and comprising: 0–3 double bonds;

$R^{1b}$ is selected from H, $C_{1-3}$ alkyl, F, Cl, Br, I, $-CN$, $-CHO$, $(CF_2)_rCF_3$, $(CH_2)_rOR^2$, $NR^{2a}$, $C(O)R^{2c}$, $OC(O)R^2$, $(CF_2)_rCO_2R^{2a}$, $S(O)_pR^{2b}$, $NR^2(CH_2)_rOR^2$, $C(=NR^2C)NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocycle substituted with 0–2 $R^{4a}$, and 5–10 membered heterocycle consisting of carbon atoms and from 1–4 heteroatoms selected from the group consisting of N, O, and $S(O)_p$ substituted with 0–2 $R^{4a}$, provided that $R^{1b}$ forms other than an N-halo, N—N, N—S, N—O, or N—CN bond;

$R^{1c}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^{1d}$ is selected from $C_{3-6}$ carbocycle substituted with 0–2 $R^{4a}$ and 5–10 membered heterocycle consisting of carbon atoms and from 1–4 heteroatoms selected from the group consisting of N, O, and $S(O)_p$ substituted with 0–2 $R^{4a}$, provided that $R^{1d}$ forms other than an N—N, N—S, or N—O bond;

$R^2$, at each occurrence, is selected from H, $CF_3$, $C_{1-6}$ alkyl, benzyl, $C_{3-6}$ carbocycle substituted with 0–2 $R^{4b}$, a $C_{3-6}$ carbocycle-$CH_2-$ substituted with 0–2 $R^{4b}$, and 5–6 membered heterocycle consisting of: carbon atoms and 1–4 heteroatoms selected from the group consisting of N, O, and $S(O)_p$ substituted with 0–2 $R^{4b}$;

$R^{2a}$, at each occurrence, is selected from H, $CF_3$, $C_{1-6}$ alkyl, benzyl, $C_{3-6}$ carbocycle substituted with 0–2 $R^{4b}$, and 5–6 membered heterocycle consisting of: carbon atoms and 1–4 heteroatoms selected from the group consisting of N, O, and $S(O)_p$ substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocycle substituted with 0–2

$R^{4b}$, and 5–6 membered heterocycle consisting of: carbon atoms and 1–4 heteroatoms selected from the group consisting of N, O, and $S(O)_p$ substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocycle substituted with 0–2 $R^{4b}$, and 5–6 membered heterocyclic system containing from 1–4 heteroatoms selected from the group consisting of N, O, and $S(O)_p$ substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^3$, at each occurrence, is selected from H, $C_{1-4}$ alkyl, and phenyl;

$R^{3a}$, at each occurrence, is selected from H, $C_{1-4}$ alkyl, benzyl, and phenyl;

$R^{3b}$, at each occurrence, is selected from H, $C_{1-4}$ alkyl, and phenyl;

$R^{3c}$, at each occurrence, is selected from $C_{1-4}$ alkyl, benzyl, and phenyl;

$R^{3d}$, at each occurrence, is selected from H, $C_{1-4}$ alkyl, $C_{1-4}$ alkyl-phenyl, and $C(=O)R^{3c}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $C(=NR^2)NR^2R^{2a}$, $C(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1c}$, $OCH_2R^{1c}$, $SCH_2R^{1c}$, $N(CH_2)_2(CH_2)_tR^{1b}$, $O(CH_2)_2(CH_2)_tR^{1b}$, and $S(CH_2)_2(CH_2)_tR^{1b}$;

alternatively, one $R^4$ is a 5–6 membered aromatic heterocycle consisting of: carbon atoms and 1–4 heteroatoms selected from the group consisting of N, O, and $S(O)_p$;

$R^{4a}$, at each occurrence, is selected from H, =O, $(CH_2)_rOR^2$, $(CH_2)_r$—F, $(CH_2)_r$—Br, $(CH_2)_r$—Cl, Cl, Br, F, I, $C_{1-4}$ alkyl, s-CN, $NO_2$, $(CH_2)_rNR^2R^{2a}$, $(CH_2)_rC(O)R^{2c}$, $NR^2C(O)R^{2b}$, $C(O)NR^2R^{2a}$, $(CH_2)_rN=CHOR^3$, $C(O)NH(CH_2)_2NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $C(O)NHSO_2$—$C_{1-4}$ alkyl, $NR^2SO_2R^5$, $S(O)_pR^5$, and $(CF_2)_rCF_3$;

alternatively, one $R^{4a}$ is phenyl substituted with 0–1 $R^5$ or a 5–6 membered aromatic heterocycle consisting of:
carbon atoms and 1–4 heteroatoms selected from the group consisting of N, O, and $S(O)_p$ substituted with 0–1 $R^5$;

$R^{4b}$, at each occurrence, is selected from H, =O, $(CH_2)_rOR^3$, F, Cl, Br, I, $C_{1-4}$ alkyl, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from H, $C_{1-6}$ alkyl, =O, $(CH_2)_rOR^3$, F, Cl, Br, I, $C_{1-4}$ alkyl, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR_2R^{2a}$, $(CH_2)_rC(O)$ $R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl, and $(CH_2)_n$-phenyl;

alternatively, $R^7$ and $R^8$ combine to form a 5 or 6 membered saturated, ring which contains from 0–1 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;
p, at each occurrence, is selected from 0, 1, and 2;
r, at each occurrence, is selected from 0, 1, 2, 3, 4, 5, and 6;
t, at each occurrence, is selected from 0, 1, 2, and 3;
provided that:

(a) when $P_4$ is -Z-A-B, $M_1$ is a carbonyl, and G is substituted with an amidino, guanidino, amino-ethylene, or amino-propylene group, any of which may be substituted or cyclized, then $G_1$ is present or Z is other than a bond or alkylene; and (b) when $P_4$ is -$G_1$-G, M1 is a carbonyl, and $G_1$ is absent or alkylene, then Z is other than a bond or alkylene;

alternatively, when (a) B is other than an optionally substituted carbocycle; and, (b) $G_1$ is $(CR^3R^{3a})_uNR^3(CR^3R^{3a})_w$ and u+w is 1, 2, 3, or 4, $(CR^3R^{3a})_uC(O)NR^3(CR^3R^{3a})_w$, $(CR^3R^{3a})$ $NR^3C(O)$ $(CR^3R^{3a})_w$, $(CR^3R^{3a})_uS(O)NR^3(CR^3R^{3a})_w$, $(CR^3R^{3a})_u$ $S(O)_2NR^3(CR^3R^3a)_w$, or $(CR^3R^{3a})_uNR^3S(O)_2$ $(CR^3R^{3a})_w$;

then Z is other than $(CH_2)NR^3$, $NR^3(CH_2)$, $(CH_2)NR^3$ $(CH_2)$, $(CH_2)(CH_2)NR^3$, $NR^3(CH_2)(CH_2)$, $(CH_2)_qC(O)NR^3(CH_2)_{q1}$, $(CH_2)_qNR^3C(O)(CH_2)_{q1}$, $(CH_2)_q$ $SO_2NR^3(CH_2)_{q1}$, or $(CH_2)_qNR^3SO_2(CH_2)_{q1}$;

alternatively, when (a) B is other than an optionally substituted carbocycle; and, (b) Z is $(CH_2)NR^3$, $NR^3(CH_2)$, $(CH_2)NR^3(CH_2)$, $(CH_2)$ $(CH_2)NR^3$, $NR^3(CH_2)(CH_2)$, $(CH_2)_qC(O)NR^3(CH_2)_{q1}$, $(CH_2)_qNR^3C(O)(CH_2)_{q1}$, $(CH_2)_qSO_2NR^3(CH_2)_{q1}$, or $(CH_2)_qNR^3SO_2(CH_2)_{q1}$;

then $G_1$ is other than $(CR^3R^{3a})_uNR^3(CR^3R^{3a})_w$ and u+w is 1, 2, 3, or 4, $(CR^3R^{3a})_uC(O)$ $NR^3(CR^3R^{3a})_w$, $(CR^3R^{3a})_uNR^3C(O)(CR^3R^{3a})_w$, $(CR^3R^{3a})_uS(O)NR^3$ $(CR^3R^{3a})_w$, $(CR^3R^{3a})_uS(O)_2NR^3(CR^3R^{3a})_w$, or $(CR^3R^{3a})_uNR^3S(O)_2(CR^3R^{3a})_w$.

[2] In a preferred embodiment, the present invention provides a novel compound, wherein:

ring M is substituted with 0–2 $R^{1a}$ and is selected from the group:

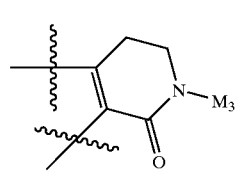 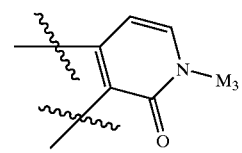

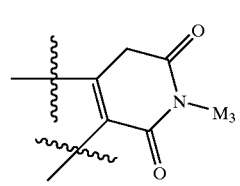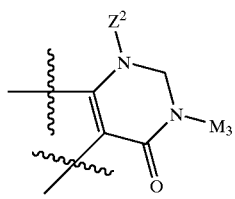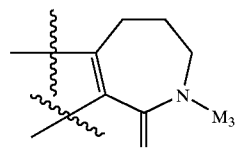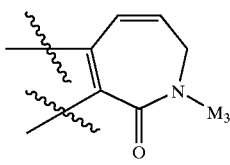
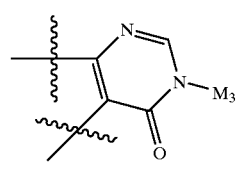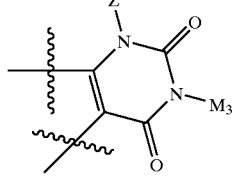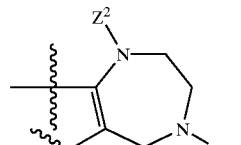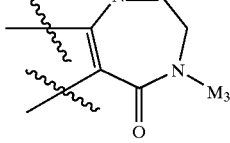
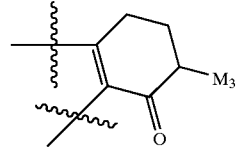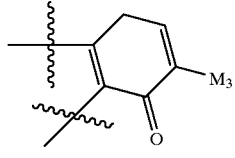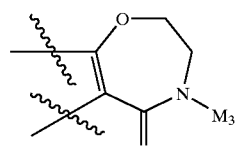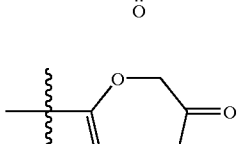
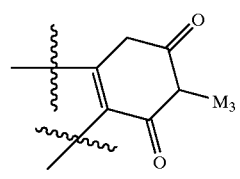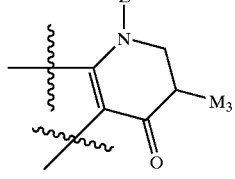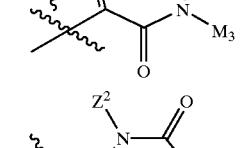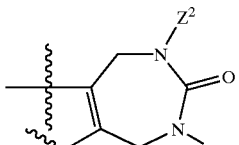
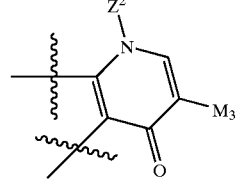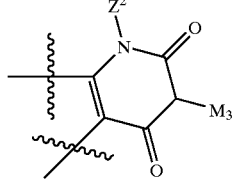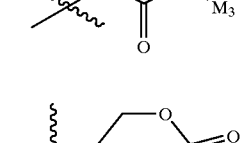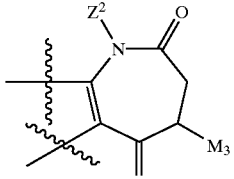
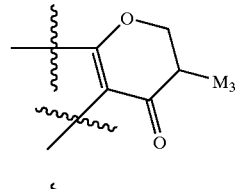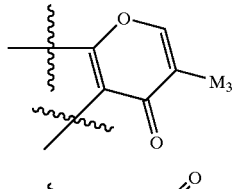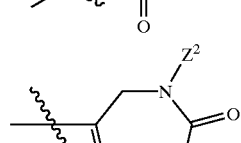
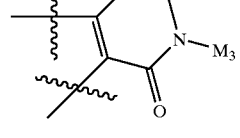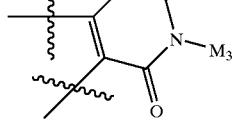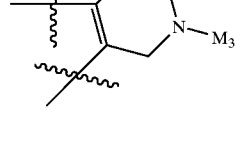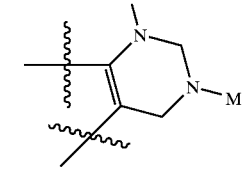
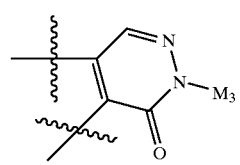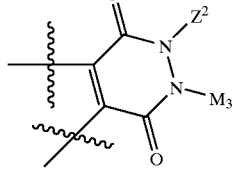
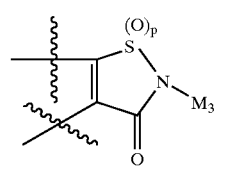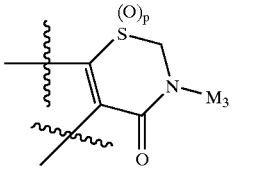

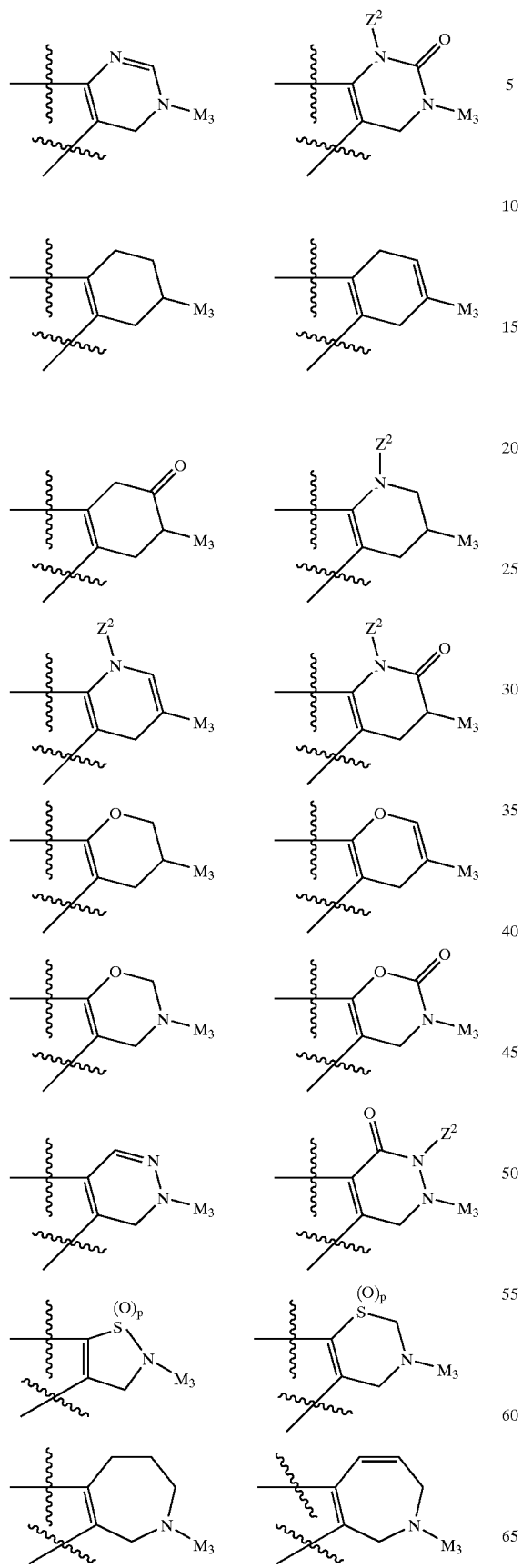
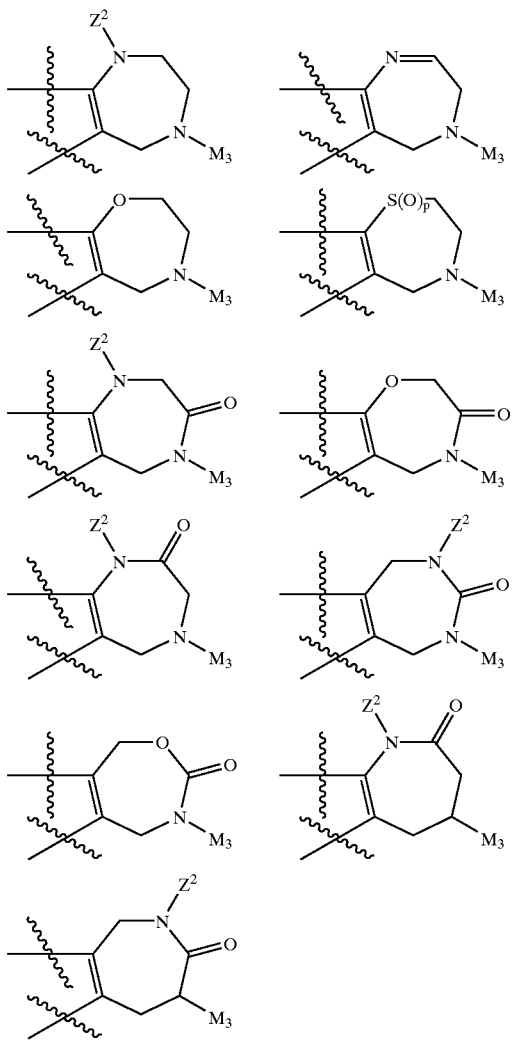
$z^2$ is selected from H, $C_{1-4}$ alkyl, phenyl, benzyl, $C(O)R^3$, and $S(O)_pR^{3c}$;
ring P, including $P_1$, $P_2$, $P_3$, and $P_4$ is selected from group:
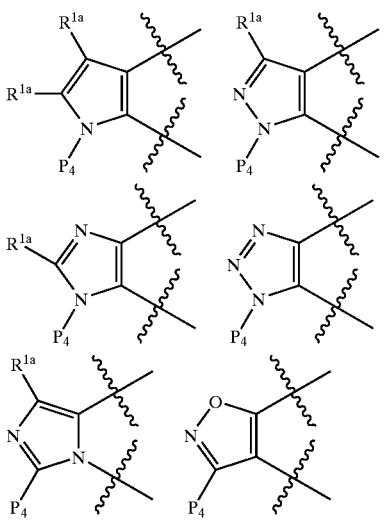

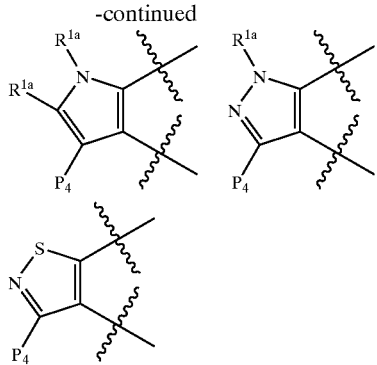
G is selected from the group:
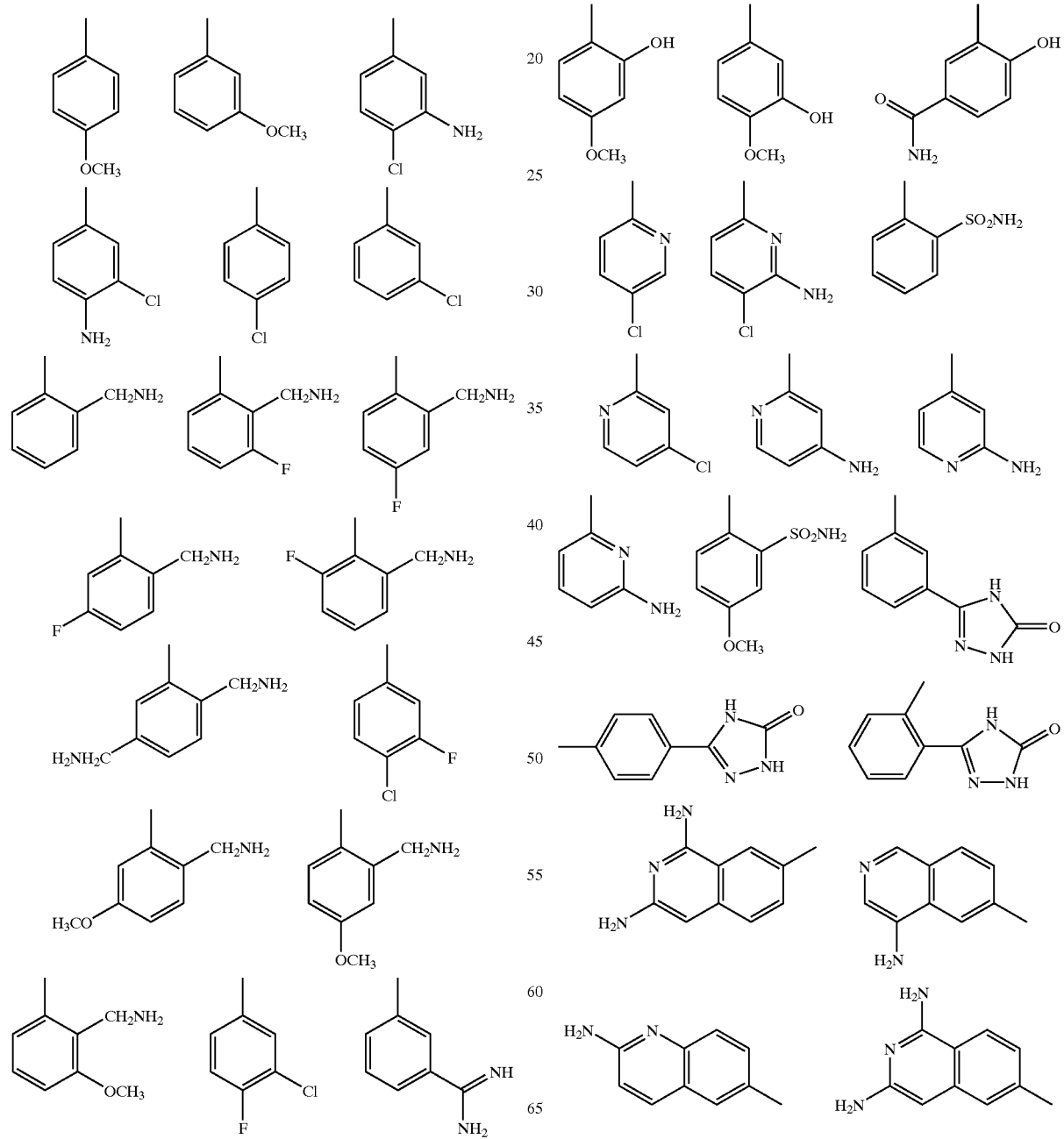

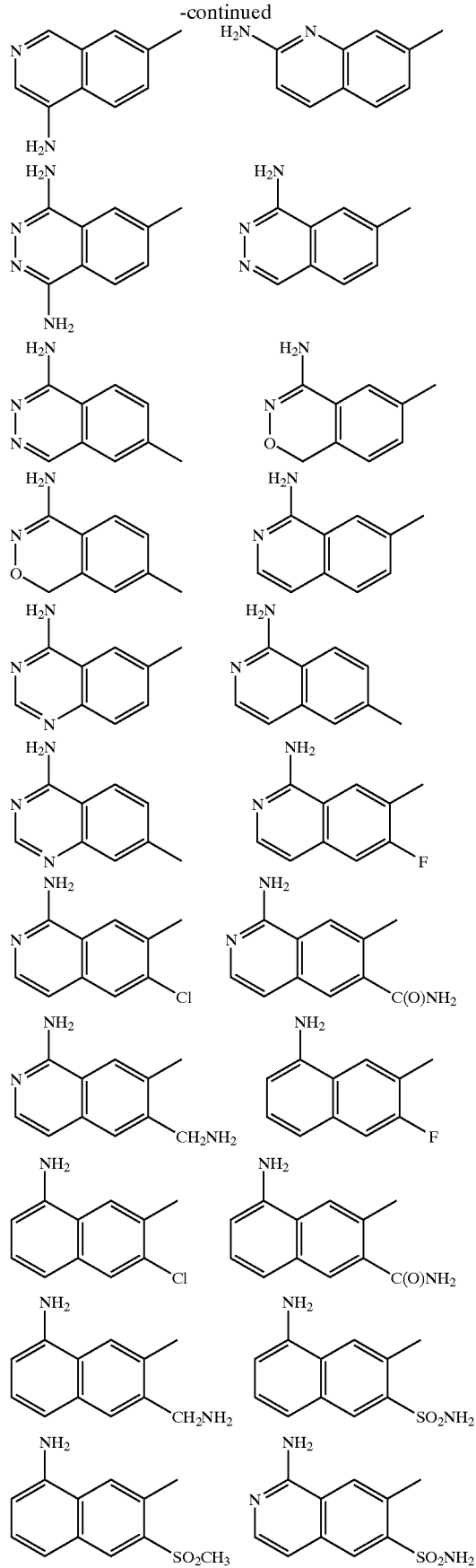
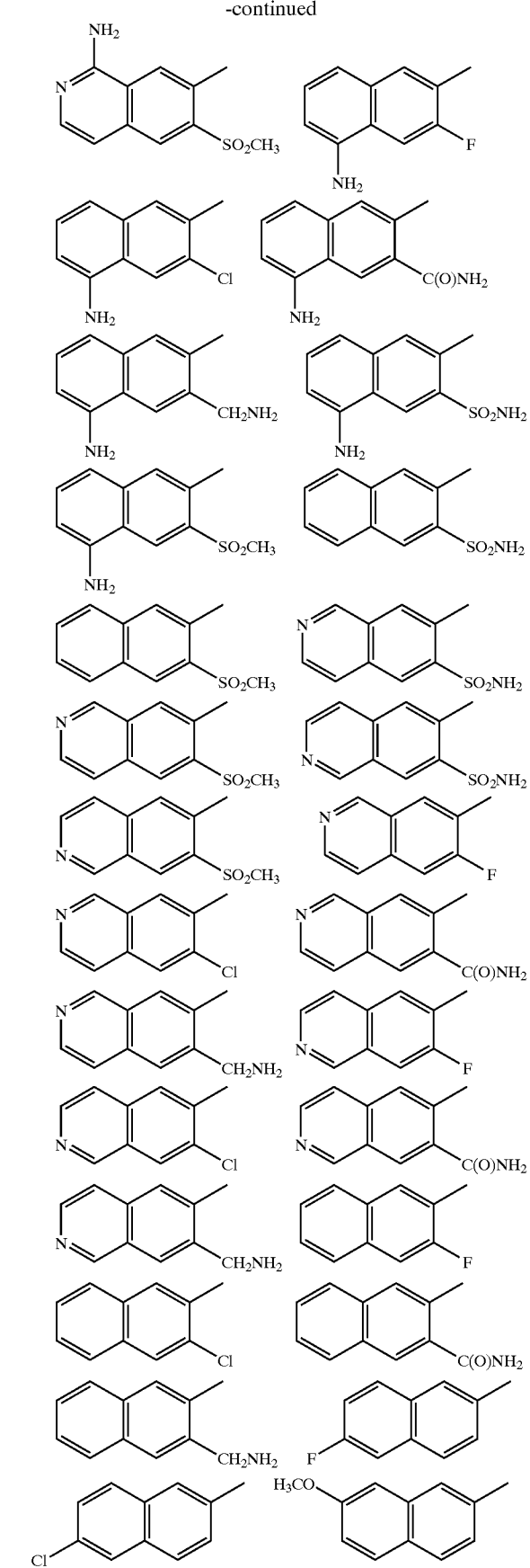

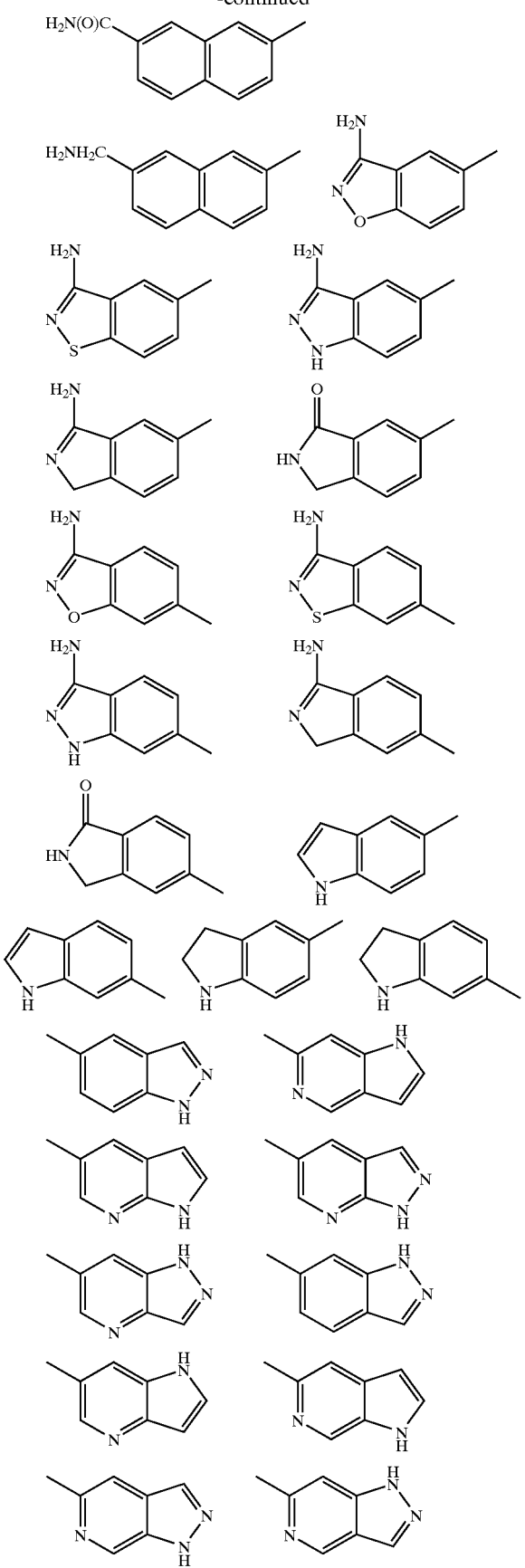
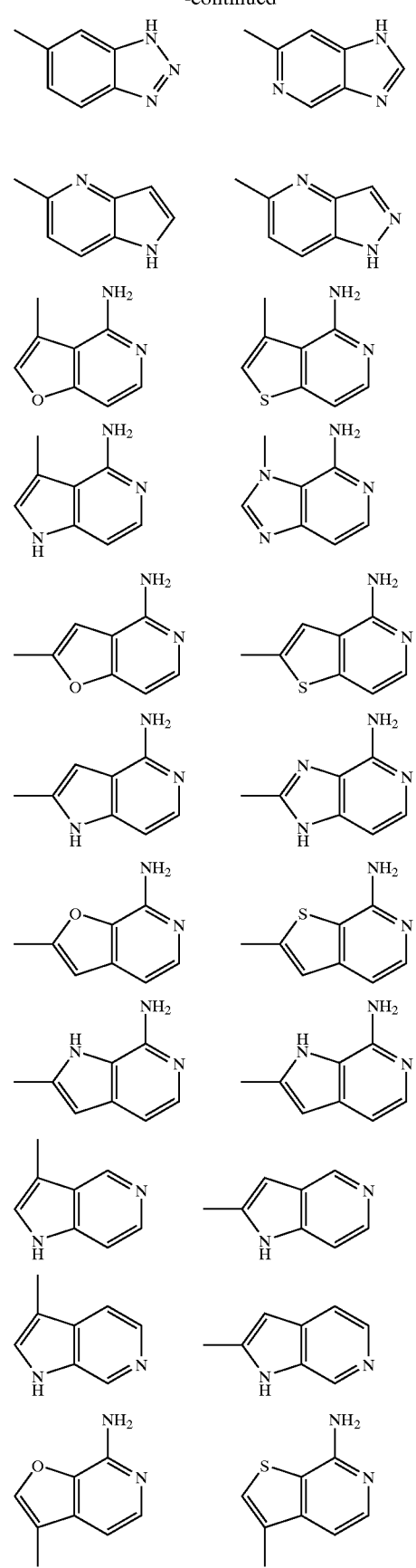

-continued

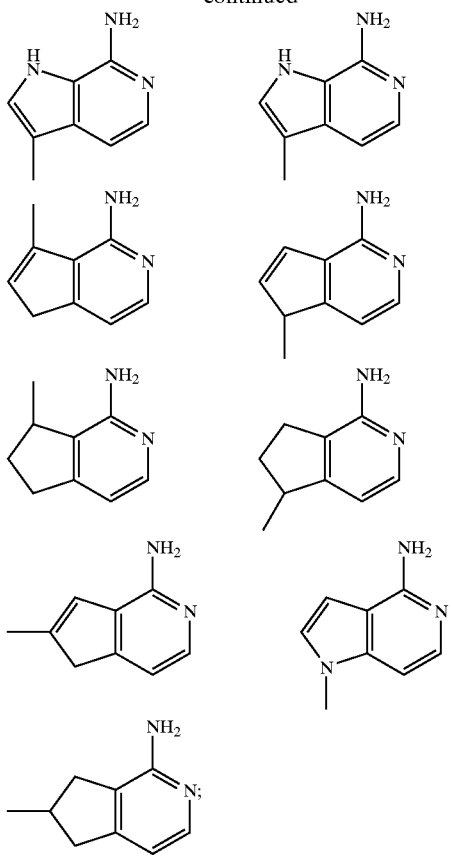

A is selected from one of the following carbocyclic and heterocyclic systems which are substituted with 0–2 $R^4$;
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from Y, X—Y, $CH_2NR^2R^{2a}$, and $CH_2CH_2NR^2R^{2a}$;

$G_1$ is absent or is selected from $(CR^3R^{3a})_{1-3}$, $(CR^3R^{3a})_uC(O)(CR^3R^{3a})_w$, $(CR^3R^{3a})_uO(CR^3R^{3a})_w$, $(CR^3R^{3a})_uNR^3(CR^3CR^{3a})_w$, $(CR^3R^{3a})_uC(O)NR^3(CR^3R^{3a})_w$, $(CR^3R^{3a})_uNR^3C(O)(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^3(CR^3R^{3a})_w$, and $(CR^3R^{3a})_uS(O)_2NR^3(CR^3R^{3a})_w$, wherein u+w total 0, 1, or 2, provided that $G_1$ does not form a N—N, N—O, N—S, $NCH_2N$, $NCH_2O$, or $NCH_2S$ bond with either group to which it is attached;

X is selected from —$(CR^2R^{2a})_{1-4}$—, —C(O)—, —C(=$NR^{1c}$)—, —$CR^2(NR^{1c}R^2)$—, —C(O)$CR^2R^{2a}$—, —$CR^2R^{2a}C(O)$, —C(O)$NR^2$—, —$NR^2C(O)$—, —C(O)$NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from one of the following carbocyclic and heterocyclic systems that are substituted with 0–2 $R^{4a}$;
cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;
alternatively, Y is selected from the following bicyclic heteroaryl ring systems:

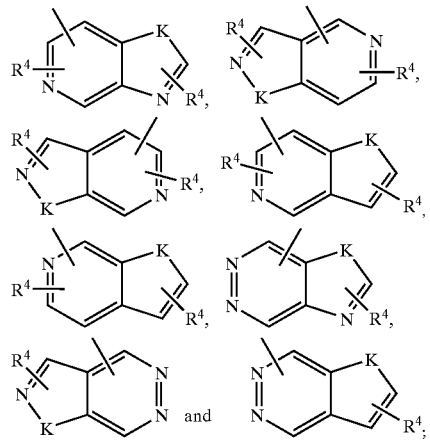

K is selected from O, S, NH, and N;

Z is selected from $CH_2O$, $OCH_2$, NH, $CH_2NH$, $NHCH_2$, $CH_2C(O)$, $C(O)CH_2$, C(O)NH, NHC(O), $CH_2S(O)_2$, $S(O)_2(CH_2)$, $SO_2NH$, and $NHSO_2$, provided that Z does not form a N—N, N—O, N—S, $NCH_2N$, $NCH_2O$, or $NCH_2S$ bond with either group to which it is attached;
alternatively, when
(a) B is other than an optionally substituted carbocycle; and,
(b) $G_1$ is $(CH_2)_uNR^3(CH_2)_w$ and u+w is 1 or 2, $(CH_2)_uC(O)NR^3(CH_2)_w$, $(CH_2)_uNR^3C(O)(CH_2)_w$, $(CH_2)_uS(O)NR^3(CH_2)_w$, $(CH_2)_uS(O)_2NR^3(CH_2)_w$, or $(CH_2)_uNR^3S(O)_2(CH_2)_w$;
then Z is other than $CH_2NH$, $NHCH_2$, C(O)NH, NHC(O), $CH_2S(O)_2$, $S(O)_2(CH_2)$, $SO_2NH$, and $NHSO_2$;
alternatively, when
(a) B is other than an optionally substituted carbocycle; and,
(b) Z is, $CH_2NH$, $NHCH_2$, C(O)NH, NHC(O), $CH_2S(O)_2$, $S(O)_2(CH_2)$, $SO_2NH$, and $NHSO_2$;
then $G_1$ is other than $(CR^3R^{3a})_uNR^3(CH_2)_w$ and u+w is 1, 2, 3, or 4, $(CH_2)_uC(O)NR^3(CH_2)_w$, $(CR^3R^{3a})_uNR^3C(O)(CH_2)_w$, $(CH_2)_uS(O)NR^3(CH_2)_w$, $(CR^3R^{3a})_uS(O)_2NR^3(CH_2)_w$, or $(CH_2)_uNR^3S(O)_2(CH_2)_w$.

[3] In another preferred embodiment, the present invention provides a novel compound, wherein:

ring M is substituted with 0–2 $R^{1a}$ and is selected from the group:

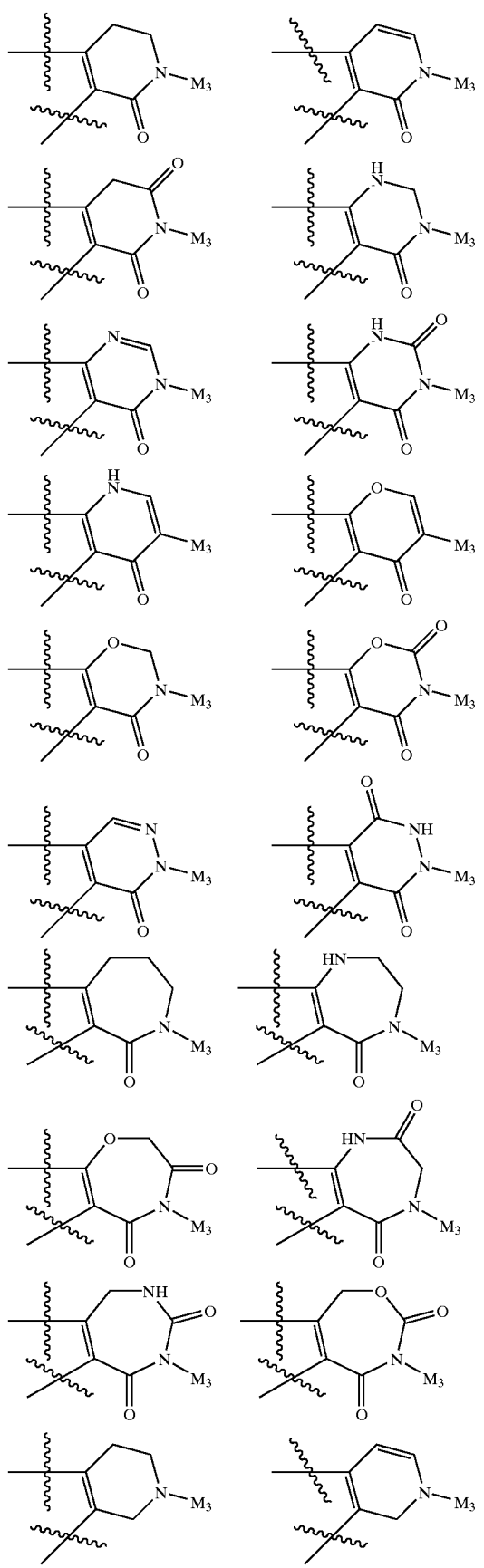
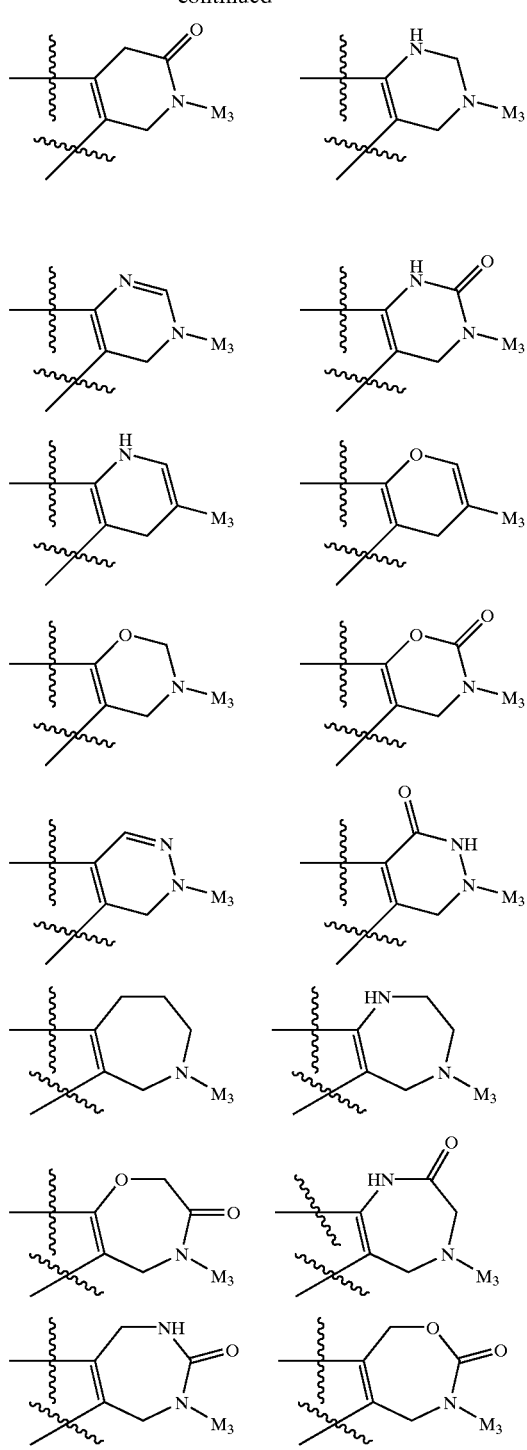
ring P, including $P_1$, $P_2$, $P_3$, and $P_4$ is selected from group:
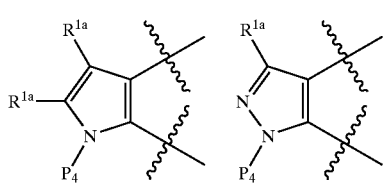

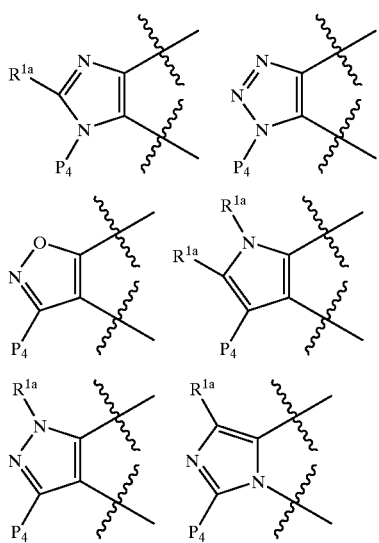
G is selected from the group:
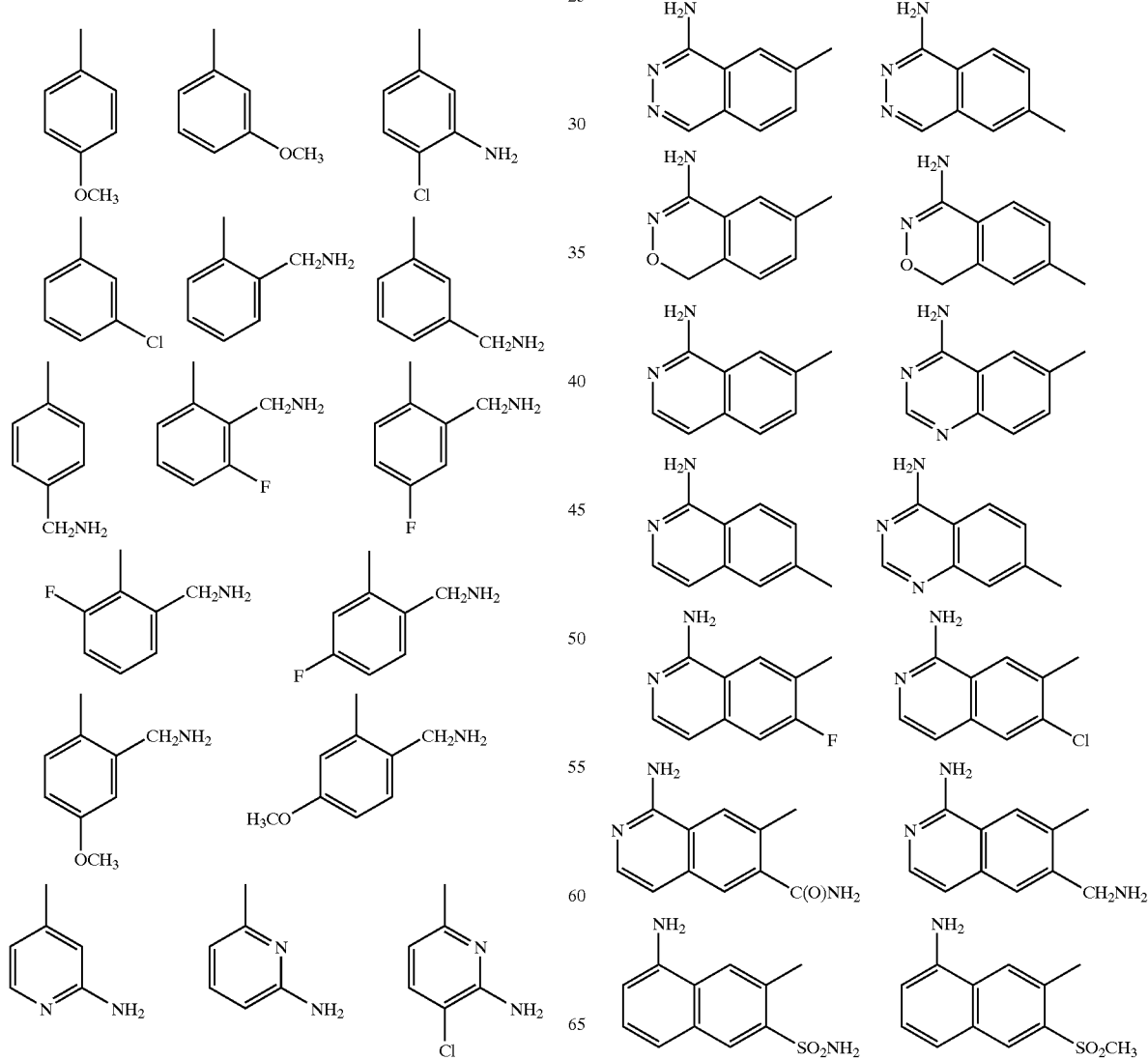

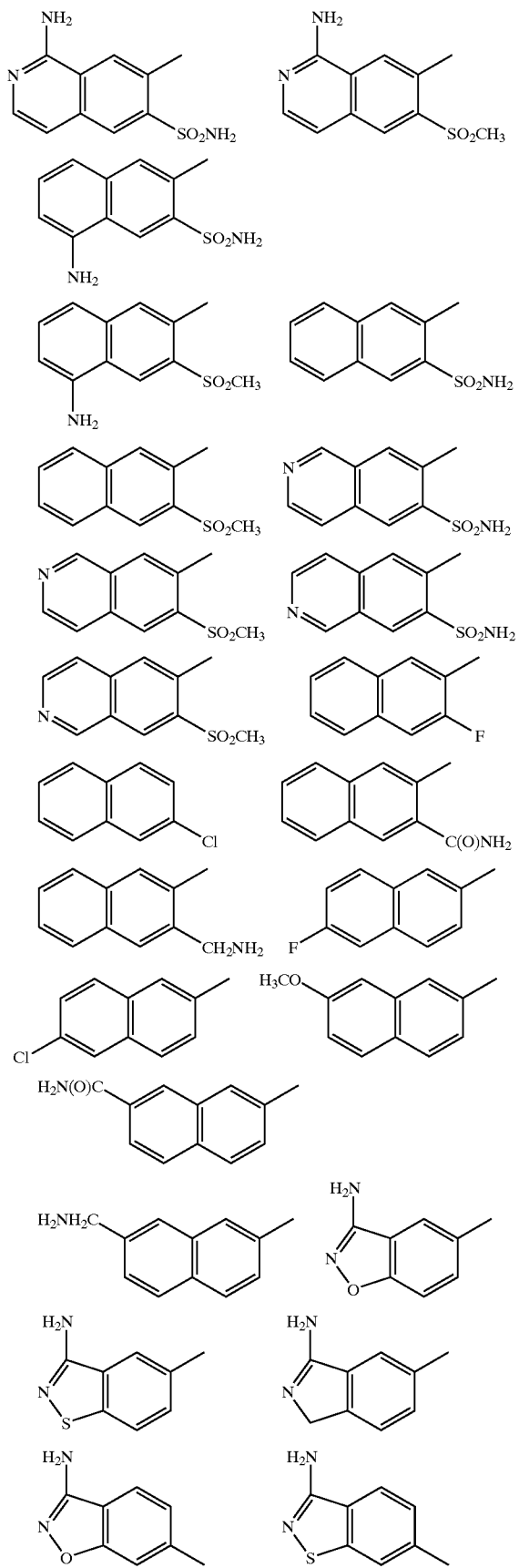
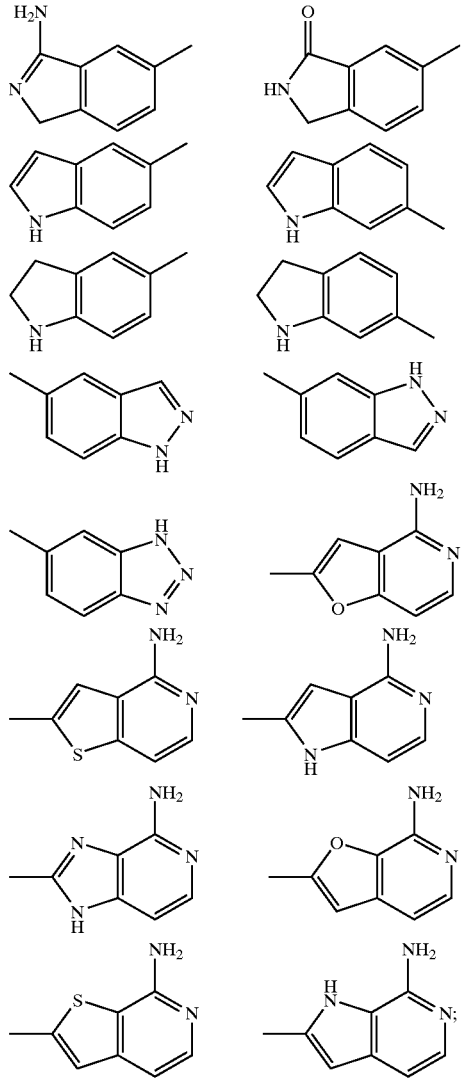

G₁ is absent or is selected from $CH_2$, $CH_2CH_2$, $CH_2O$, $OCH_2$, NH, $CH_2NH$, $NHCH_2$, $CH_2C(O)$, $C(O)CH_2$, $C(O)NH$, $NHC(O)$, $CH_2S(O)_2$, $S(O)_2(CH_2)$, $SO_2NH$, and $NHSO_2$, provided that G₁ does not form a N—N, N—O, N—S, $NCH_2N$, $NCH_2O$, or $NCH_2S$ bond with either group to which it is attached;

Z is selected from $CH_2O$, $OCH_2$, NH, $CH_2NH$, $NHCH_2$, $CH_2C(O)$, $C(O)CH_2$, $C(O)NH$, $NHC(O)$, $CH_2S(O)_2$, $S(O)_2$ ($CH_2$), $SO_2NH$, and $NHSO_2$, provided that Z does not form a N—N, N—O, N—S, $NCH_2N$, $NCH_2O$, or $NCH_2S$ bond with either group to which it is attached; alternatively, when (a) B is other than an optionally substituted carbocycle; and, (b) G₁ is $CH_2NH$, $NHCH_2$, $C(O)NH$, $NHC(O)$, $CH_2S(O)_2$, $S(O)_2(CH_2)$, $SO_2NH$, and $NHSO_2$;

then Z is other than $CH_2NH$, $NHCH_2$, $C(O)NH$, $NHC(O)$, $CH_2S(O)_2$, $S(O)_2(CH_2)$, $SO_2NH$, and $NHSO_2$;

alternatively, when (a) B is other than an optionally substituted carbocycle; and, (b) Z is $CH_2NH$, $NHCH_2$, $C(O)NH$, $NHC(O)$, $CH_2S(O)_2$, $S(O)_2(CH_2)$, $SO_2NH$, and $NHSO_2$;

then G$_1$ is other than CH$_2$NH, NHCH$_2$, C(O)NH, NHC(O), CH$_2$S(O)$_2$, S(O)$_2$(CH$_2$), SO$_2$NH, and NHSO$_2$.
[4] In another preferred embodiment, the present invention provides a novel compound, wherein:
ring M is substituted with 0–1 R$^{1a}$ and is selected from the group:
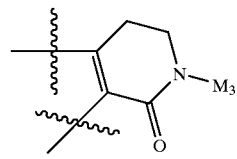 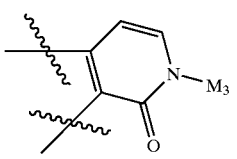
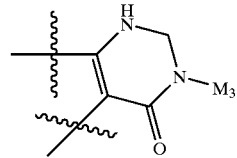
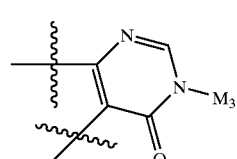
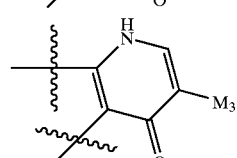
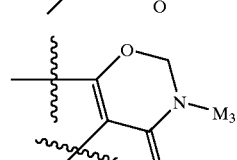
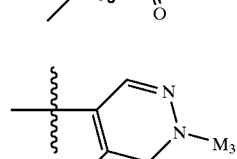
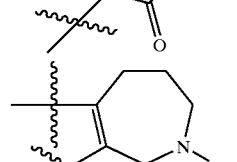
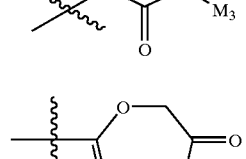
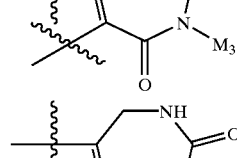
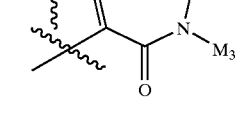
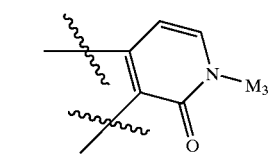
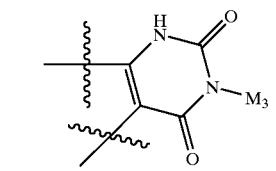
-continued
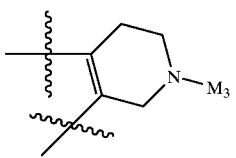 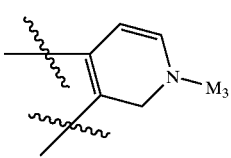
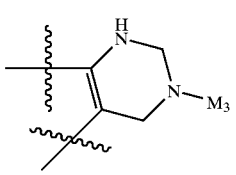
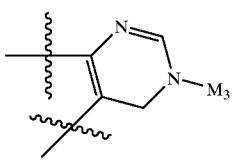
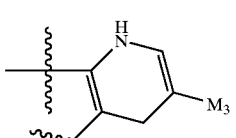
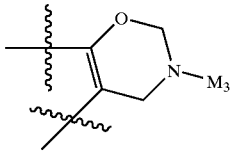
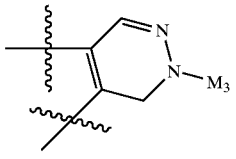
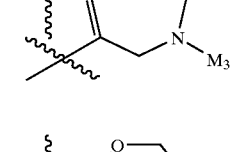
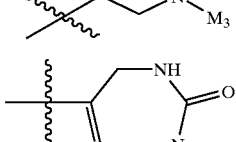
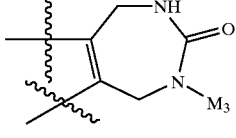

G is selected from:

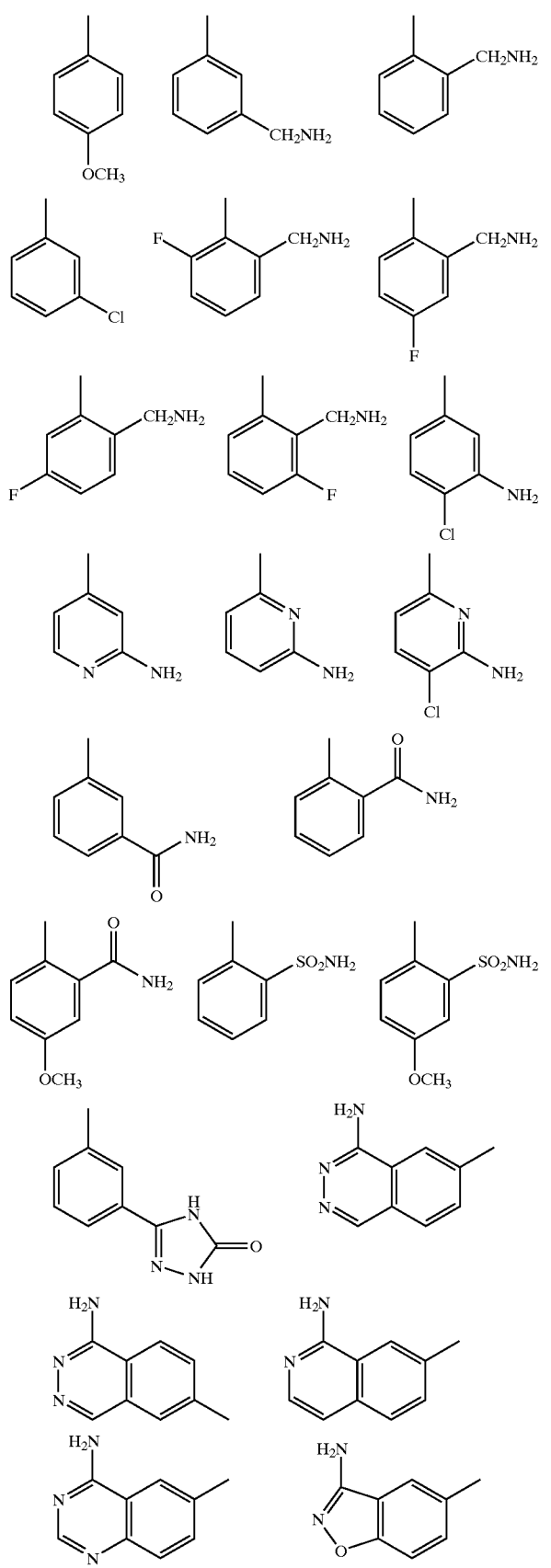

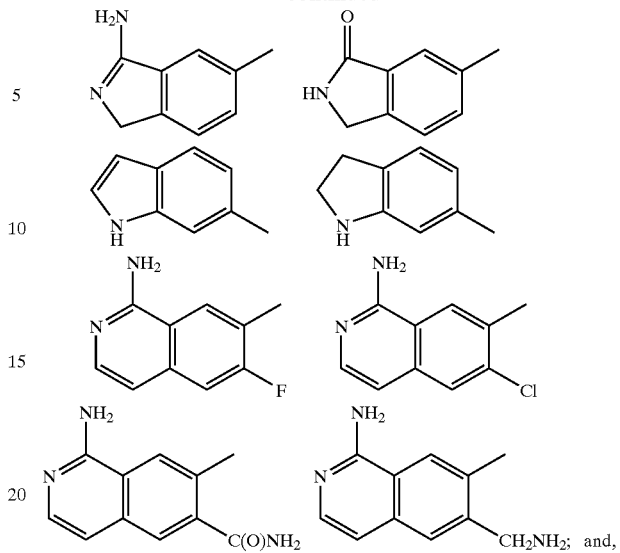

$G_1$ is absent.

[5] In another preferred embodiment, the present invention provides a novel compound, wherein;

ring M is substituted with 0–1 $R^{1a}$ and is selected from the group:

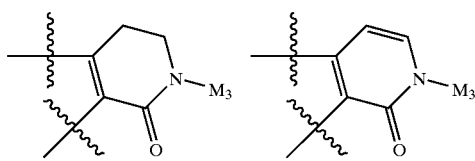

ring P, including P1, P2, $P_3$, and $P_4$ is selected from group:

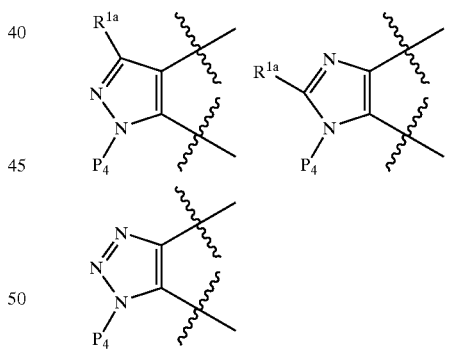

A is selected from phenyl, pyridyl, and pyrimidyl, and is substituted with 0–2 $R^4$;

B is selected from phenyl, pyrrolidino, N-pyrrolidino-carbonyl, morpholino, N-morpholino-carbonyl, 1,2,3-triazolyl, imidazolyl, and benzimidazolyl, and is substituted with 0–1 $R^{4a}$;

$R^2$, at each occurrence, is selected from H, $CH_3$, $CH_2CH_3$, cyclopropylmethyl, cyclobutyl, and cyclopentyl;

$R^{2a}$, at each occurrence, is H or $CH_3$;

alternatively, $R^2$ and $R^{2a}$, together with the atom to which they are attached, combine to form pyrrolidine substituted with 0–2 $R^{4b}$ or piperidine substituted with 0–2 $R^{4b}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $(CH_2)_rOR^2$, $(CH_2)_rNR^2R^{2a}$, $S(O)_pR^5$, $SO_2NR^2R^{2a}$, and 1-$CF_3$-tetrazol-2-yl;

$R^{4b}$, at each occurrence, is selected from H, $CH_3$, and OH;

$R^5$, at each occurrence, is selected from $CF_3$, $C_{1-6}$ alkyl, phenyl, and benzyl; and, r, at each occurrence, is selected from 0, 1, and 2.

[6] In another preferred embodiment, the present invention provides a novel compound, wherein;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-methylaminomethyl) phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl) aminomethyl)phenyl, 2-(N-(4-hydroxypiperidinyl) methyl)phenyl, and 2-(N-(3-hydroxypyrrolidinyl)methyl) phenyl.

[7] In another preferred embodiment, the present invention provides a novel compound selected from:

6-(3-(amidino)phenyl)-1-{2'-[aminosulfonyl]-1,1'-biphenyl-4-yl}-3-methyl-7-oxo-4,5,6,7-tetrahydro-1H-pyrazolo[3,4-c]pyridine;

N-[1-{4-[1-(4-methoxyphenyl)-3-(trifluoromethyl)-1,4,5,7-tetrahydro-6H-pyrazolo[3,4-c]pyridin-6yl]phenyl}-1H-imidazol-2-yl)methyl]-N,N-dimethylamine;

(3S)—N-[1-{4-[1-(4-methoxyphenyl)-3-(trifluoromethyl)-1,4,5,7-tetrahydro-6H-pyrazolo[3,4-c]pyridin-6yl]-1,1'-biphenyl-2yl}methyl-3-pyrrolidinol; and, 7-{2'-[(4-hydroxy-1-piperidinyl)methyl]-1,1'-biphenyl-4-yl}-1-(4-methoxyphenyl)-3-(trifluoromethyl)-6,7-dihydroimidazo[1,5-a]pyrazin-8(5H)-one;

or a pharmaceutically acceptable salt form thereof.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a compound of the present invention for use in therapy.

In another embodiment, the present invention provides the use of a compound of the present invention as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

Preferably, the molecular weight of compounds of the present invention is less than about 500, 550, 600, 650, 700, 750, 800, 850, 900, 950, or 1000 grams per mole. More preferably, the molecular weight is less than about 950 grams per mole. Even more preferably, the molecular weight is less than about 850 grams per mole. Still more preferably, the molecular weight is less than about 750 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is also intended to include all stable oxides of thiol and amino groups, even when not specifically written. When an amino group is listed as a substituent, the N-oxide derivative of the amino group is also included as a substituent. When a thiol group is present, the S-oxide and S,S-dioxide derivatives are also included.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-10}$ alkenyl is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-10}$ Alkynyl is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O, and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O, and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The pyridone or cycloheptanone moieties of the present invention are generally constructed according to the method outlined in Scheme-1.

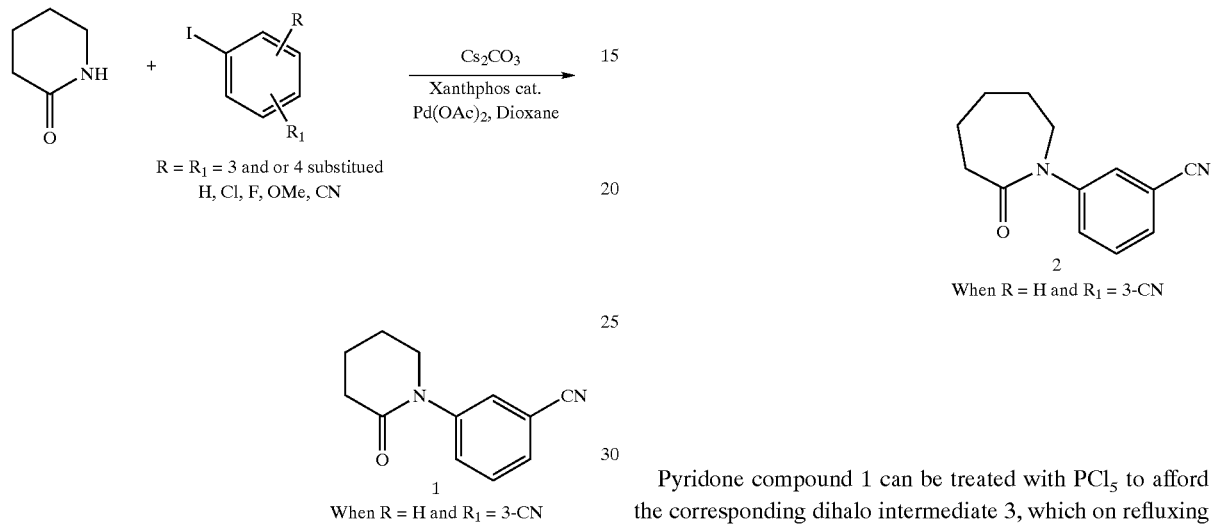

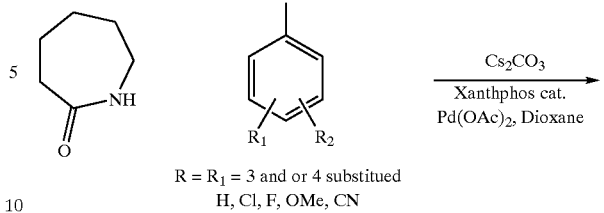

Pyridone compound 1 can be treated with $PCl_5$ to afford the corresponding dihalo intermediate 3, which on refluxing with morpholine should provide enamine 4 (Scheme-2).

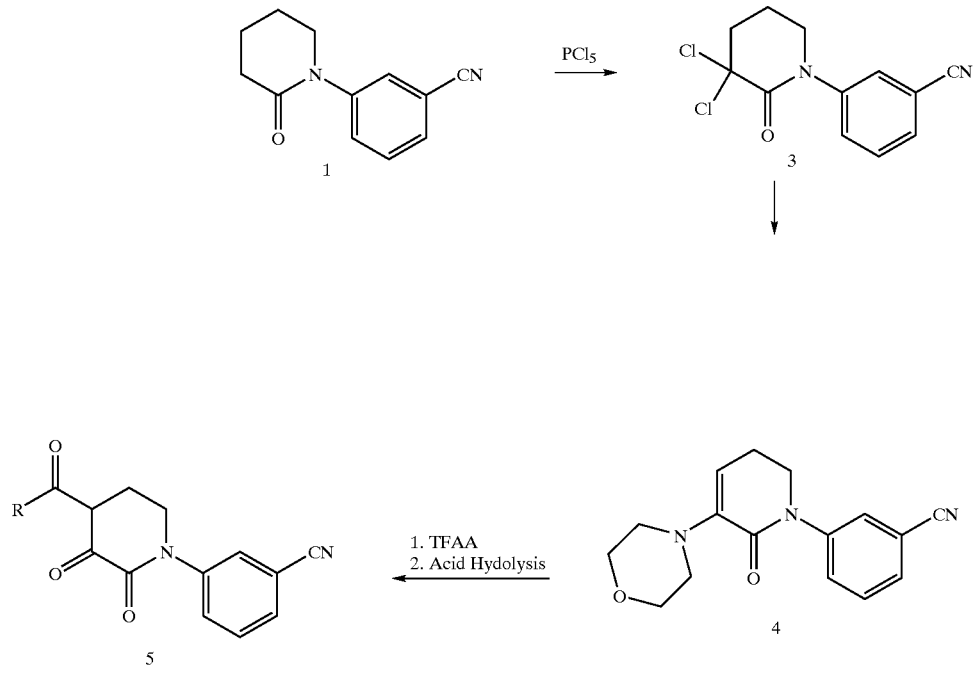

Morpholine enamine 4 can be converted to the diketo cyclic amide compound 5 by treatment with an appropriate acid chloride or anhydride followed by acid hydrolysis. Alternatively, enamine 4 can be subjected to a [3+2] cycloaddition (Scheme-3) with an appropriate nitrile oxide to afford the cyloadduct that on treatment with acid affords the corresponding isoxazole. The isoxazole can be reduced using conventional techniques known in the art to afford a diverse set of diketo cyclic intermediates such as 5. Condensation of 5 with an appropriate hydrazone should afford pyrazoline intermediates, which on treatment with acid should afford the desired pyrazole compounds of the present invention. Reduction of the amide carbonyl with borane should also afford the pyrazolopiperidyl intermediates as shown in scheme-3.

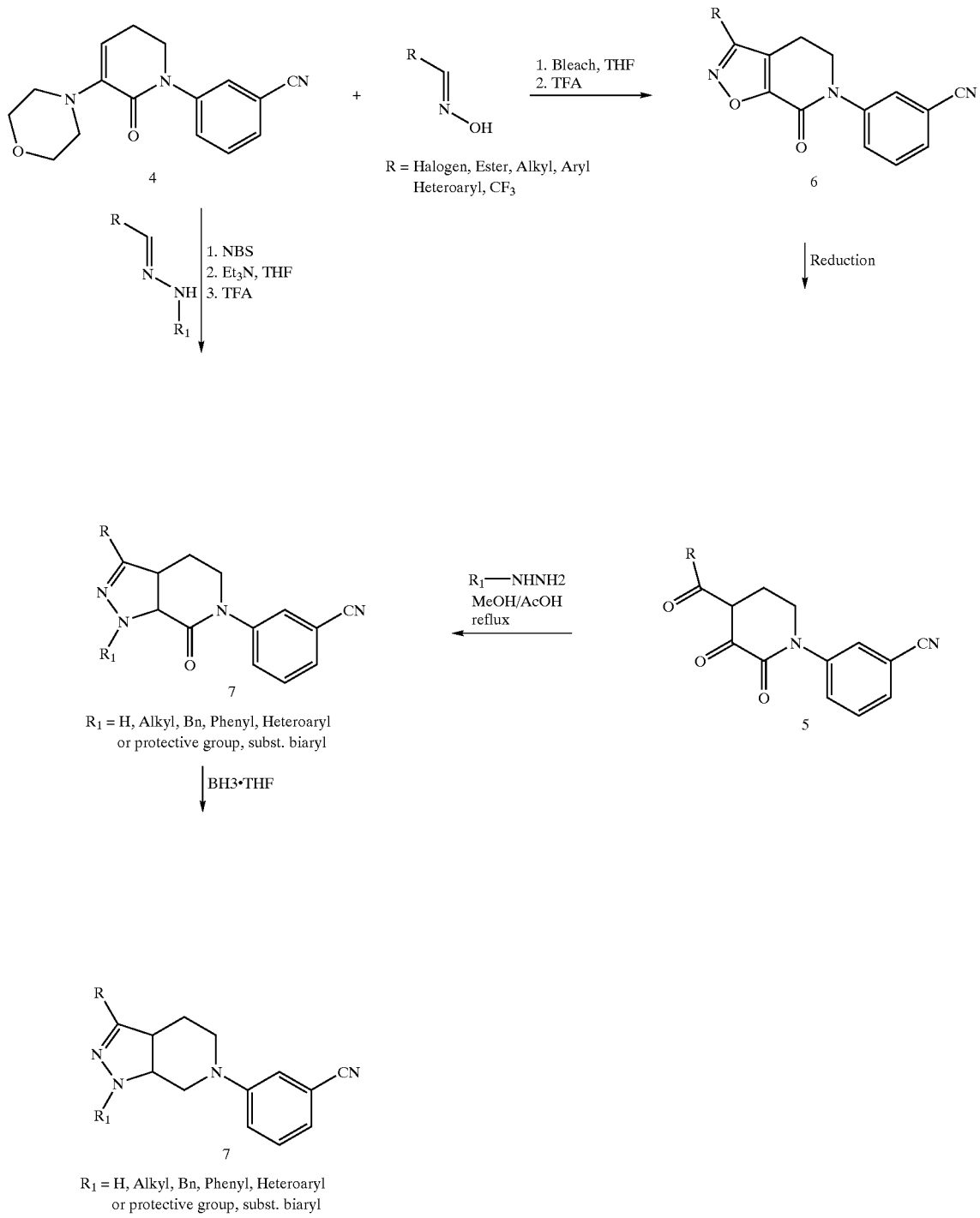

In the case when R₁ is a substituted haloaryl or a substituted halo-heteroaryl, the intermediate can be subjected to cross-coupling Suzuki reactions to afford biaryl or heteroaryl derivatives (Scheme-4). Alternatively similar results can be obtained using Stille tin-palladium coupling procedures. Depending on the type of boronic acid employed, various compounds of this invention can be obtained. Alternatively, the halo precursors can be subjected to Ullman copper coupling procedures to afford various nitrogen heterocycles (such as Example 9). This can be further reduced to afford compounds of this invention such as the pyrazolopiperidyl analog shown in scheme-4.

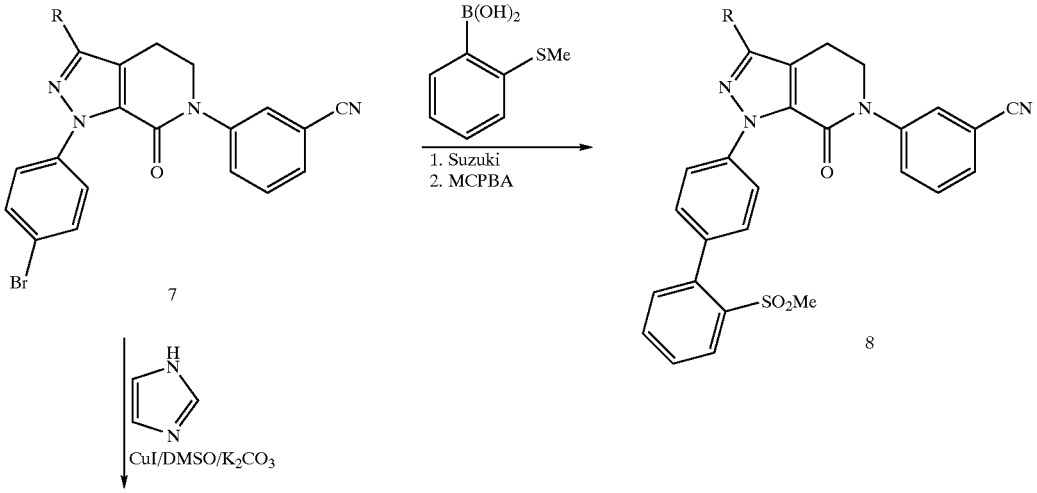

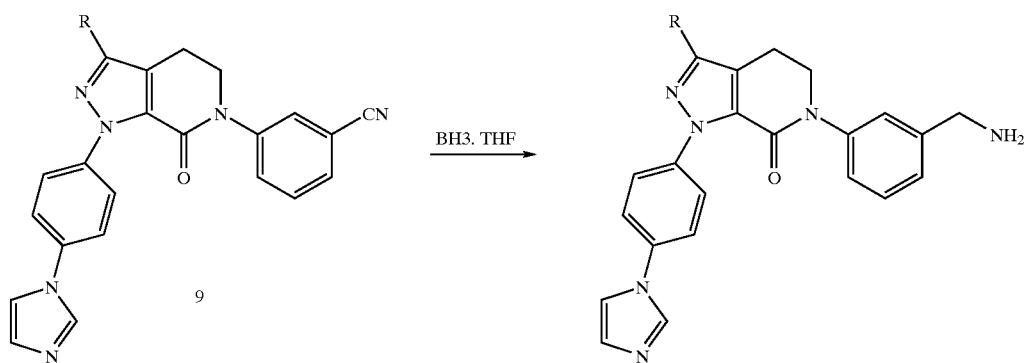

In the case where $R^1$ is a proton in intermediate 7, it can be coupled to various isocyanates or sulfonyl chlorides to afford the corresponding ureas or sulfonamide derivatives (Scheme-5). Alkylation can also afford the desired alkyl derivatives. The corresponding halo intermediates can be subjected to Suzuki or Ullman coupling procedures described previously to obtain compounds of the present invention.

Scheme-5

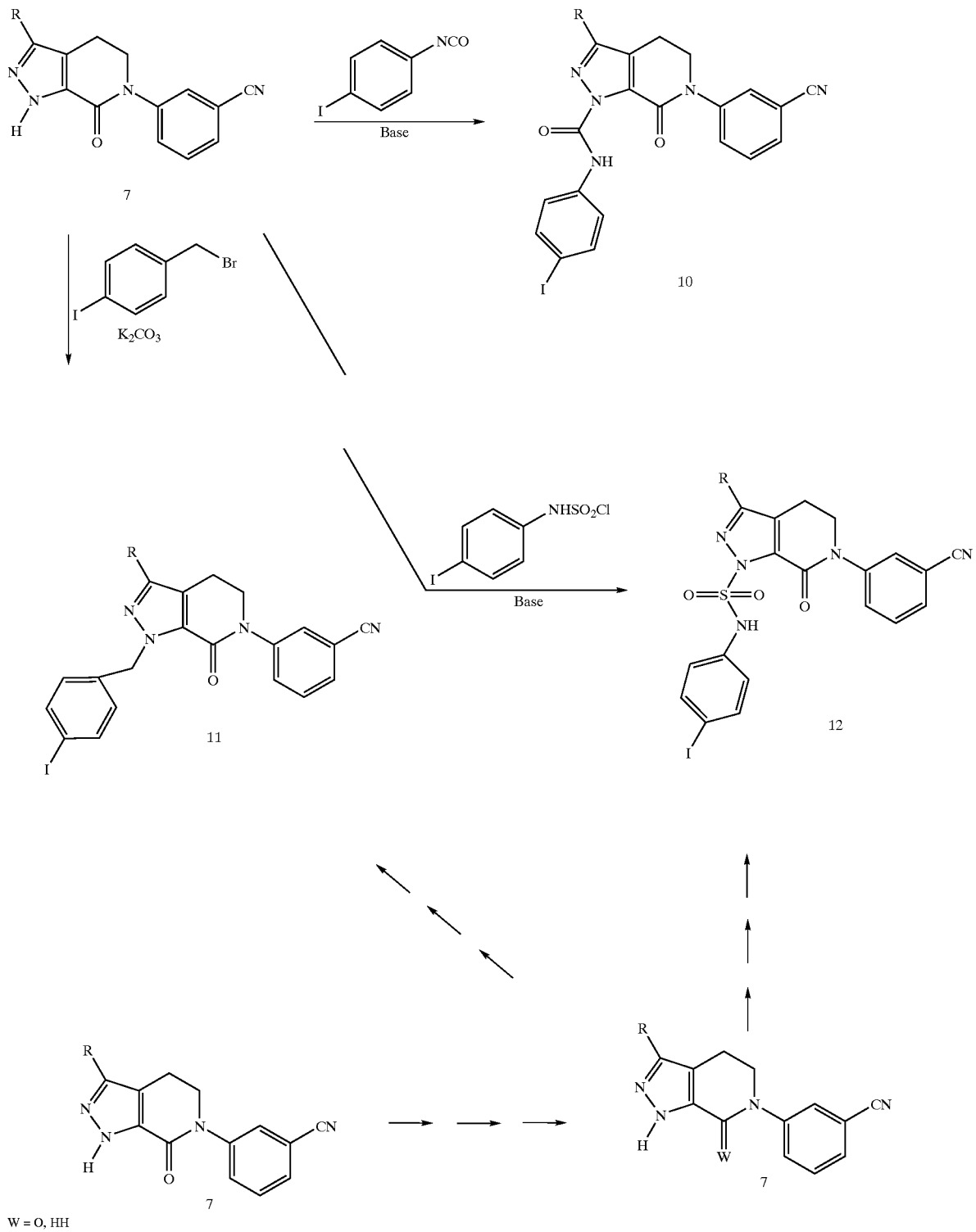

W = O, HH

It should be noted that the cyano functionality can be converted to benzamidine, benzamidine, hydroxyamidine, and amidinocarbamoyl species by the method shown in Scheme-6. Other compounds of this invention lacking the camido carbonyl can be directly btained by the reduction of the pyrazole intermediate 7 as previously discussed. Following the procedures in scheme-5 other compounds of this invention ca be obtained.

Scheme-6

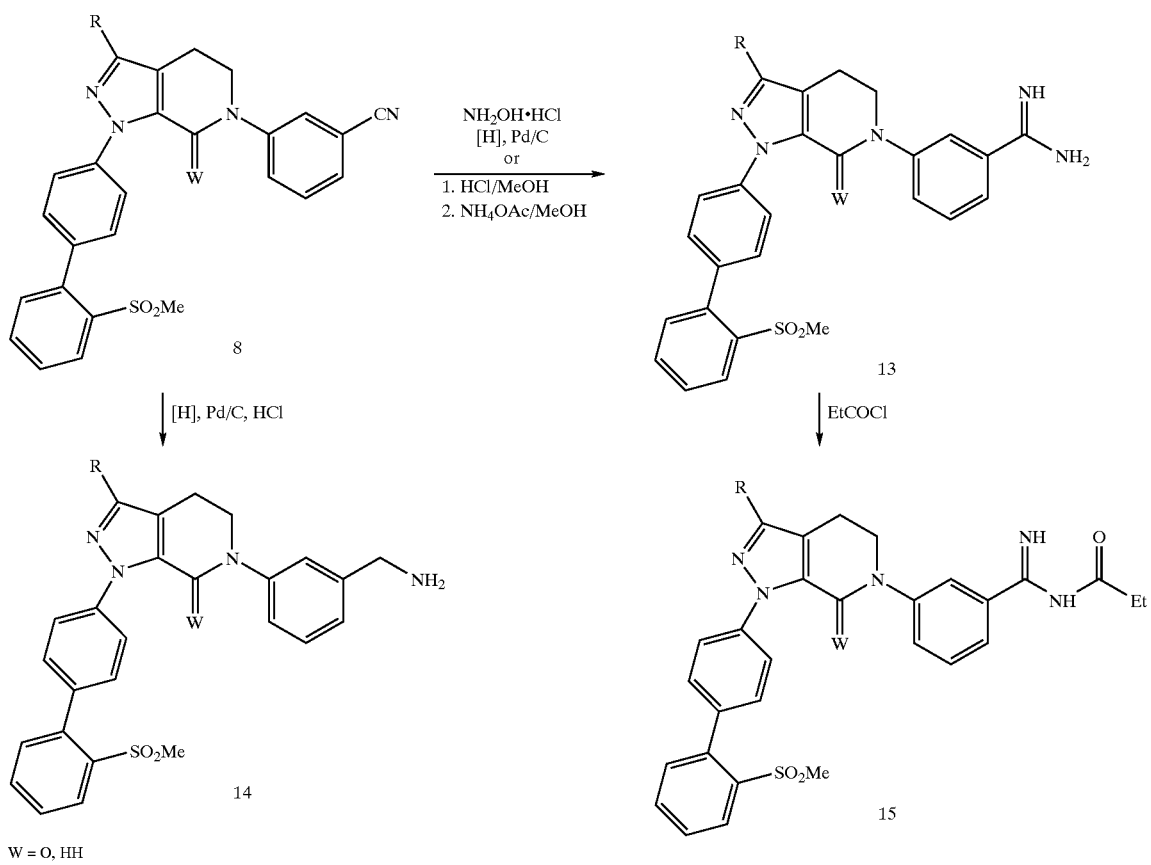

W = O, HH

Other cyano precursors can be converted to various compounds of the present invention as illustrated in Scheme-7.

Scheme-7

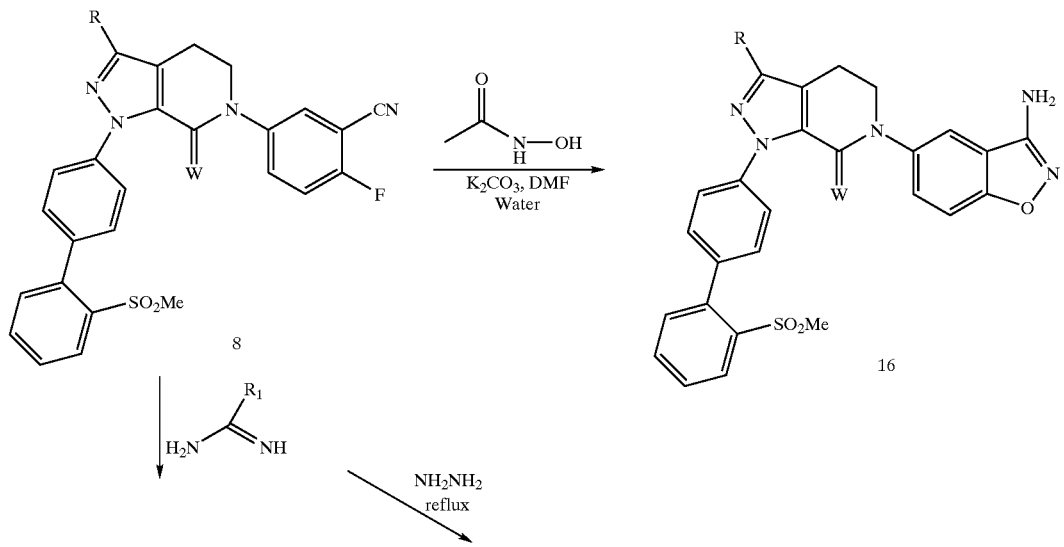

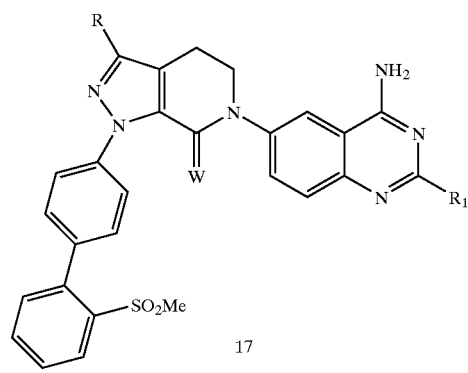
17
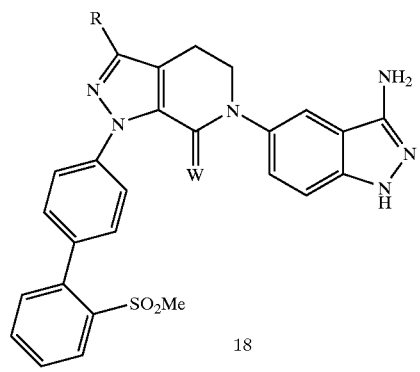
18
Other pyrazole compounds of the present invention can be prepared via methods illustrated in Scheme-8.
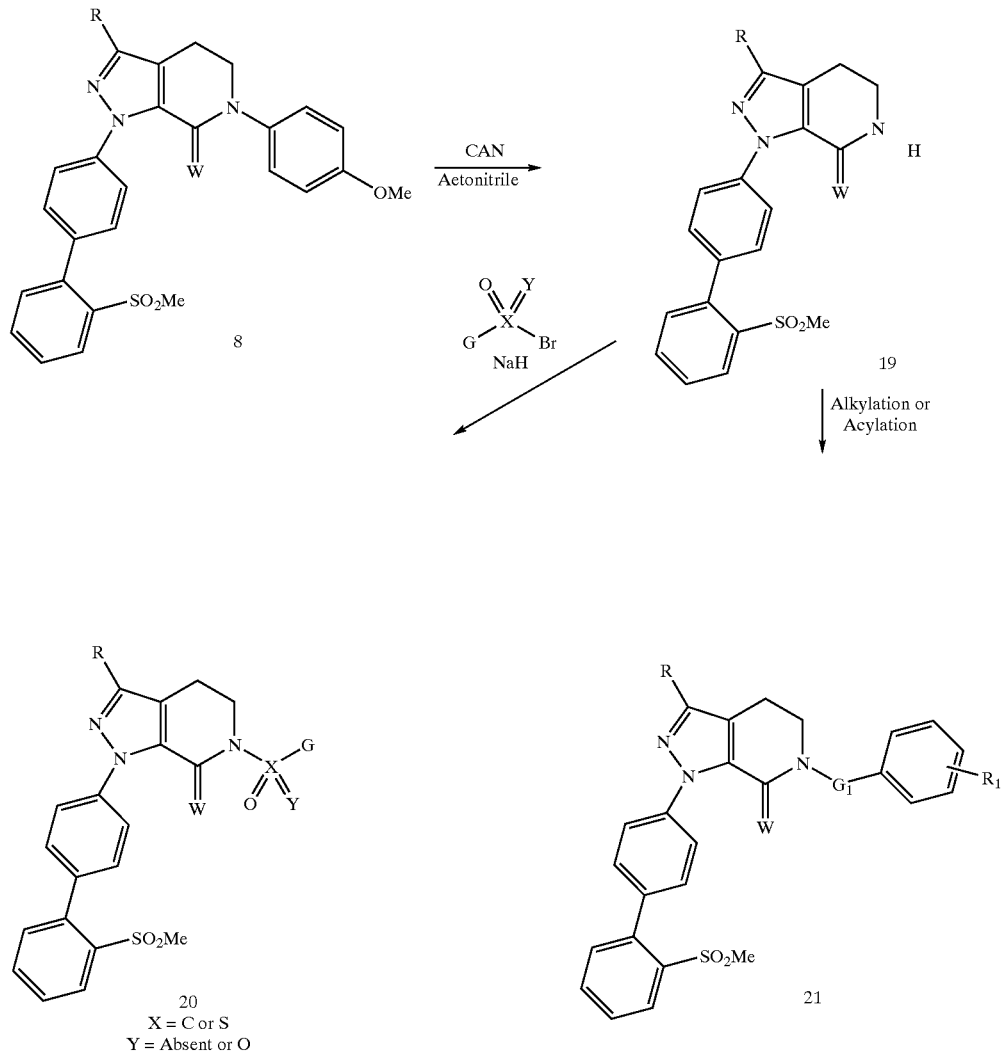
Scheme-8
20
X = C or S
Y = Absent or O
21
W = O, HH It should be noted that pyrazolo-cycloheptyl-amido analogs such as that illustrated in Scheme-1 could also be subjected to the methods described above to obtain compounds of the present invention.

Pyrazoles (or other 5-membered heterocycles) of this invention wherein both $G_1$ and Z are present can be easily obtained via intermediates shown in schemes 1–7.

Alternatively they can be prepared via the methodology outlined in scheme-9. Those who are skilled in the art can easily accomplish elaborations of these to compounds of this invention.

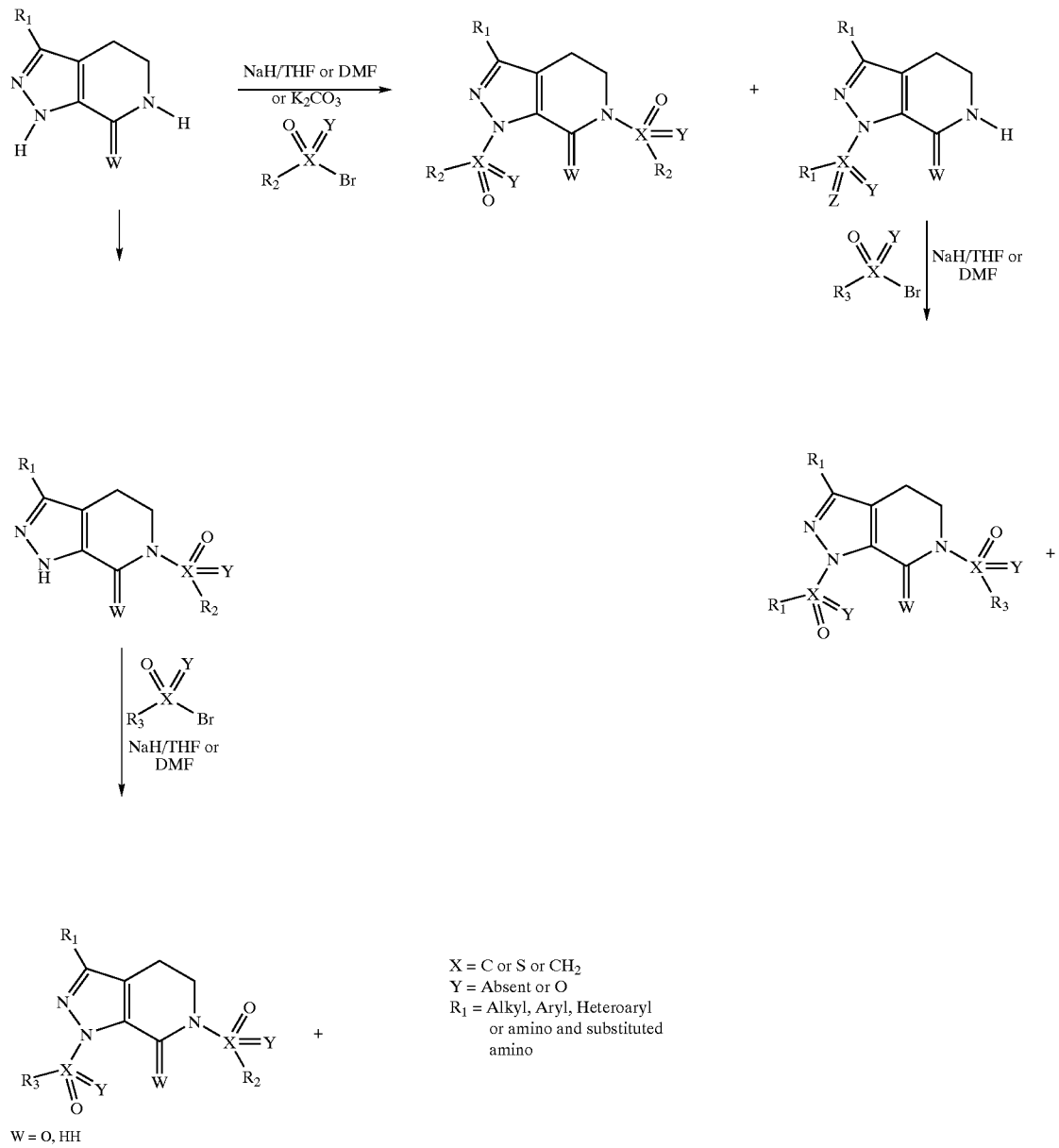

Scheme-9

X = C or S or $CH_2$
Y = Absent or O
$R_1$ = Alkyl, Aryl, Heteroaryl or amino and substituted amino

W = O, HH

Triazoles of the present invention can be prepared via [3+2] cycloaddition of the morpholine enamine intermediate from scheme-2 with an appropriate azido precursor shown inscheme-10. Elimination of the morpholino itermediate should afford key intermediates that can then be transformed to compounds of the present invention via the methods previously shown.

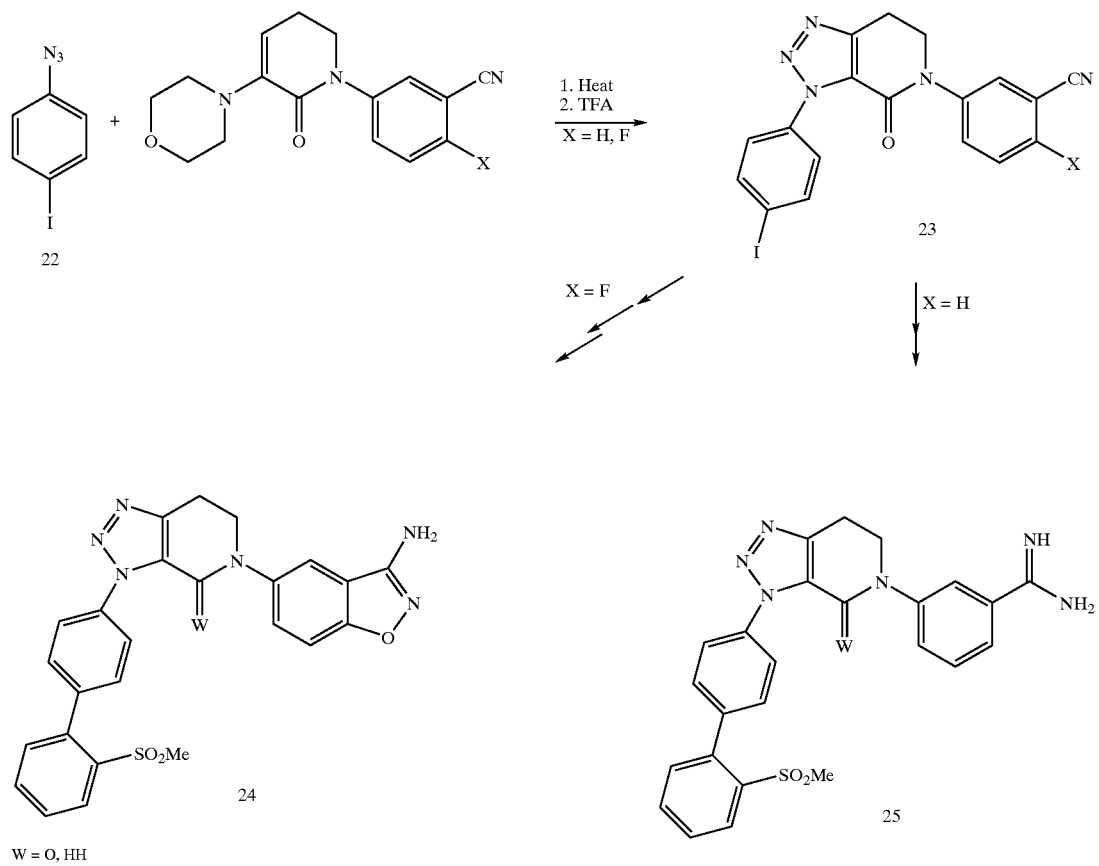

Scheme-10

Various other triazoles can be prepared via the methods employed for the pyrazole analogs. Imidazole analogs can also be prepared from the morpholine enamine intermediate shown in Scheme-11.

Scheme-11

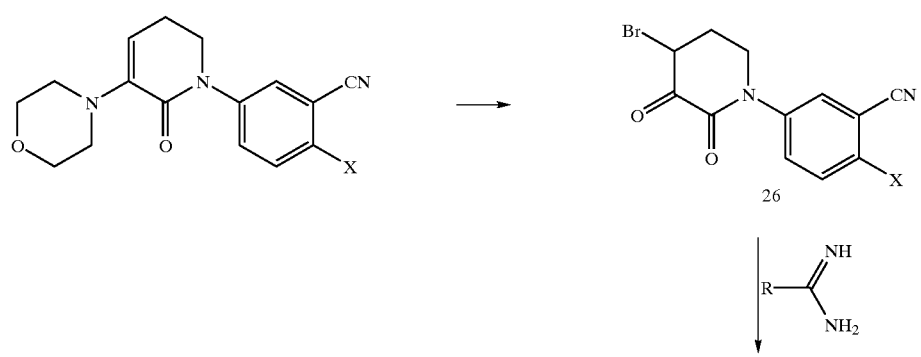

53
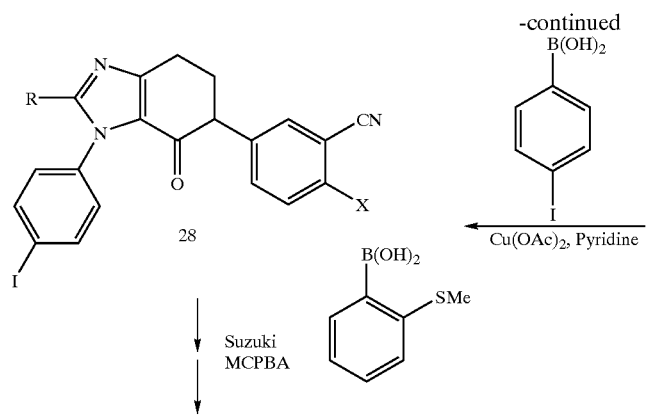
28
54
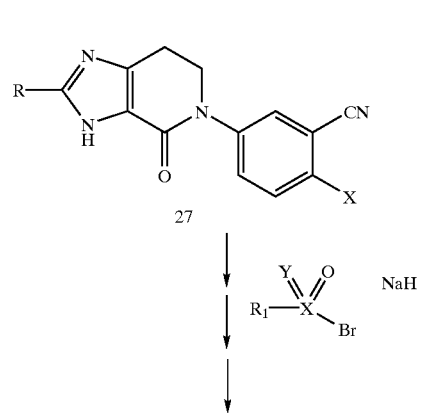
27
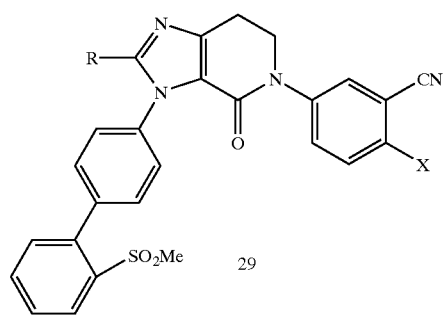
29
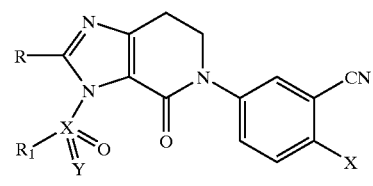
30
X = C or S
Y = Absent or O
R₁ = Alkyl, Aryl, Heteroaryl or amino and substituted amino
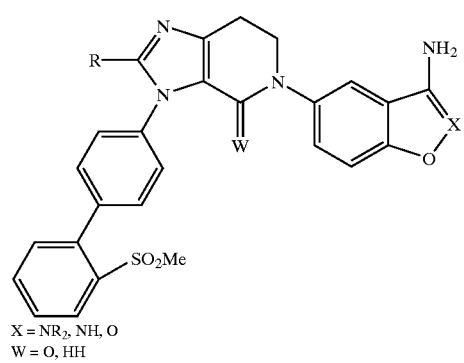
X = NR₂, NH, O
W = O, HH
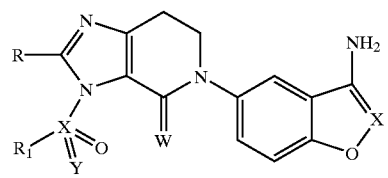

Imidazole precursor analogs can also be converted to the compounds of the present invention via the methods previously described.

Alternatively, pyrazole, imidazole, and triazole carboxylates can also serve as versatile intermediates towards the synthesis of other analogs of this invention. For example, N-1 phenyl pyrazole 5-carboxlates can be nitrated at the 4-position to the corresponding nitro analog (Scheme-12). Reduction of the nitro to the amino can be accomplished quite readily. The 4-amino-5-carboxylate can be converted to an appropriate amino-amido species that then can be cyclized to various aza-bicyclics via methods known to those in the art.

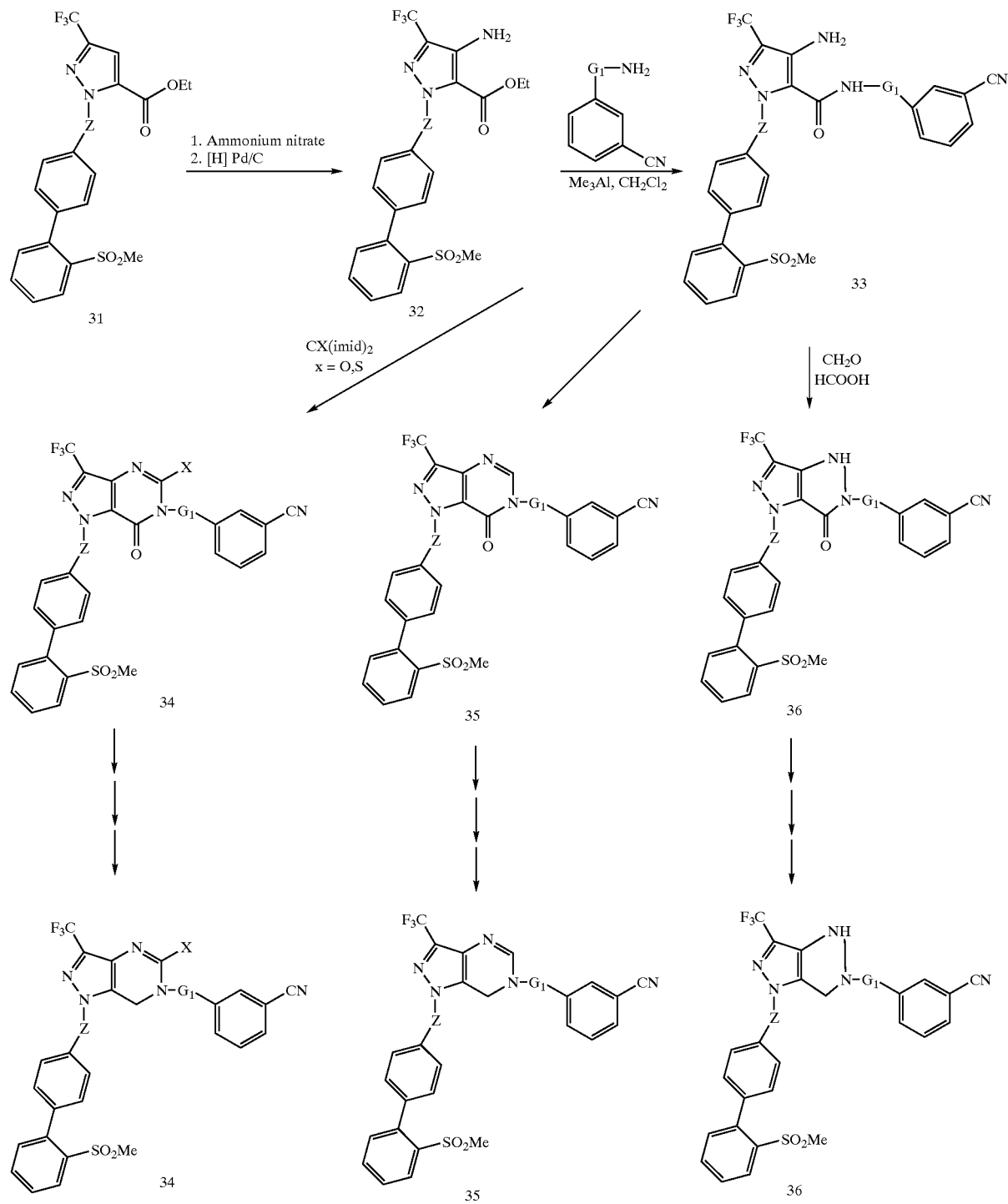

In a similar way triazole and imidazole analogs can be prepared (Scheme-13).
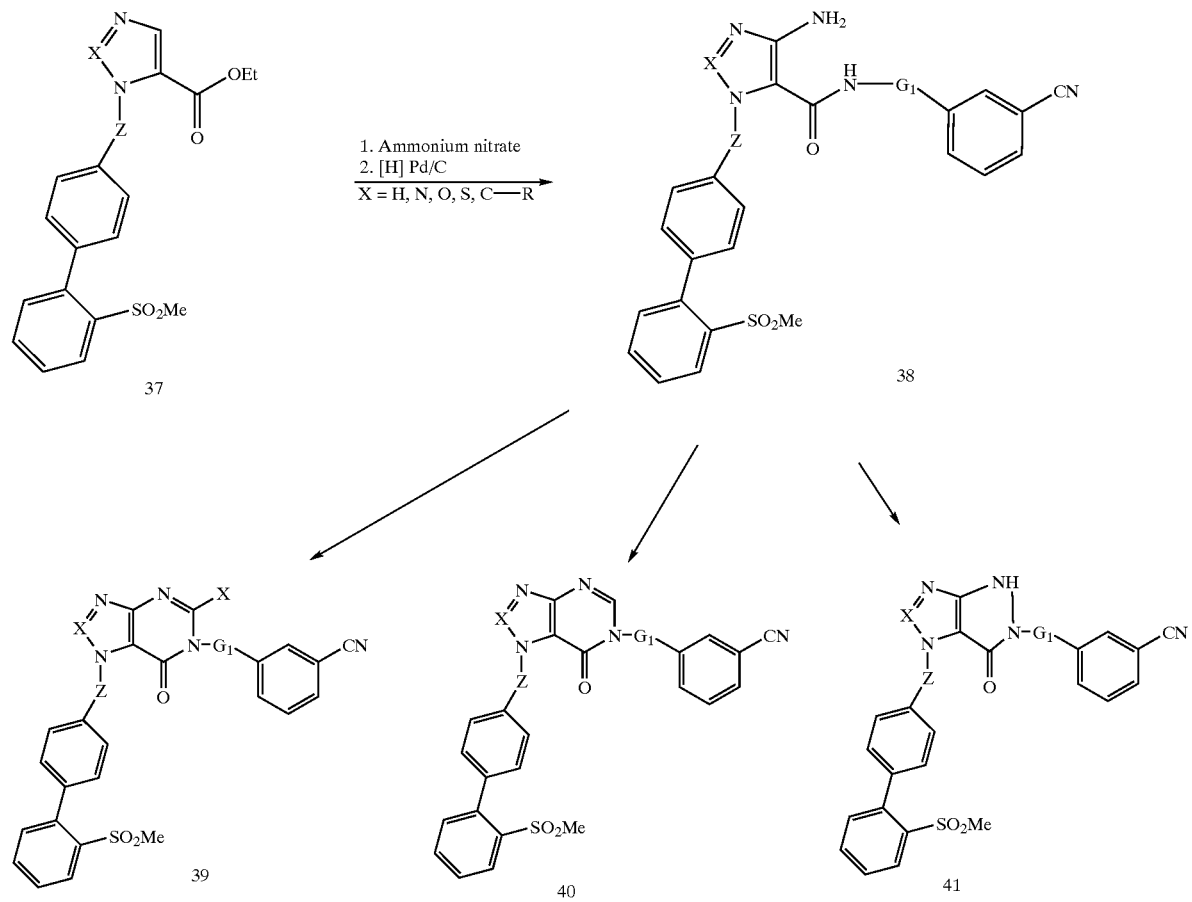
The above aza analogs can then be converted to the compounds of the present invention via methods previously described.
Des-carbonyl compounds of the present invention can be prepared via the methodologies outlined in Schemes 14–17.
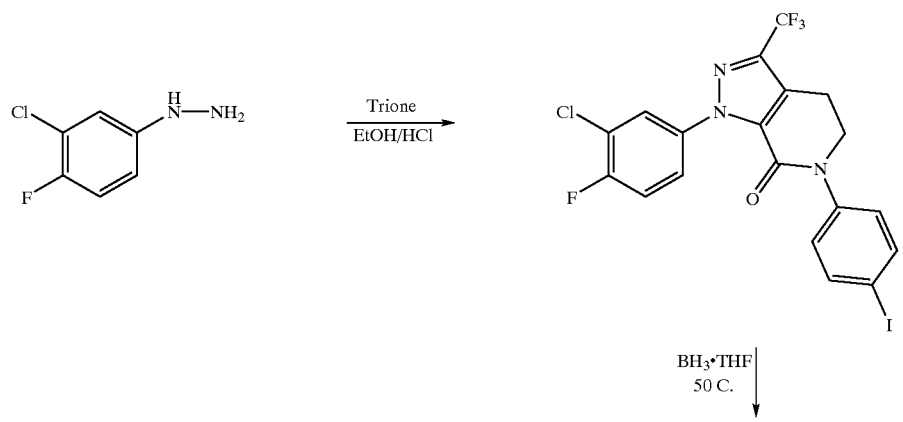

59 60
-continued
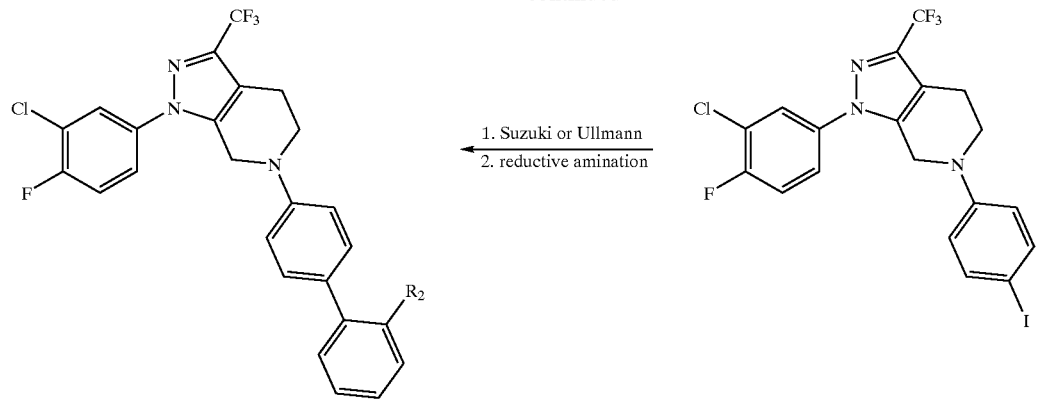
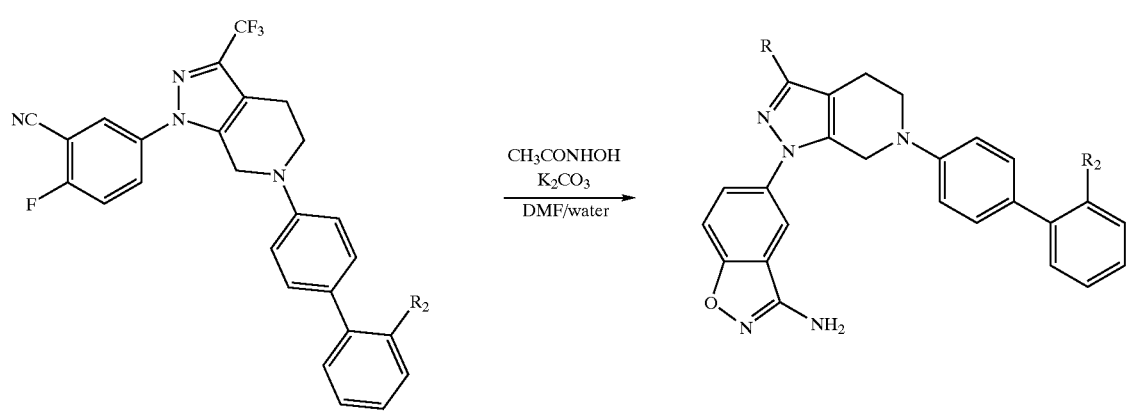
Scheme-15
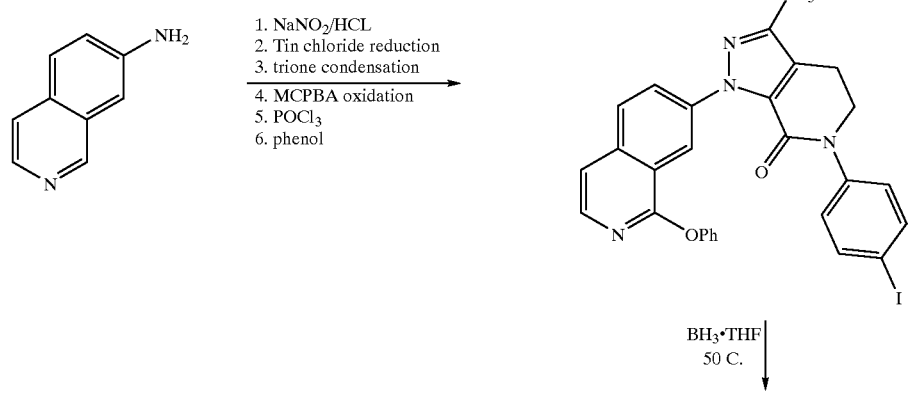

61 62
-continued
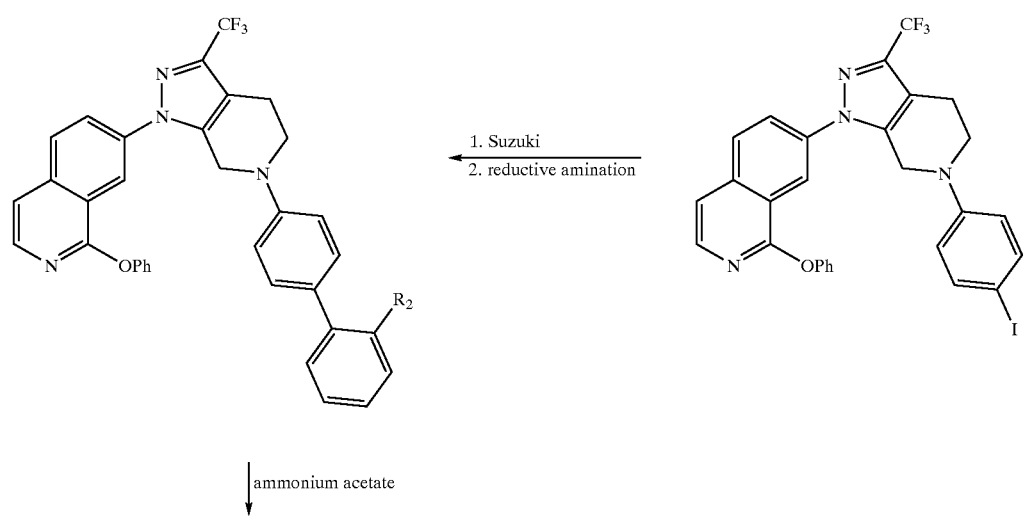
1. Suzuki
2. reductive amination
ammonium acetate
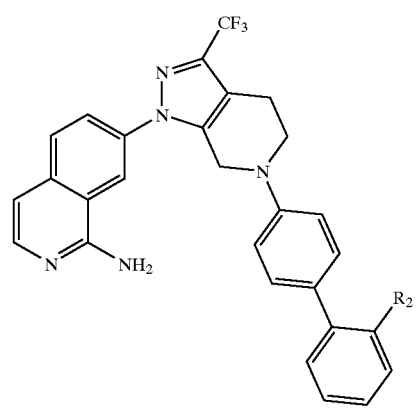
Scheme-16
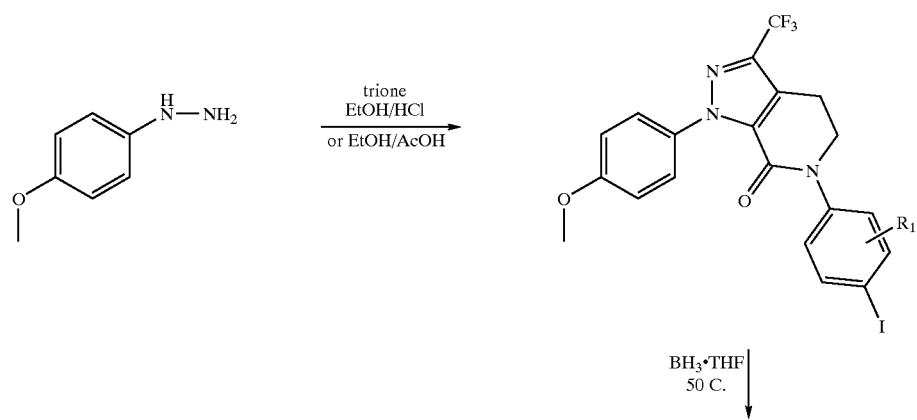
trione
EtOH/HCl
or EtOH/AcOH
BH$_3$·THF
50 C.

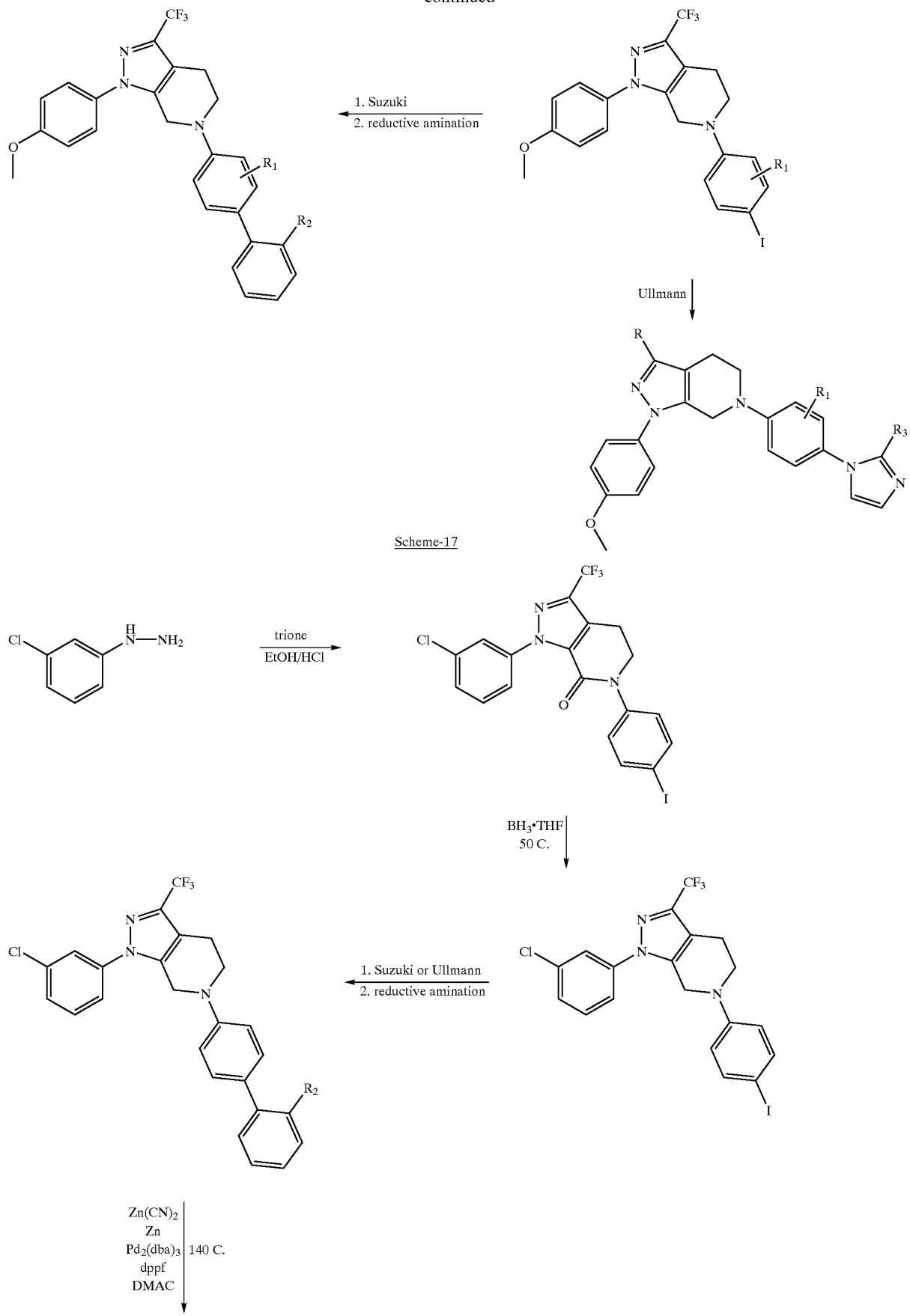

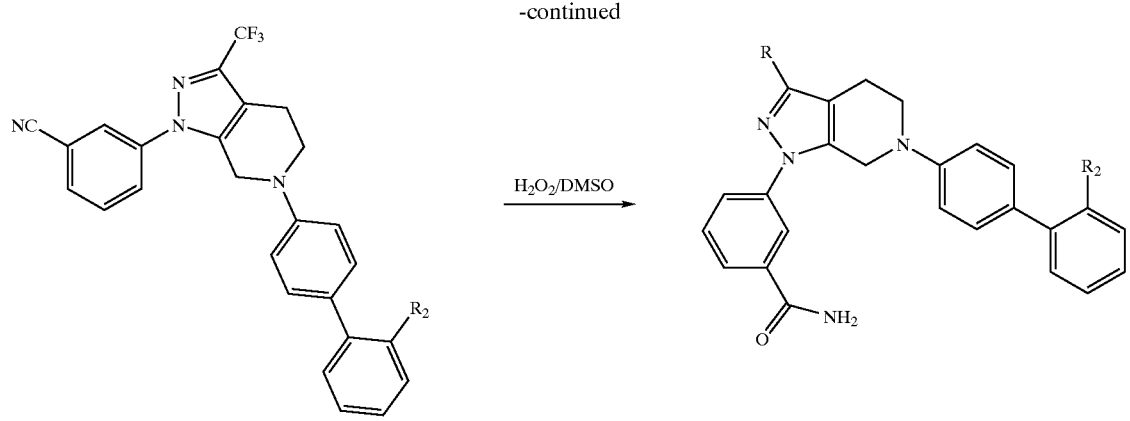
Other compounds of this invention can be obtained via the methodology outlined in Scheme-18
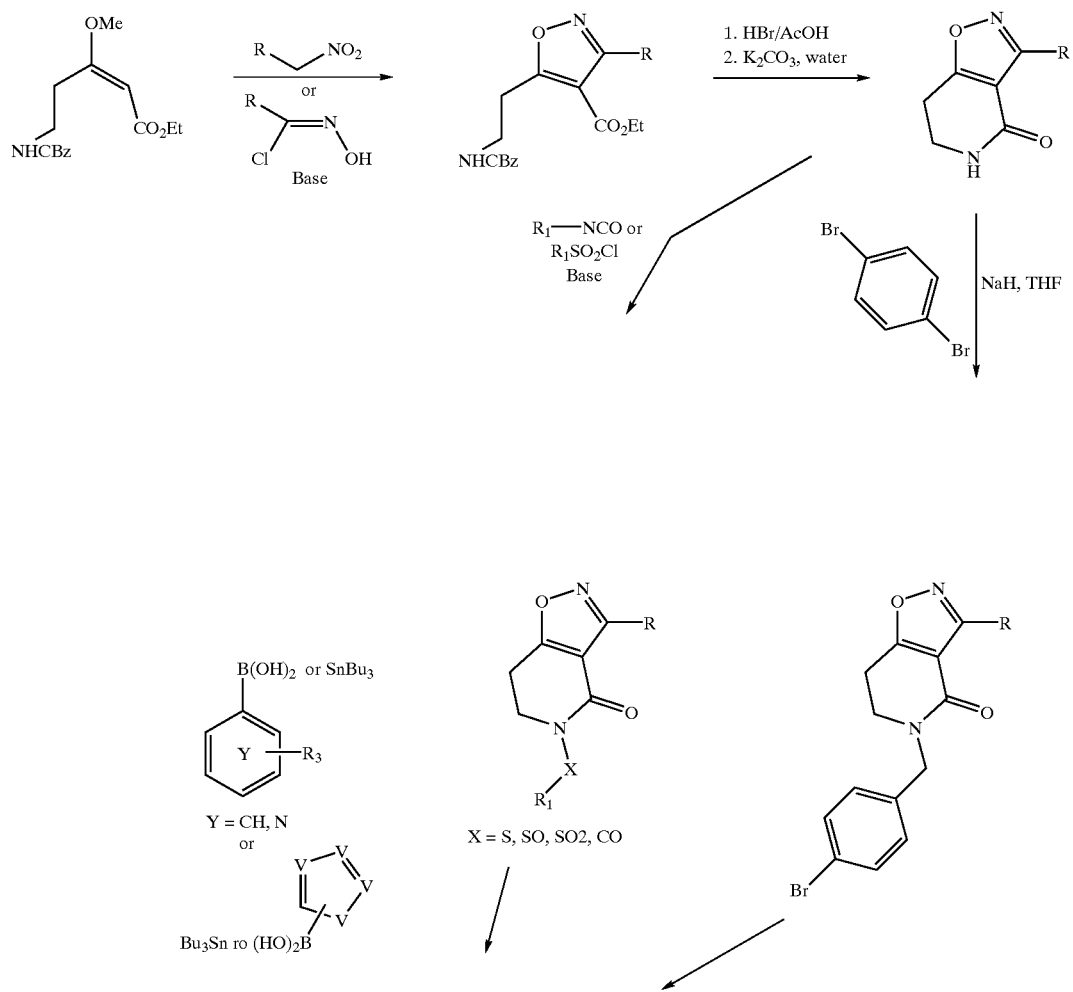

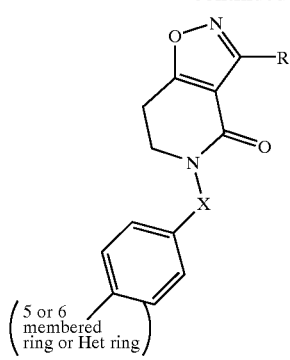
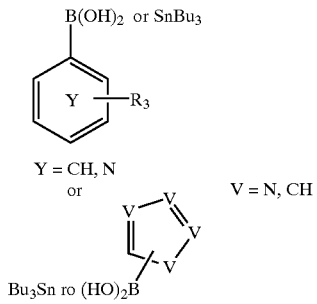

R, R3 = H, Phenyl(optionally substituted)
Ester, amido, sulfone, sulfonamido (optionally substituted), alkylamino, amino(optionally substituted), NHcarbamates, NHureas, NHsulfonamides, OH, Alkoxy(substituted), alkylalkxoy, phenoxy, Heterocyclic ring (5 or 6 membered)

The isoxazole analogs of this invention can also be converted to the pyrazole analogs via the method described in Scheme-19.

Scheme-19

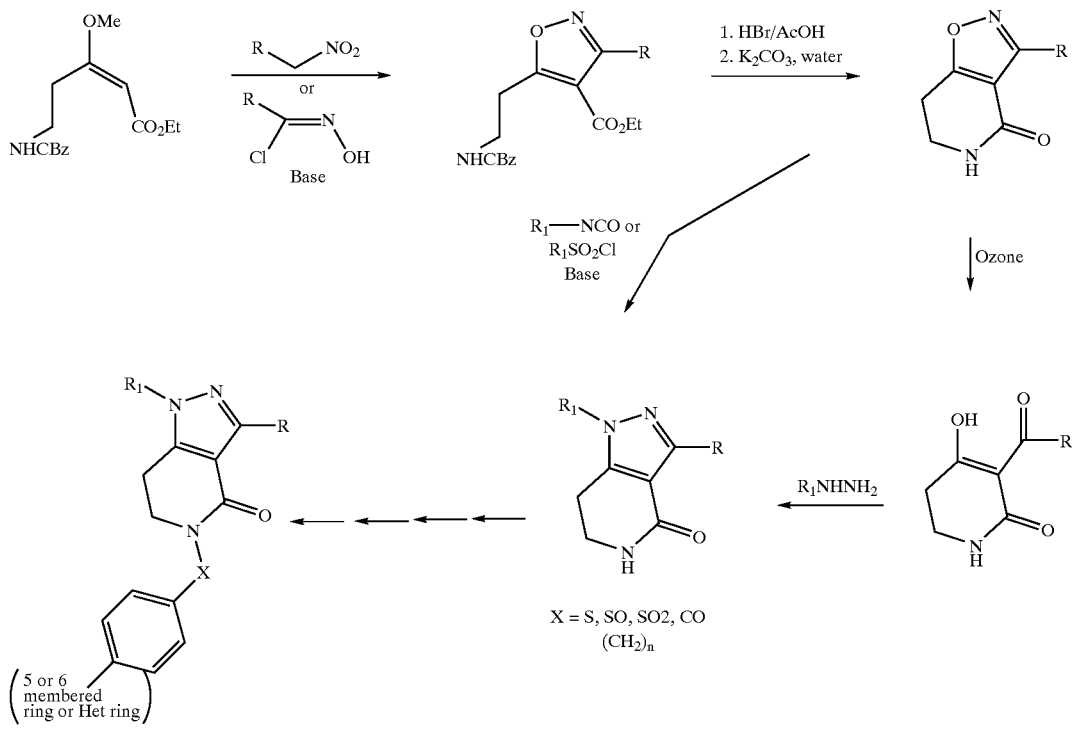

R, R3 = H, Phenyl(optionally substituted)
Ester, amido, sulfone, sulfonamido (optionally substituted), alkylamino, amino(optionally substituted), NHcarbamates, NHureas, NHsulfonamides OH, Alkoxy(substituted), alkylalkxoy, phenoxy, Heterocyclic ring (5 or 6 membered)

Furan analogs can also be obtained via the methodology of Bourzat et. al. (*Bull. Chem. Soc. Fr.* 1971, 1727) according to Scheme-20. Thiophene and pyrrole analogs can similarly be prepared. Compounds of this invention can be obtained by further elaborations of these intermediates as previously described for similar analogs.

Scheme-20
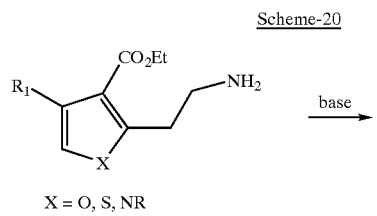
X = O, S, NR
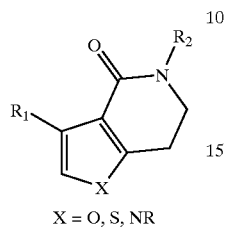
X = O, S, NR
Scheme 21 describes additional N-Pyrazole derivatives that can be obtained via the above-described methodologies.
Scheme-21
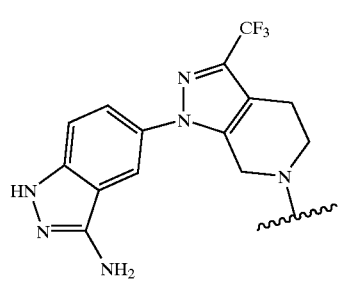
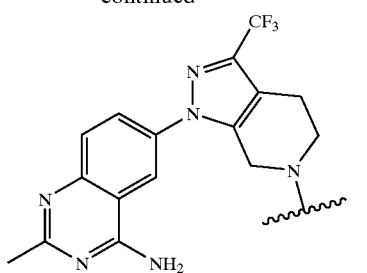
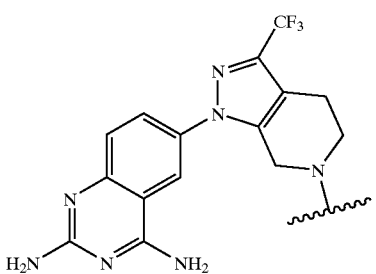
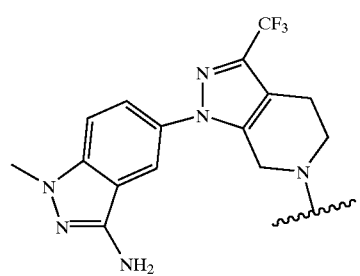
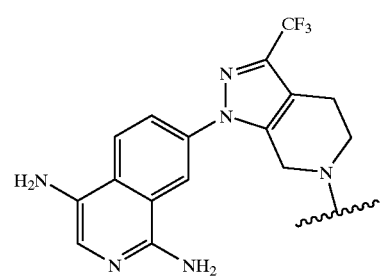
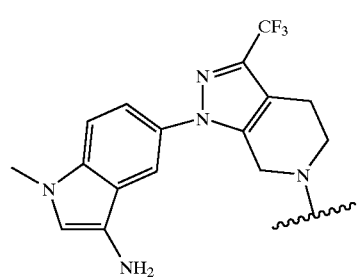
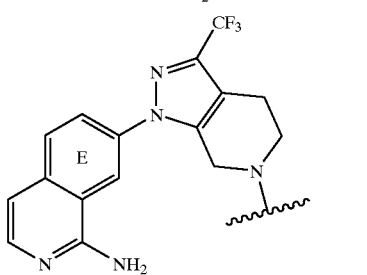
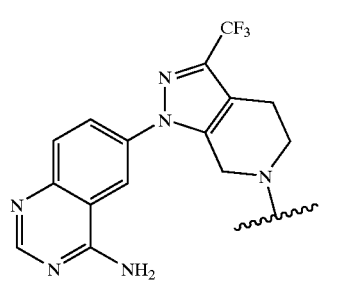

-continued
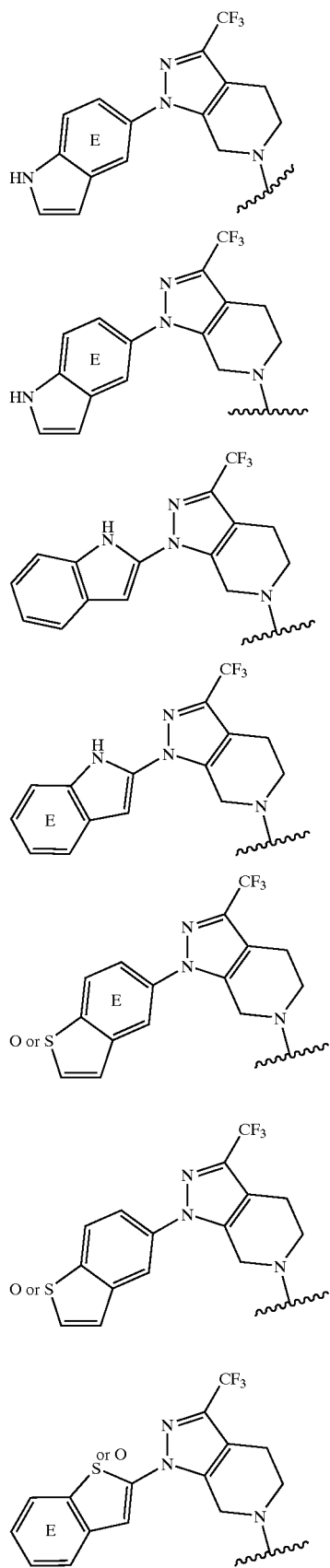
-continued
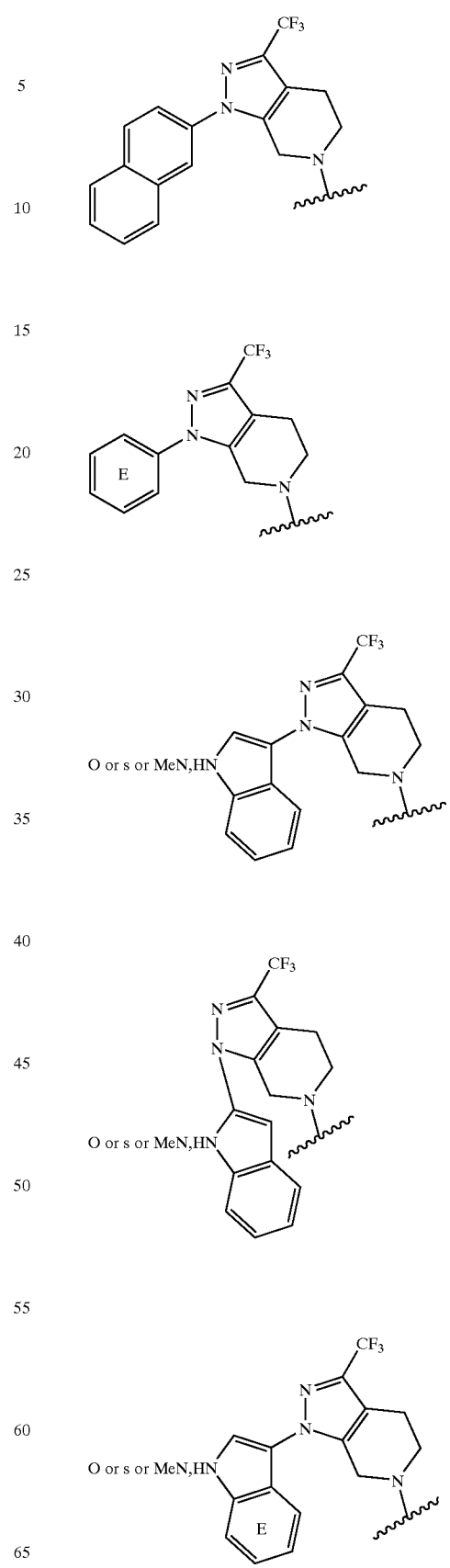

-continued
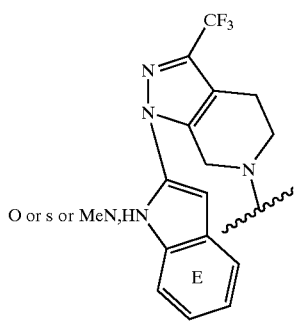
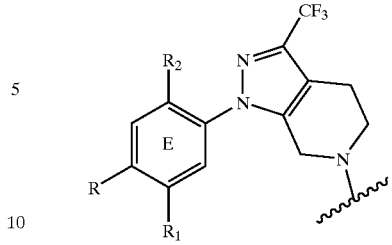
Scheme 22 describes how benzisoxazines can be prepared. Benzisothiazines could be prepared in a similar manner.
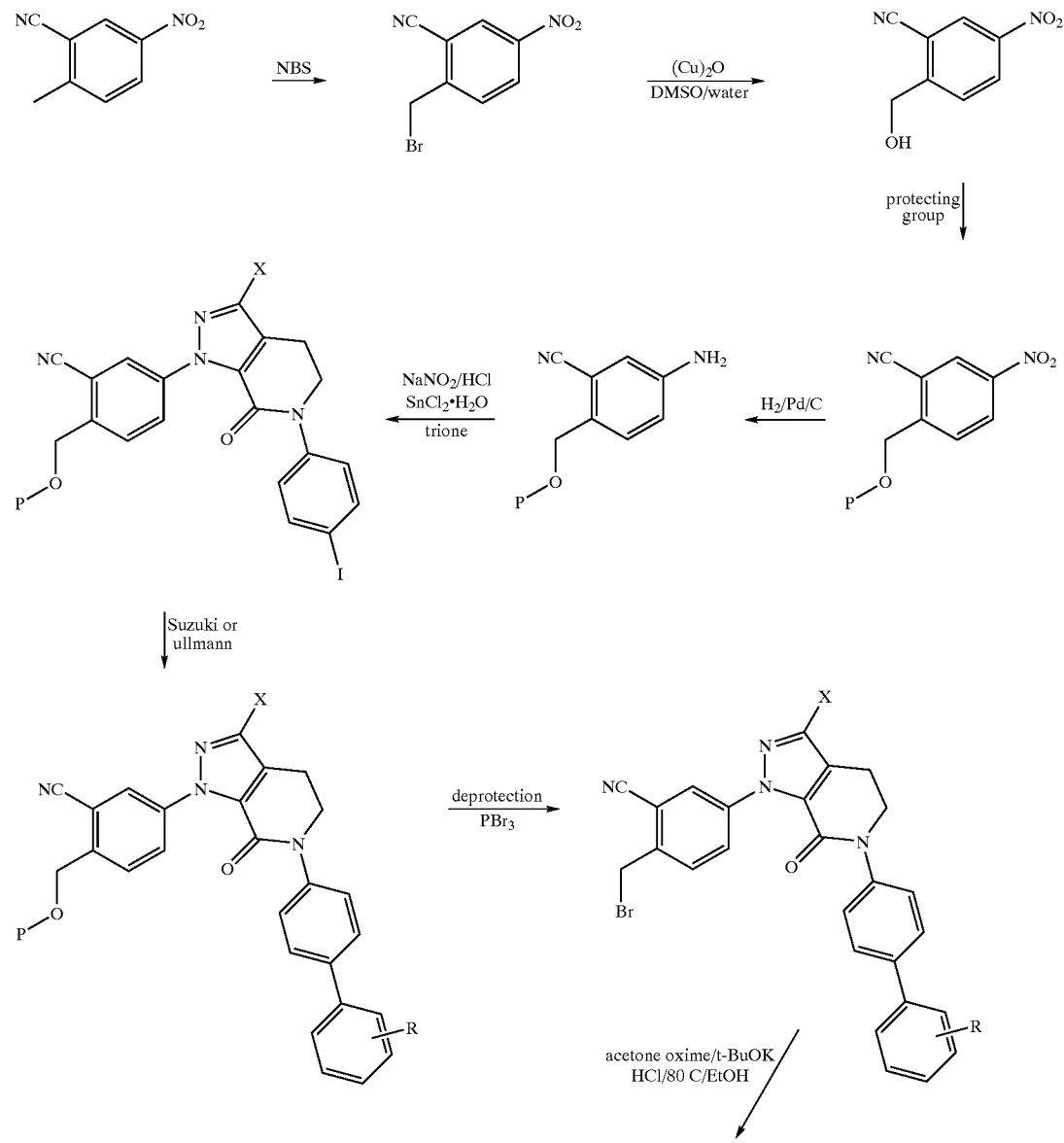

-continued

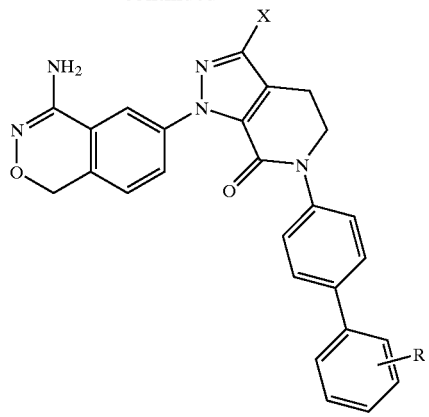

The A–B moieties can be prepared by methods known to those of skill in the art. The following publications, the contents of which are incorporated herein by reference, describe and exemplify means of preparing A–B moieties: WO97/23212, WO97/30971, WO97/38984, WO98/06694, WO98/01428, WO98/28269, WO98/28282, WO99/12903, WO98/57934, WO98/57937, WO98/57951, WO99/32454, WO99/50255, WO00/39131, WO00/38683, WO00/39102, WO01/05784, and WO00/39108.

Other features of the invention will become apparent in the course of the following descriptions of exemplary embodiments that are given for illustration of the invention and are not intended to be limiting thereof.

EXAMPLES

Example 1

6-(3-(amidino)phenyl)-1-{2'-[aminosulfonyl]-1,1'-biphenyl-4-yl}-3-methyl-7-oxo-4,5,6,7-tetrahydro-1H-pyrazolo[3,4-c]pyridine

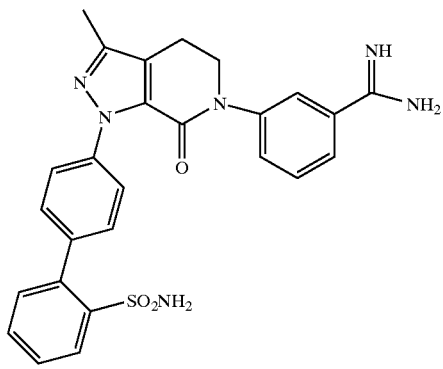

Part-A. To a DMF (50 mL) solution of 3-cyanoaniline (14.00 g, 33.88 m mol) was added sodium hydride (60% in oil, 1.36 g, 33.88 m mol). The reaction mixture was allowed to stir at room temperature for 1 h followed by the addition of 5-chloro-2-pentanone-ethylene-ketal (5.58 g, 33.88 m mol). The combined mixture was refluxed for 72 h. Quenched the reaction mixture with water (300 mL) and the organics were extracted with ethyl acetate (2×100 mL) dried and evaporated to a brown mass. Chromatography on silica gel (hexane/ethylacetate, 7:3) afforded 0.89 g of an inseparable mixture of mono and di-alkylated products. The mixture was dissolved in dichloromethane (50 mL) and to this was added triethylamine (1 mL) followed by an equivalent of ethyl oxalyl chloride. The reaction was stirred at room temperature for 18 h and then quenched with dilute hydrochloric acid (3N, 100 mL). The organics were extracted with ethyl acetate (2×100 mL) dried with magnesium sulfate and evaporated to afford 0.5 g of the desired acylated product. LRMS 347 (M+H).

Part-B. The product obtained in part-A was dissolved in dichloromethane (100 mL) and to this solution was added 3N HCL (100 mL). The mixture was stirred at room temperature for 8 h. The organics were separated, dried and evaporated to afford pure ketone compound 0.39 g. LRMS 302.

Part-C. The ketone compound from part-B was dissolved in absolute ethanol (20 mL). To this solution was added 1 equivalent of sodium ethoxide (25% in ethanol). The reaction mixture was stirred at room temperature for 3 h. Quenched the reaction with dilute hydrochloric acid (1N, 100 mL). The organics were extracted with ethyl acetate (2×50 mL), dried and evaporated to afford a pale yellow mass (0.35 g). $^1$H NMR (CDCl$_3$) δ: 6.60(m, 2H), 7.58(m, 2H), 3.88(t, 2H0, 2.81(t, 2H), 2.45(s, 3H)ppm. LRMS 257(M+H).

Part-D. The diketo-piperidone intermediate obtained in part-C (0.19 g, 0.75 m mol) was dissolved in absolute methanol (20 mL). To this was added 4-bromophenylhydrazine (0.17 g, 0.75 m mol) and the reaction was allowed to reflux overnight. Methanol was evaporated and the product was directly subjected to purification via silica gel column chromatography (hexane/ethylacetate, 7:3) to afford 0.25 g of pure pyrazole intermediate. $^1$H NMR (CDCl$_3$) δ: 7.40–7.65(m, 8H), 4.05(t, 2H), 2.92(t, 2H), 2.35(s, 3H) ppm. LRMS 409 (M+H).

Part-E. The pyrazole of part-D (0.070 g, 0.21 m mol) was dissolved in a solution of ethanol:toluene (1:1, 20 mL). To this was added ortho-t-butylsulfonamide-phenylboronic acid (0.051 g, 0.21 m mol) followed by aqueous sodium carbonate (2M, 0.3 mL) and Pd$_4$(PPh$_3$)$_4$ cat. The reaction was refluxed for 12 h, cooled, and quenched with water (50 mL). The organics were extracted with ethylacetate (2×50 mL), dried and evaporated to afford the desired pyrazole biphenylsulfonamide precursor (0.071 g). LRMS 562.5 (M+H). $^1$H NMR (CDCl$_3$) δ: 8.20(d, 1H), 7.30–7.70(m, 11H), 4.08(t, 2H0, 3.60(s, 1H0, 2.95(t, 2H), 2.40(s, 3H), 1.01(s, 9H)ppm.

Part-F. The product from part-E was dissolved in absolute methanol (50 mL) and cooled to 0° C. To this cold solution was bubbled HCl gas for 15 min. The reaction mixture was stirred at r.t. for 18 h then cooled and re-dissolved in methanol (20 mL). To this solution was added excess ammonium carbonate and the mixture was stirred for an additional 18 h. The methanol was evaporated and the residue was quenched with HCl (1N, 1mL). The crude material was then purified via reverse phase preparatory HPLC (gradient, acteonitrile/water). The desired product was obtained after lyophilization as a colorless solid. LRMS 501(M+H). HRMS found 501.170886.

Example 2

N-[1-{4-[1-(4-methoxyphenyl)-3-(trifluoromethyl)-1,4,5,7-tetrahydro-6H-pyrazolo[3,4-c]pyridin-6yl]phenyl}-1H-imidazol-2-yl)methyl]-N,N-dimethylamine

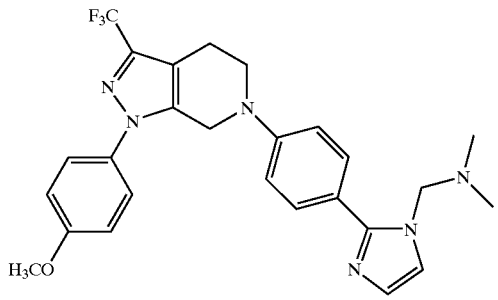

Part-A. To a solution of 4-methoxyphenyl hydrazine(1.0 g, 5.73 m mol) in ethanol(20 mL) was added acetic acid(10 mL) and trione(2.35 g, 5.73 m mol). The mixture were brought to reflux and stirred at reflux overnight, cooled to room temperature and evaporated. The crude was partitioned between ethylacetate and water, washed with water, dried over sodium sulfate, filtered and concentrated. Flash chromatography with 25% ethylacetate in hexane afforded 4-methoxy-pyrazolopyridinone intermediate (2.6 g). CI mass spectrum m/z (rel. intensity) 514 (M+H, 100).

Part-B. The above intermediate (256 mg, 0.5 m mol) was dissolved in THF (10 mL). To the solution was added borane THF complex (1 M solution, 5 mL). The reaction was stirred at 50° C. for 48 hours, partitioned between ethylacetate and water, washed with 1 N HCl and brine, dried over sodium sulfate, filtered, and concentrated to afford the des carbonyl intermediate (240 mg). CI mass spectrum m/z (rel. intensity) 500 (M+H, 100).

Part-C. The des carbonyl intermediate (80 mg) was reacted with 2-N,N-dimethylaminomethyl imidazole under regular Ullmann condition to give the desired compound A (15 mg). CI mass spectrum m/z (rel. intensity) 497 (M+H, 100). $^1$H NMR (CD$_3$OD): δ=2.77 (s, 6H) ; 2.88 (t, 2H) ; 3.79 (t, 2H); 3.88 (s, 3H); 4.29 (s, 2H); 4.52 (s, 2H); 7.13 (m; 4H); 7.37 (m, 3H); 7.52 (m, 3H).

Example 3

(3S)—N-[1-{4-[1-(4-methoxyphenyl)-3-(trifluoromethyl)-1,4,5,7-tetrahydro-6H-pyrazolo[3,4-c]pyridin-6yl]-1,1'-biphenyl-2yl}methyl-3-pyrrolidinol

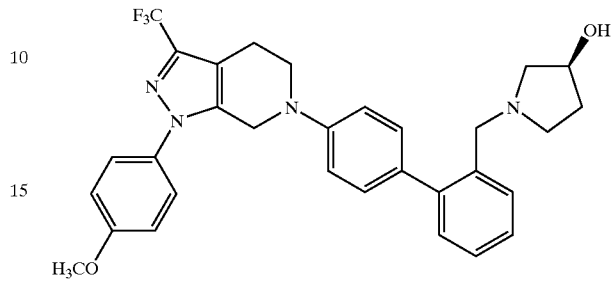

Part-A. To a solution of des carbonyl intermediate (160 mg, obtained in part B of example 2 in THF (10 mL) was added water (5 mL), sodium carbonate(102 mg), 2-formylphenylboronic acid(58 mg), and tetrakis (triphenylphosphine) palladium(0)(19 mg). The mixture were degassed under argon and stirred at reflux for 3 h. The mixture was partitioned between ethylacetate and water, washed with water and brine, dried over sodium sulfate, filtered, and concentrated. Flash chromatography with 40% ethylacetate in hexane gave the des carbonyl aldehyde intermediate(145 mg). ESI mass spectrum m/z (rel. intensity) 478 (M+H, 100).

Part-B. The above intermediate (40 mg) was dissolved in methylene chloride (10 mL), (R)-3-hydroxypyrrolidine (15 mg) was added followed by addition of sodium triacetoxyboron hydrate(15 mg). The reaction was stirred at room temperature overnight. Evaporation of the solvent followed by HPLC(RP) purification afforded the title compound (18 mg). ESI mass spectrum m/z (rel. intensity) 549 (M+H, 100).

Example 4

7-{2'-[(4-hydroxy-1-piperidinyl)methyl]-1,1'-biphenyl-4-yl}-1-(4-methoxyphenyl)-3-(trifluoromethyl)-6,7-dihydroimidazo[1,5-a]pyrazin-8(5H)-one

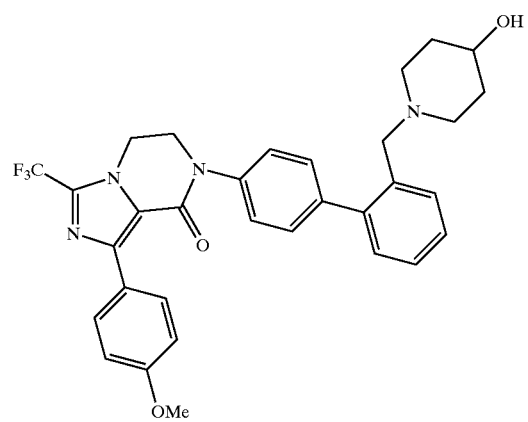

Ethyl 4-(4-methoxyphenyl)-2-(trifluoromethyl) -1H-imidazole-5-carboxylate

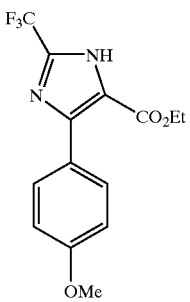

A suspension of ethyl p-methoxybenzoylacetate (16.3 mL, 85 m mol) and SeO$_2$ (9.9 g, 89 m mol) in 80 mL of dioxane was heated to reflux overnight. After being cooled down to rt, the reaction mixture was filtered to remove inorganic solid. The filtrate was concentrated under reduced pressure and treated with benzene. The benzene solution was concentrated to dryness under reduced pressure to yield ethyl 2,3-dioxo-(p-methoxyphenyl) -propionate, which was used in next step without further purification.

To a slurry of NH$_4$OAc (50 g, 651 m mol) in 170 mL of acetic acid was added the above tricarbonyl compound (15.5 g, 65.1 m mol) followed by trifluoroacetaldehyde hemiethyl acetal (16.8 mL, 130 m mol). The mixture was heated to 65° C. and stirred for 3 h. The solution was cooled to rt and the acetic acid was evaporated to give an oily residue. This residue was dissolved in ethyl acetate and washed with sat. NaHCO$_3$, water, and brine. The organic phase was then dried (Na$_2$SO$_4$), filtered, and concentrated. Silica gel chromatography provided the corresponding imidazole compound (10.9 g, 53% in 2 steps). $^1$H NMR (CDCl$_3$): δ 7.58 (2H, d, J=8.8 Hz), 6.85 (2H, d, J=8.8 Hz), 4.08 (2H, q, J=7.3 Hz), 3.78 (3H, s), 1.23 (1H, t, J=7.3 Hz) ppm. $^{19}$F NMR (CDCl3) δ -64.19 ppm. ESI MS: m/z 315 (ES+), 313 (ES-)

N-(4-bromophenyl)-N-(2-hydroxyethyl)-4-(4-methoxyphenyl)-2-(trifuoromethyl)-1H-imidazole-5-carboxamide

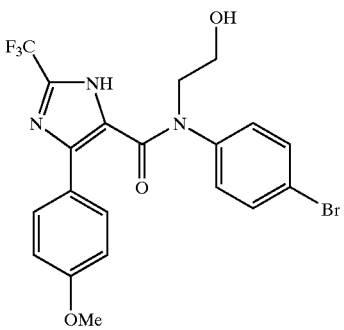

A mixture of the imidazole ethyl ester (9.27 g, 29.5 m mol) and LiOH (8.0 g) in MeOH—H$_2$O (150 mL, 2:1) was stirred at rt overnight. After removing most of the MeOH under reduced pressure, the mixture was neutralized with aq. HCl and extracted with EtOAc. The combined organic layers were dried over MgSO$_4$, filtered, concentrated to dry, and used directly in next step. ESI MS: m/z 285 (ES-).

The imidazole acid (7.6 g, 26.55 m mol) in 100 mL of methylene chloride was treated with oxalyl chloride (6.98 mL, 79.65 m mol), followed by a catalytic amount of DMF. After stirring overnight at rt, the reaction mixture was concentrated to dry under reduced pressure and exposed to high vacuum to provide the corresponding acid chloride.

A mixture of p-bromoaniline (17.2 g, 100 m mol) and bromoethanol (3.54 mL, 50 m mol) in a 50 mL round bottle was heated gradually to 70° C. and then was stirred at 70° C. overnight. The reaction mixture was then cooled, basified with aq. NaOH, and extracted with ether. The ether layers were dried over Na$_2$SO$_4$ and concentrated to near dryness. N-β-hydroxyethyl-p-bromoaniline was obtained as a crystalline material (5.1 g, 47%). $^1$H NMR (CDCl$_3$): δ 7.28 (2H, d, J=8.8 Hz), 6.60 (2H, d, J=8.8 Hz), 3.86 (2H, t, J=5.1 Hz), 3.29 (2H, t, J=5.1 Hz), 3.00 (2H, br s) ppm.

To N-β-hydroxyethyl-p-bromoaniline (5.1 g, 23.6 m mol) in 100 mL of benzene was added 200 mL of 1N NaOH, followed by the crude acid chloride (~23.6 m mol) made above. The resulted mixture was stirred at rt for 1 h. The benzene layer was separated. The water layer was extracted with ethyl acetate. The combined organic layers were dried over Na$_2$SO$_4$, concentrated, and applied to silica gel chromatography to generate the imidazole amide compound (1.71 g, 15% in 3 steps). APCI MS: m/z 484, 486 (AP$^+$), 482, 484 (AP$^-$).

7-(4-bromophenyl)-1-(4-methoxyphenyl)-3-(trifluoromethyl)-6,7-dihydroimidazo[1,5-a]pyrazin-8(5H)-one

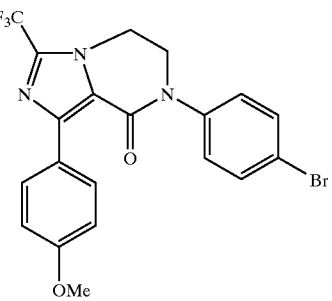

To a solution of the imidazole amide (0.78 g, 1.61 m mol) in 20 mL of methylene chloride was added PBr$_3$ (0.46 mL, 4.83 m mol) dropwise. The resulting reaction mixture was stirred at rt for 30 min, then quenched at 0° C. with aq. Na$_2$CO$_3$ and extracted with methylene chloride. The combined organic layers were dried over MgSO$_4$ and concentrated to dryness. The resulting imidazole bromide compound was used directly in next step.

The crude imidazole bromide compound was dissolved in 6 mL of DMF. To this solution, sodium hydride (129 mg, 60%, 3.22 m mol) was added at 0° C. under nitrogen atmosphere. The reaction was stirred at rt overnight, then quenched with water at 0° C., and extracted with ethyl acetate. The extracts were washed with water, brine, dried (Na$_2$SO$_4$), and concentrated to dryness. The residue was applied to silica gel chromatography to afford the bicyclic core compound (503 mg, 67% in 2 steps). APCI MS: m/z 466, 468 (AP$^+$), 464, 466 (AP$^-$)

7-{2'-[(4-hydroxy-1-piperidinyl)methyl]-1,1'-biphenyl-4-yl}-1-(4-methoxyphenyl)-3-(trifluoromethyl)-6,7-dihydroimidazo[1,5-a]pyrazin-8(5H)-one A mixture of the bicyclic bromide (150 mg, 0.322 m mol), 2-formylbenzene-boronic acid (58 mg), and K$_3$PO$_4$ (226 mg) in 10 mL of dioxane was degassed with nitrogen for 10 min. To the mixture, Pd(PPh$_3$)$_4$ (18 mg) was added. The reaction mixture was heated to reflux overnight, under nitrogen. After removal of dioxane under reduced pressure, the residue was diluted with water and extracted with methylene chloride. The combined organic layers were dried (Na$_2$SO$_4$), purified by silica gel chromatography to yield the biphenyl compound (120 mg, 71%). $^{19}$F NMR (CDCL3): δ −60.25 ppm. ESI MS: m/z 492 (ES$^+$), 490 (ES$^-$).

To a solution of biphenyl aldehyde (10 mg, 0.0203 m mol) in 5 mL of methanol, NaBH$_4$ (1.6 mg, 0.0407 m mol) was added at 0° under nitrogen. The reaction mixture was stirred at rt for 15 min. After quenching with aq. NaHCO$_3$, the mixture was extracted with methylene chloride, dried (MgSO$_4$), and concentrated to dryness. The crude material was used directly in next step. APCI MS: m/z 494 (AP$^+$), 492 (AP$^-$).

The crude alcohol made above was treated with PBr$_3$ (0.006 mL, 0.0407 m mol) at rt for 30 min. The reaction was quenched with aq. NaHCO$_3$, extracted with methylene chloride, dried, and concentrated to dryness. The crude bromide was used directly in next step.

To a solution of the crude bromide in 5 mL of acetonitrile was added hydroxypiperidine HCl salt (14 mg, 0.102 m mol) and 0.04 mL of i-Pr$_2$Net. The reaction mixture was stirred at rt overnight, diluted with water, and extracted with methylene chloride. The extracts were combined, dried (Na$_2$SO$_4$), and concentrated to dryness. The residue was dissolved in 4 mL of acetonitrile/water (1:1) mixture, applied to preparative RP-HPLC to afford the title compound as a bis-TFA salt (9.4 mg, 58% in 3 steps). $^1$H NMR (CD$_3$OD): δ 7.71 (5H, m) 7.53 (2H, m), 7.40 (1H, m), 7.32 (2H, d, J.=8.9 Hz), 6.96 (2H, d, J =8.9 Hz), 5.64 (2H, m), 4.79 (2H, m), 4.38 (2H, s), 3.79 (3H, s), 3.62 (1H, m), 3.02 (2H, m), 2.71 (2H, m), 1.95~1.60 (4H, m) ppm. $^{19}$F NMR (CD$_3$OD): δ−62.88, −77.50 ppm. ESI MS: m/z 577 (ES$^+$).

The following tables contain representative examples of the present invention. Each entry in each table is intended to be paired with each formula at the start of the table. For example, in Tables 1 and 2, example 1 is intended to be paired with each of the formulae.

The following nomenclature is intended for group A in the following tables.

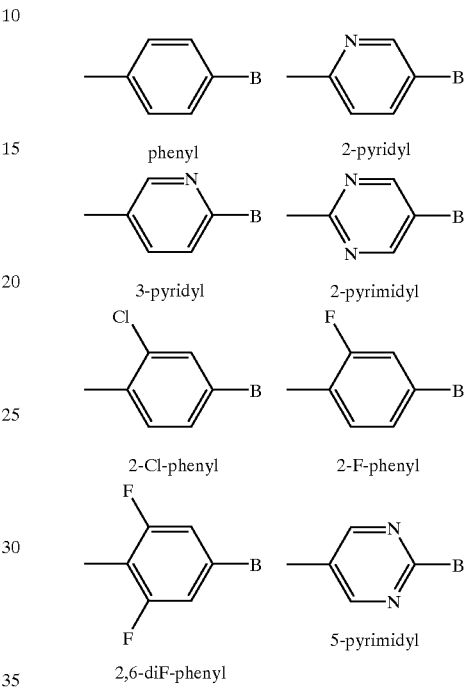

phenyl  2-pyridyl
3-pyridyl  2-pyrimidyl
2-Cl-phenyl  2-F-phenyl
2,6-diF-phenyl  5-pyrimidyl

TABLE 1

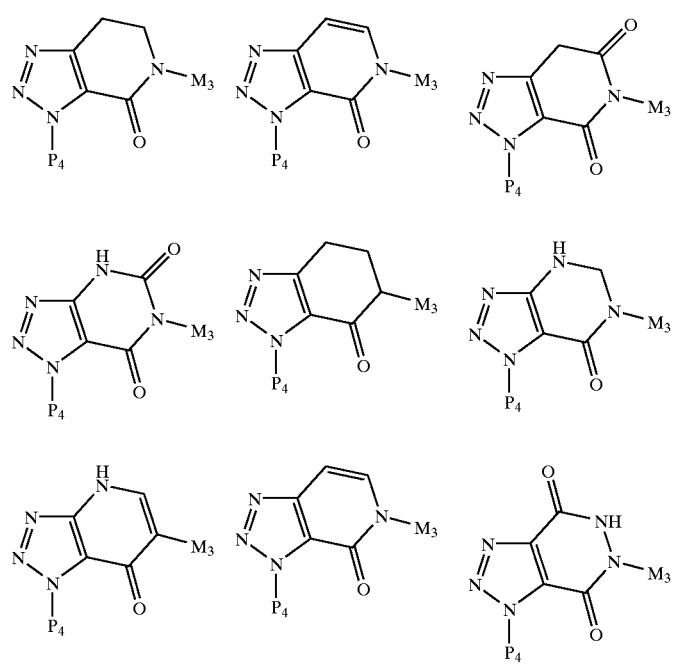

TABLE 1-continued
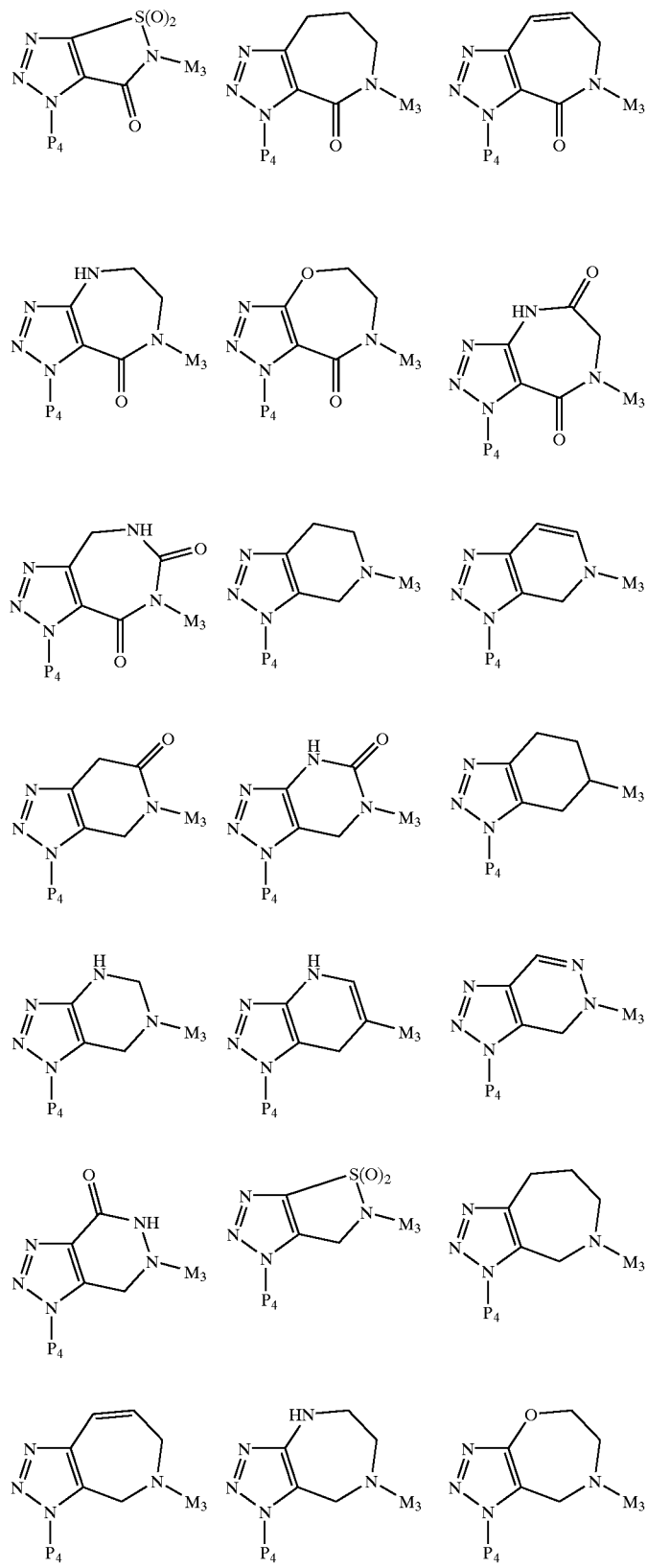

TABLE 1-continued

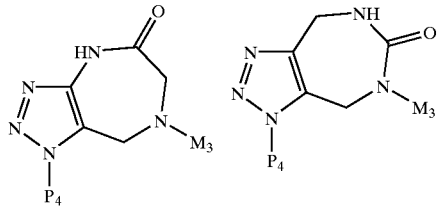

P$_4$ is Z-A-B, wherein Z is a bond;
M3 is -G$_1$-G, wherein G$_1$ is a bond;
G is 4-(methoxy)phenyl;

Ex# A B 1. phenyl 2-(NH$_2$SO$_2$)phenyl
2. phenyl 2-(CH$_3$SO$_2$)phenyl
3. phenyl 3-NH$_2$SO$_{2-4}$-pyridyl
4. phenyl 3-CH$_3$SO$_{2-4}$-pyridyl
5. phenyl 2-(CH$_3$NH)phenyl
6. phenyl 3-((CH$_3$)$_2$NCH$_2$)-4-pyridyl
7. phenyl 2-(N-(3-R—HO-pyrrolidinyl)CH$_2$)phenyl
8. phenyl 2-(N-(4-HO-piperidinyl)CH$_2$)phenyl
9. phenyl 2-((CH$_3$)$_2$NCH$_2$)phenyl
10. phenyl 2-((CH$_3$)NHCH$_2$)phenyl
11. phenyl 2-((CH$_3$CH$_2$)NHCH$_2$)phenyl
12. phenyl 2-((CH$_3$CH$_2$)$_2$NCH$_2$)phenyl
13. phenyl 2-((CH$_3$CH$_2$)N(CH$_3$)CH$_2$)phenyl
14. phenyl 2-(((CH$_3$)$_2$CH)NHCH$_2$)phenyl
15. phenyl 2-(((CH$_3$)$_2$CH)$_2$NCH$_2$)phenyl
16. phenyl 2-((cyclopropyl)NHCH$_2$)phenyl
17. phenyl 2-((cyclopropyl)$_2$NCH$_2$)phenyl
18. phenyl 2-((cyclobutyl)NHCH$_2$)phenyl
19. phenyl 2-((cyclobutyl)$_2$NCH$_2$)phenyl
20. phenyl 2-((cyclopentyl)NHCH$_2$)phenyl
21. phenyl 2-((cyclopentyl)$_2$NCH$_2$)phenyl
22. phenyl 2-((cyclohexyl)NHCH$_2$)phenyl
23. phenyl 2-((cyclohexyl)$_2$NCH$_2$)phenyl
24. phenyl 1-CH$_{3-2}$-imidazolyl
25. phenyl 2-CH$_{3-1}$-imidazolyl
26. phenyl 2-((CH$_3$)$_2$NCH$_2$)-1-imidazolyl
27. phenyl 2-((CH$_3$)NHCH$_2$)-1-imidazolyl
28. phenyl 2-((CH$_3$CH$_2$)NHCH$_2$)-1-imidazolyl
29. phenyl 2-((CH$_3$CH$_2$)$_2$NCH$_2$)-1-imidazolyl
30. phenyl 2-((CH$_3$CH$_2$)N(CH$_3$)CH$_2$)-1-imidazolyl
31. phenyl 2-(((CH$_3$)$_2$CH)NHCH$_2$)-1-imidazolyl
32. phenyl 2-(((CH$_3$)$_2$CH)$_2$NCH$_2$)-1-imidazolyl
33. phenyl 2-((cyclopropyl)NHCH$_2$)-1-imidazolyl
34. phenyl 2-((cyclopropyl)$_2$NCH$_2$)-1-imidazolyl
35. phenyl 2-((cyclobutyl)NHCH$_2$)-1-imidazolyl
36. phenyl 2-((cyclobutyl)$_2$NCH$_2$)-1-imidazolyl
37. phenyl 2-((cyclopentyl)NHCH$_2$)-1-imidazolyl
37. phenyl 2-((cyclopentyl)$_2$NCH$_2$)-1-imidazolyl
39. phenyl 2-((cyclohexyl)NHCH$_2$)-1-imidazolyl
40. phenyl 2-((cyclohexyl)$_2$NCH$_2$)-1-imidazolyl
41. 2-pyridyl 2-(NH$_2$SO$_2$)phenyl
42. 2-pyridyl 2-(CH$_3$SO$_2$)phenyl
43. 2-pyridyl 3-NH$_2$SO$_{2-4}$-pyridyl
44. 2-pyridyl 3-CH$_3$SO$_{2-4}$-pyridyl
45. 2-pyridyl 2-(CH$_3$NH)phenyl
46. 2-pyridyl 3-((CH$_3$)$_2$NCH$_2$)-4-pyridyl
47. 2-pyridyl 2-(N-(3-R—HO-pyrrolidinyl)CH$_2$)phenyl
48. 2-pyridyl 2-(N-(4-HO-piperidinyl)CH$_2$)phenyl
49. 2-pyridyl 2-((CH$_3$)$_2$NCH$_2$)phenyl
50. 2-pyridyl 2-((CH$_3$)NHCH$_2$)phenyl
51. 2-pyridyl 2-((CH$_3$CH$_2$)NHCH$_2$)phenyl
52. 2-pyridyl 2-((CH$_3$CH$_2$)$_2$NCH$_2$)phenyl
53. 2-pyridyl 2-((CH$_3$CH$_2$)N(CH$_3$)CH$_2$)phenyl
54. 2-pyridyl 2-(((CH$_3$)$_2$CH)NHCH$_2$)phenyl
55. 2-pyridyl 2-(((CH$_3$)$_2$CH)$_2$NCH$_2$)phenyl
56. 2-pyridyl 2-((cyclopropyl)NHCH$_2$)phenyl
57. 2-pyridyl 2-((cyclopropyl)$_2$NCH$_2$)phenyl
58. 2-pyridyl 2-((cyclobutyl)NHCH$_2$)phenyl
59. 2-pyridyl 2-((cyclobutyl)$_2$NCH$_2$)phenyl
60. 2-pyridyl 2-((cyclopentyl)NHCH$_2$)phenyl
61. 2-pyridyl 2-((cyclopentyl)$_2$NCH$_2$)phenyl
62. 2-pyridyl 2-((cyclohexyl)NHCH$_2$)phenyl
63. 2-pyridyl 2-((cyclohexyl)$_2$NCH$_2$)phenyl
64. 2-pyridyl 1-CH$_{3-2}$-imidazolyl
65. 2-pyridyl 2-CH$_{3-1}$-imidazolyl
66. 2-pyridyl 2-((CH$_3$)$_2$NCH$_2$)-1-imidazolyl
67. 2-pyridyl 2-((CH$_3$)NHCH$_2$)-1-imidazolyl
68. 2-pyridyl 2-((CH$_3$CH$_2$)NHCH$_2$)-1-imidazolyl
69. 2-pyridyl 2-((CH$_3$CH$_2$)$_2$NCH$_2$)-1-imidazolyl
70. 2-pyridyl 2-((CH$_3$CH$_2$)N(CH$_3$)CH$_2$)-1-imidazolyl
71. 2-pyridyl 2-(((CH$_3$)$_2$CH)NHCH$_2$)-1-imidazolyl
72. 2-pyridyl 2-(((CH$_3$)$_2$CH)$_2$NCH$_2$)-1-imidazolyl
73. 2-pyridyl 2-((cyclopropyl)NHCH$_2$)-1-imidazolyl
74. 2-pyridyl 2-((cyclopropyl)$_2$NCH$_2$)-1-imidazolyl
75. 2-pyridyl 2-((cyclobutyl)NHCH$_2$)-1-imidazolyl
76. 2-pyridyl 2-((cyclobutyl)$_2$NCH$_2$)-1-imidazolyl
77. 2-pyridyl 2-((cyclopentyl)NHCH$_2$)-1-imidazolyl
78. 2-pyridyl 2-((cyclopentyl)$_2$NCH$_2$)-1-imidazolyl
79. 2-pyridyl 2-((cyclohexyl)NHCH$_2$)-1-imidazolyl
80. 2-pyridyl 2-((cyclohexyl)$_2$NCH$_2$)-1-imidazolyl
81. 3-pyridyl 2-(NH$_2$SO$_2$)phenyl
82. 3-pyridyl 2-(CH$_3$SO$_2$)phenyl
83. 3-pyridyl 3-NH$_2$SO$_{2-4}$-pyridyl
84. 3-pyridyl 3-CH$_3$SO$_{2-4}$-pyridyl
85. 3-pyridyl 2-(CH$_3$NH)phenyl
86. 3-pyridyl 3-((CH$_3$)$_2$NCH$_2$)-4-pyridyl
87. 3-pyridyl 2-(N-(3-R—HO-pyrrolidinyl)CH$_2$)phenyl
88. 3-pyridyl 2-(N-(4-HO-piperidinyl)CH$_2$)phenyl
89. 3-pyridyl 2-((CH$_3$)$_2$NCH$_2$)phenyl
90. 3-pyridyl 2-((CH$_3$)NHCH$_2$)phenyl
91. 3-pyridyl 2-((CH$_3$CH$_2$)NHCH$_2$)phenyl
92. 3-pyridyl 2-((CH$_3$CH$_2$)$_2$NCH$_2$)phenyl
93. 3-pyridyl 2-((CH$_3$CH$_2$)N(CH$_3$)CH$_2$)phenyl
94. 3-pyridyl 2-(((CH$_3$)$_2$CH)NHCH$_2$)phenyl
95. 3-pyridyl 2-(((CH$_3$)$_2$CH)$_2$NCH$_2$)phenyl
96. 3-pyridyl 2-((cyclopropyl)NHCH$_2$)phenyl
97. 3-pyridyl 2-((cyclopropyl)$_2$NCH$_2$)phenyl
98. 3-pyridyl 2-((cyclobutyl)NHCH$_2$)phenyl
99. 3-pyridyl 2-((cyclobutyl)$_2$NCH$_2$)phenyl
100. 3-pyridyl 2-((cyclopentyl)NHCH$_2$)phenyl
101. 3-pyridyl 2-((cyclopentyl)$_2$NCH$_2$)phenyl
102. 3-pyridyl 2-((cyclohexyl)NHCH$_2$)phenyl
103. 3-pyridyl 2-((cyclohexyl)$_2$NCH$_2$)phenyl 104. 3-pyridyl 1-$CH_{3-2}$-imidazolyl
105. 3-pyridyl 2-$CH_{3-1}$-imidazolyl
106. 3-pyridyl 2-(($CH_3)_2NCH_2$)-1-imidazolyl
107. 3-pyridyl 2-(($CH_3)NHCH_2$)-1-imidazolyl
108. 3-pyridyl 2-(($CH_3CH_2)NHCH_2$)-1-imidazolyl
109. 3-pyridyl 2-(($CH_3CH_2)_2NCH_2$)-1-imidazolyl
110. 3-pyridyl 2-(($CH_3CH_2)N(CH_3)CH_2$)-1-imidazolyl
111. 3-pyridyl 2-((($CH_3)_2CH)NHCH_2$)-1-imidazolyl
112. 3-pyridyl 2-((($CH_3)_2CH)_2NCH_2$)-1-imidazolyl
113. 3-pyridyl 2-((cyclopropyl)$NHCH_2$)-1-imidazolyl
114. 3-pyridyl 2-((cyclopropyl)$_2NCH_2$)-1-imidazolyl
115. 3-pyridyl 2-((cyclobutyl)$NHCH_2$)-1-imidazolyl
116. 3-pyridyl 2-((cyclobutyl)$_2NCH_2$)-1-imidazolyl
117. 3-pyridyl 2-((cyclopentyl)$NHCH_2$)-1-imidazolyl
118. 3-pyridyl 2-((cyclopentyl)$_2NCH_2$)-1-imidazolyl
119. 3-pyridyl 2-((cyclohexyl)$NHCH_2$)-1-imidazolyl
120. 3-pyridyl 2-((cyclohexyl)$_2NCH_2$)-1-imidazolyl
121. 2-pyrimidyl 2-($NH_2SO_2$)phenyl
122. 2-pyrimidyl 2-($CH_3SO_2$)phenyl
123. 2-pyrimidyl 3-$NH_2SO_{2-4}$-pyridyl
124. 2-pyrimidyl 3-$CH_3SO_{2-4}$-pyridyl
125. 2-pyrimidyl 2-($CH_3NH$)phenyl
126. 2-pyrimidyl 3-(($CH_3)_2NCH_2$)-4-pyridyl
127. 2-pyrimidyl 2-(N-(3-R—HO-pyrrolidinyl)$CH_2$)phenyl
128. 2-pyrimidyl 2-(N-(4-HO-piperidinyl)$CH_2$)phenyl
129. 2-pyrimidyl 2-(($CH_3)_2NCH_2$)phenyl
130. 2-pyrimidyl 2-(($CH_3)NHCH_2$)phenyl
131. 2-pyrimidyl 2-(($CH_3CH_2)NHCH_2$)phenyl
132. 2-pyrimidyl 2-(($CH_3CH_2)_2NCH_2$)phenyl
133. 2-pyrimidyl 2-(($CH_3CH_2)N(CH_3)CH_2$)phenyl
134. 2-pyrimidyl 2-((($CH_3)_2CH)NHCH_2$)phenyl
135. 2-pyrimidyl 2-((($CH_3)_2CH)_2NCH_2$)phenyl
136. 2-pyrimidyl 2-((cyclopropyl)$NHCH_2$)phenyl
137. 2-pyrimidyl 2-((cyclopropyl)$_2NCH_2$)phenyl
138. 2-pyrimidyl 2-((cyclobutyl)$NHCH_2$)phenyl
139. 2-pyrimidyl 2-((cyclobutyl)$_2NCH_2$)phenyl
140. 2-pyrimidyl 2-((cyclopentyl)$NHCH_2$)phenyl
141. 2-pyrimidyl 2-((cyclopentyl)$_2NCH_2$)phenyl
142. 2-pyrimidyl 2-((cyclohexyl)$NHCH_2$)phenyl
143. 2-pyrimidyl 2-((cyclohexyl)$_2NCH_2$)phenyl
144. 2-pyrimidyl 1-$CH_{3-2}$-imidazolyl
145. 2-pyrimidyl 2-$CH_{3-1}$-imidazolyl
146. 2-pyrimidyl 2-(($CH_3)_2NCH_2$)-1-imidazolyl
147. 2-pyrimidyl 2-(($CH_3)NHCH_2$)-1-imidazolyl
148. 2-pyrimidyl 2-(($CH_3CH_2)NHCH_2$)-1-imidazolyl
149. 2-pyrimidyl 2-(($CH_3CH_2)_2NCH_2$)-1-imidazolyl
150. 2-pyrimidyl 2-(($CH_3CH_2)N(CH_3)CH_2$)-1-imidazolyl
151. 2-pyrimidyl 2-((($CH_3)_2CH)NHCH_2$)-1-imidazolyl
152. 2-pyrimidyl 2-((($CH_3)_2CH)_2NCH_2$)-1-imidazolyl
153. 2-pyrimidyl 2-((cyclopropyl)$NHCH_2$)-1-imidazolyl
154. 2-pyrimidyl 2-((cyclopropyl)$_2NCH_2$)-1-imidazolyl
155. 2-pyrimidyl 2-((cyclobutyl)$NHCH_2$)-1-imidazolyl
156. 2-pyrimidyl 2-((cyclobutyl)$_2NCH_2$)-1-imidazolyl
157. 2-pyrimidyl 2-((cyclopentyl)$NHCH_2$)-1-imidazolyl
158. 2-pyrimidyl 2-((cyclopentyl)$_2NCH_2$)-1-imidazolyl
159. 2-pyrimidyl 2-((cyclohexyl)$NHCH_2$)-1-imidazolyl
160. 2-pyrimidyl 2-((cyclohexyl)$_2NCH_2$)-1-imidazolyl
161. 5-pyrimidyl 2-($NH_2SO_2$)phenyl
162. 5-pyrimidyl 2-($CH_3SO_2$)phenyl
163. 5-pyrimidyl 3-$NH_2SO_{2-4}$-pyridyl
164. 5-pyrimidyl 3-$CH_3SO_{2-4}$-pyridyl
165. 5-pyrimidyl 2-($CH_3NH$)phenyl
166. 5-pyrimidyl 3-(($CH_3)_2NCH_2$)-4-pyridyl
167. 5-pyrimidyl 2-(N-(3-R—HO-pyrrolidinyl)$CH_2$)phenyl
168. 5-pyrimidyl 2-(N-(4-HO-piperidinyl)$CH_2$)phenyl
169. 5-pyrimidyl 2-(($CH_3)_2NCH_2$)phenyl
170. 5-pyrimidyl 2-(($CH_3)NHCH_2$)phenyl
171. 5-pyrimidyl 2-(($CH_3CH_2)NHCH_2$)phenyl
172. 5-pyrimidyl 2-(($CH_3CH_2)_2NCH_2$)phenyl
173. 5-pyrimidyl 2-(($CH_3CH_2)N(CH_3)CH_2$)phenyl
174. 5-pyrimidyl 2-((($CH_3)_2CH)NHCH_2$)phenyl
175. 5-pyrimidyl 2-((($CH_3)_2CH)_2NCH_2$)phenyl
176. 5-pyrimidyl 2-((cyclopropyl)$NHCH_2$)phenyl
177. 5-pyrimidyl 2-((cyclopropyl)$_2NCH_2$)phenyl
178. 5-pyrimidyl 2-((cyclobutyl)$NHCH_2$)phenyl
179. 5-pyrimidyl 2-((cyclobutyl)$_2NCH_2$)phenyl
180. 5-pyrimidyl 2-((cyclopentyl)$NHCH_2$)phenyl
181. 5-pyrimidyl 2-((cyclopentyl)$_2NCH_2$)phenyl
182. 5-pyrimidyl 2-((cyclohexyl)$NHCH_2$)phenyl
183. 5-pyrimidyl 2-((cyclohexyl)$_2NCH_2$)phenyl
184. 5-pyrimidyl 1-$CH_{3-2}$-imidazolyl
185. 5-pyrimidyl 2-$CH_{3-1}$-imidazolyl
186. 5-pyrimidyl 2-(($CH_3)_2NCH_2$)-1-imidazolyl
187. 5-pyrimidyl 2-(($CH_3)NHCH_2$)-1-imidazolyl
188. 5-pyrimidyl 2-(($CH_3CH_2)NHCH_2$)-1-imidazolyl
189. 5-pyrimidyl 2-(($CH_3CH_2)_2NCH_2$)-1-imidazolyl
190. 5-pyrimidyl 2-(($CH_3CH_2)N(CH_3)CH_2$)-1-imidazolyl
191. 5-pyrimidyl 2-((($CH_3)_2CH)NHCH_2$)-1-imidazolyl
192. 5-pyrimidyl 2-((($CH_3)_2CH)_2NCH_2$)-1-imidazolyl
193. 5-pyrimidyl 2-((cyclopropyl)$NHCH_2$)-1-imidazolyl
194. 5-pyrimidyl 2-((cyclopropyl)$_2NCH_2$)-1-imidazolyl
195. 5-pyrimidyl 2-((cyclobutyl)$NHCH_2$)-1-imidazolyl
196. 5-pyrimidyl 2-((cyclobutyl)$_2NCH_2$)-1-imidazolyl
197. 5-pyrimidyl 2-((cyclopentyl)$NHCH_2$)-1-imidazolyl
198. 5-pyrimidyl 2-((cyclopentyl)$_2NCH_2$)-1-imidazolyl
199. 5-pyrimidyl 2-((cyclohexyl)$NHCH_2$)-1-imidazolyl
200. 5-pyrimidyl 2-((cyclohexyl)$_2NCH_2$)-1-imidazolyl
201. 2-Cl-phenyl 2-($NH_2SO_2$)phenyl
202. 2-Cl-phenyl 2-($CH_3SO_2$)phenyl
203. 2-Cl-phenyl 3-$NH_2SO_{2-4}$-pyridyl
204. 2-Cl-phenyl 3-$CH_3SO_{2-4}$-pyridyl
205. 2-Cl-phenyl 2-($CH_3NH$)phenyl
206. 2-Cl-phenyl 3-(($CH_3)_2NCH_2$)-4-pyridyl
207. 2-Cl-phenyl 2-(N-(3-R—HO-pyrrolidinyl)$CH_2$)phenyl
208. 2-Cl-phenyl 2-(N-(4-HO-piperidinyl)$CH_2$)phenyl
209. 2-Cl-phenyl 2-(($CH_3)_2NCH_2$)phenyl
210. 2-Cl-phenyl 2-(($CH_3)NHCH_2$)phenyl
211. 2-Cl-phenyl 2-($CH_3CH_2)NHCH_2$)phenyl
212. 2-Cl-phenyl 2-(($CH_3CH_2)_2NCH_2$)phenyl
213. 2-Cl-phenyl 2-(($CH_3CH_2)N(CH_3)CH_2$)phenyl
214. 2-Cl-phenyl 2-((($CH_3)_2CH)NHCH_2$)phenyl
215. 2-Cl-phenyl 2-((($CH_3)_2CH)_2NCH_2$)phenyl
216. 2-Cl-phenyl 2-((cyclopropyl)$NHCH_2$)phenyl
217. 2-Cl-phenyl 2-((cyclopropyl)$_2NCH_2$)phenyl
218. 2-Cl-phenyl 2-((cyclobutyl)$NHCH_2$)phenyl
219. 2-Cl-phenyl 2-((cyclobutyl)$_2NCH_2$)phenyl
220. 2-Cl-phenyl 2-((cyclopentyl)$NHCH_2$)phenyl
221. 2-Cl-phenyl 2-((cyclopentyl)$_2NCH_2$)phenyl
222. 2-Cl-phenyl 2-((cyclohexyl)$NHCH_2$)phenyl
223. 2-Cl-phenyl 2-((cyclohexyl)$_2NCH_2$)phenyl
224. 2-Cl-phenyl 1-$CH_{3-2}$-imidazolyl
225. 2-Cl-phenyl 2-$CH_{3-1}$-imidazolyl
226. 2-Cl-phenyl 2-(($CH_3)_2NCH_2$)-1-imidazolyl
227. 2-Cl-phenyl 2-(($CH_3)NHCH_2$)-1-imidazolyl
228. 2-Cl-phenyl 2-(($CH_3CH_2)NHCH_2$)-1-imidazolyl
229. 2-Cl-phenyl 2-(($CH_3CH_2)_2NCH_2$)-1-imidazolyl
230. 2-Cl-phenyl 2-(($CH_3CH_2)N(CH_3)CH_2$)-1-imidazolyl
231. 2-Cl-phenyl 2-((($CH_3)_2CH)NHCH_2$)-1-imidazolyl
232. 2-Cl-phenyl 2-((($CH_3)_2CH)_2NCH_2$)-1-imidazolyl
233. 2-Cl-phenyl 2-((cyclopropyl)$NHCH_2$)-1-imidazolyl
234. 2-Cl-phenyl 2-((cyclopropyl)$_2NCH_2$)-1-imidazolyl
235. 2-Cl-phenyl 2-((cyclobutyl)$NHCH_2$)-1-imidazolyl
236. 2-Cl-phenyl 2-((cyclobutyl)$_2NCH_2$)-1-imidazolyl
237. 2-Cl-phenyl 2-((cyclopentyl)$NHCH_2$)-1-imidazolyl 238. 2-Cl-phenyl 2-((cyclopentyl)$_2$NCH$_2$)-1-imidazolyl
239. 2-Cl-phenyl 2-((cyclohexyl)NHCH$_2$)-1-imidazolyl
240. 2-Cl-phenyl 2-((cyclohexyl)$_2$NCH$_2$)-1-imidazolyl
241. 2-F-phenyl 2-(NH$_2$SO$_2$)phenyl
242. 2-F-phenyl 2-(CH$_3$SO$_2$)phenyl
243. 2-F-phenyl 3-NH$_2$SO$_{2-4}$-pyridyl
244. 2-F-phenyl 3-CH$_3$SO$_{2-4}$-pyridyl
245. 2-F-phenyl 2-(CH$_3$NH)phenyl
246. 2-F-phenyl 3-((CH$_3$)$_2$NCH$_2$)-4-pyridyl
247. 2-F-phenyl 2-(N-(3-R—HO-pyrrolidinyl)CH$_2$)phenyl
248. 2-F-phenyl 2-(N-(4-HO-piperidinyl)CH$_2$)phenyl
249. 2-F-phenyl 2-((CH$_3$)$_2$NCH$_2$)phenyl
250. 2-F-phenyl 2-((CH$_3$)NHCH$_2$)phenyl
251. 2-F-phenyl 2-((CH$_3$CH$_2$)NHCH$_2$)phenyl
252. 2-F-phenyl 2-((CH$_3$CH$_2$)$_2$NCH$_2$)phenyl
253. 2-F-phenyl 2-((CH$_3$CH$_2$)N(CH$_3$)CH$_2$)phenyl
254. 2-F-phenyl 2-(((CH$_3$)$_2$CH)NHCH$_2$)phenyl
255. 2-F-phenyl 2-(((CH$_3$)$_2$CH)$_2$NCH$_2$)phenyl
256. 2-F-phenyl 2-((cyclopropyl)NHCH$_2$)phenyl
257. 2-F-phenyl 2-((cyclopropyl)$_2$NCH$_2$)phenyl
258. 2-F-phenyl 2-((cyclobutyl)NHCH$_2$)phenyl
259. 2-F-phenyl 2-((cyclobutyl)$_2$NCH$_2$)phenyl
260. 2-F-phenyl 2-((cyclopentyl)NHCH$_2$)phenyl
261. 2-F-phenyl 2-((cyclopentyl)$_2$NCH$_2$)phenyl
262. 2-F-phenyl 2-((cyclohexyl)NHCH$_2$)phenyl
263. 2-F-phenyl 2-((cyclohexyl)$_2$NCH$_2$)phenyl
264. 2-F-phenyl 1-CH$_{3-2}$-imidazolyl
265. 2-F-phenyl 2-CH$_{3-1}$-imidazolyl
266. 2-F-phenyl 2-((CH$_3$)$_2$NCH$_2$)-1-imidazolyl
267. 2-F-phenyl 2-((CH$_3$)NHCH$_2$)-1-imidazolyl
268. 2-F-phenyl 2-((CH$_3$CH$_2$)NHCH$_2$)-1-imidazolyl
269. 2-F-phenyl 2-((CH$_3$CH$_2$)$_2$NCH$_2$)-1-imidazolyl
270. 2-F-phenyl 2-((CH$_3$CH$_2$)N(CH$_3$)CH$_2$)-1-imidazolyl
271. 2-F-phenyl 2-(((CH$_3$)$_2$CH)NHCH$_2$)-1-imidazolyl
272. 2-F-phenyl 2-(((CH$_3$)$_2$CH)$_2$NCH$_2$)-1-imidazolyl
273. 2-F-phenyl 2-((cyclopropyl)NHCH$_2$)-1-imidazolyl
274. 2-F-phenyl 2-((cyclopropyl)$_2$NCH$_2$)-1-imidazolyl
275. 2-F-phenyl 2-((cyclobutyl)NHCH$_2$)-1-imidazolyl
276. 2-F-phenyl 2-((cyclobutyl)$_2$NCH$_2$)-1-imidazolyl
277. 2-F-phenyl 2-((cyclopentyl)NHCH$_2$)-1-imidazolyl
278. 2-F-phenyl 2-((cyclopentyl)$_2$NCH$_2$)-1-imidazolyl
279. 2-F-phenyl 2-((cyclohexyl)NHCH$_2$)-1-imidazolyl
280. 2-F-phenyl 2-((cyclohexyl)$_2$NCH$_2$)-1-imidazolyl
281. 2,6-diF-phenyl 2-(NH$_2$SO$_2$)phenyl
282. 2,6-diF-phenyl 2-(CH$_3$SO$_2$)phenyl
283. 2,6-diF-phenyl 3-NH$_2$SO$_{2-4}$-pyridyl
284. 2,6-diF-phenyl 3-CH$_3$SO$_{2-4}$-pyridyl
285. 2,6-diF-phenyl 2-(CH$_3$NH)phenyl
286. 2,6-diF-phenyl 3-((CH$_3$)$_2$NCH$_2$)-4-pyridyl
287. 2,6-diF-phenyl 2-(N-(3-R—HO-pyrrolidinyl)CH$_2$)phenyl
288. 2,6-diF-phenyl 2-(N-(4-HO-piperidinyl)CH$_2$)phenyl
289. 2,6-diF-phenyl 2-((CH$_3$)$_2$NCH$_2$)phenyl
290. 2,6-diF-phenyl 2-((CH$_3$)NHCH$_2$)phenyl
291. 2,6-diF-phenyl 2-((CH$_3$CH$_2$)NHCH$_2$)phenyl
292. 2,6-diF-phenyl 2-((CH$_3$CH$_2$)$_2$NCH$_2$)phenyl
293. 2,6-diF-phenyl 2-((CH$_3$CH$_2$)N(CH$_3$)CH$_2$)phenyl
294. 2,6-diF-phenyl 2-(((CH$_3$)$_2$CH)NHCH$_2$)phenyl
295. 2,6-diF-phenyl 2-(((CH$_3$)$_2$CH)$_2$NCH$_2$)phenyl
296. 2,6-diF-phenyl 2-((cyclopropyl)NHCH$_2$)phenyl
297. 2,6-diF-phenyl 2-((cyclopropyl)$_2$NCH$_2$)phenyl
298. 2,6-diF-phenyl 2-((cyclobutyl)NHCH$_2$)phenyl
299. 2,6-diF-phenyl 2-((cyclobutyl)$_2$NCH$_2$)phenyl
300. 2,6-diF-phenyl 2-((cyclopentyl)NHCH$_2$)phenyl
301. 2,6-diF-phenyl 2-((cyclopentyl)$_2$NCH$_2$)phenyl
302. 2,6-diF-phenyl 2-((cyclohexyl)NHCH$_2$)phenyl
303. 2,6-diF-phenyl 2-((cyclohexyl)$_2$NCH$_2$)phenyl
304. 2,6-diF-phenyl 1-CH$_{3-2}$-imidazolyl
305. 2,6-diF-phenyl 2-CH$_{3-1}$-imidazolyl
306. 2,6-diF-phenyl 2-((CH$_3$)$_2$NCH$_2$)-1-imidazolyl
307. 2,6-diF-phenyl 2-((CH$_3$)NHCH$_2$)-1-imidazolyl
308. 2,6-diF-phenyl 2-((CH$_3$CH$_2$)NHCH$_2$)-1-imidazolyl
309. 2,6-diF-phenyl 2-((CH$_3$CH$_2$)$_2$NCH$_2$)-1-imidazolyl
310. 2,6-diF-phenyl 2-((CH$_3$CH$_2$)N(CH$_3$)CH$_2$)-1-imidazolyl
311. 2,6-diF-phenyl 2-(((CH$_3$)$_2$CH)NHCH$_2$)-1-imidazolyl
312. 2,6-diF-phenyl 2-(((CH$_3$)$_2$CH)$_2$NCH$_2$)-1-imidazolyl
313. 2,6-diF-phenyl 2-((cyclopropyl)NHCH$_2$)-1-imidazolyl
314. 2,6-diF-phenyl 2-((cyclopropyl)$_2$NCH$_2$)-1-imidazolyl
315. 2,6-diF-phenyl 2-((cyclobutyl)NHCH$_2$)-1-imidazolyl
316. 2,6-diF-phenyl 2-((cyclobutyl)$_2$NCH$_2$)-1-imidazolyl
317. 2,6-diF-phenyl 2-((cyclopentyl)NHCH$_2$)-1-imidazolyl
318. 2,6-diF-phenyl 2-((cyclopentyl)$_2$NCH$_2$)-1-imidazolyl
319. 2,6-diF-phenyl 2-((cyclohexyl)NHCH$_2$)-1-imidazolyl
320. 2,6-diF-phenyl 2-((cyclohexyl)$_2$NCH$_2$)-1-imidazolyl
321. piperidinyl 2-(NH$_2$SO$_2$)phenyl
322. piperidinyl 2-(CH$_3$SO$_2$)phenyl
323. piperidinyl 3-NH$_2$SO$_{2-4}$-pyridyl
324. piperidinyl 3-CH$_3$SO$_{2-4}$-pyridyl
325. piperidinyl 2-(CH$_3$NH)phenyl
326. piperidinyl 3-((CH$_3$)$_2$NCH$_2$)-4-pyridyl
327. piperidinyl 2-(N-(3-R—HO-pyrrolidinyl)CH$_2$)phenyl
328. piperidinyl 2-(N-(4-HO-piperidinyl)CH$_2$)phenyl
329. piperidinyl 2-((CH$_3$)$_2$NCH$_2$)phenyl
330. piperidinyl 2-((CH$_3$)NHCH$_2$)phenyl
331. piperidinyl 2-((CH$_3$CH$_2$)NHCH$_2$)phenyl
332. piperidinyl 2-((CH$_3$CH$_2$)$_2$NCH$_2$)phenyl
333. piperidinyl 2-((CH$_3$CH$_2$)N(CH$_3$)CH$_2$)phenyl
334. piperidinyl 2-(((CH$_3$)$_2$CH)NHCH$_2$)phenyl
335. piperidinyl 2-(((CH$_3$)$_2$CH)$_2$NCH$_2$)phenyl
336. piperidinyl 2-((cyclopropyl)NHCH$_2$)phenyl
337. piperidinyl 2-((cyclopropyl)$_2$NCH$_2$)phenyl
338. piperidinyl 2-((cyclobutyl)NHCH$_2$)phenyl
339. piperidinyl 2-((cyclobutyl)$_2$NCH$_2$)phenyl
340. piperidinyl 2-((cyclopentyl)NHCH$_2$)phenyl
341. piperidinyl 2-((cyclopentyl)$_2$NCH$_2$)phenyl
342. piperidinyl 2-((cyclohexyl)NHCH$_2$)phenyl
343. piperidinyl 2-((cyclohexyl)$_2$NCH$_2$)phenyl
344. piperidinyl 1-CH$_{3-2}$-imidazolyl
345. piperidinyl 2-CH$_{3-1}$-imidazolyl
346. piperidinyl 2-((CH$_3$)$_2$NCH$_2$)-1-imidazolyl
347. piperidinyl 2-((CH$_3$)NHCH$_2$)-1-imidazolyl
348. piperidinyl 2-((CH$_3$CH$_2$)NHCH$_2$)-1-imidazolyl
349. piperidinyl 2-((CH$_3$CH$_2$)$_2$NCH$_2$)-1-imidazolyl
350. piperidinyl 2-((CH$_3$CH$_2$)N(CH$_3$)CH$_2$)-1-imidazolyl
351. piperidinyl 2-(((CH$_3$)$_2$CH)NHCH$_2$)-1-imidazolyl
352. piperidinyl 2-(((CH$_3$)$_2$CH)$_2$NCH$_2$)-1-imidazolyl
353. piperidinyl 2-((cyclopropyl)NHCH$_2$)-1-imidazolyl
354. piperidinyl 2-((cyclopropyl)$_2$NCH$_2$)-1-imidazolyl
355. piperidinyl 2-((cyclobutyl)NHCH$_2$)-1-imidazolyl
356. piperidinyl 2-((cyclobutyl)$_2$NCH$_2$)-1-imidazolyl
357. piperidinyl 2-((cyclopentyl)NHCH$_2$)-1-imidazolyl
358. piperidinyl 2-((cyclopentyl)$_2$NCH$_2$)-1-imidazolyl
359. piperidinyl 2-((cyclohexyl)NHCH$_2$)-1-imidazolyl
360. piperidinyl 2-((cyclohexyl)$_2$NCH$_2$)-1-imidazolyl
361. piperidinyl isopropyl Examples 362–6498 use the corresponding A and B groups from Examples 1–361 and the recited G group.
Examples 362–722, G is 3-aminoindazol-6-yl;
Examples 723–1083, G is 3-amidophenyl;
Examples 1084–1444, G is 2-(aminomethyl)phenyl;
Examples 1445–1805, G is 3-(aminomethyl)phenyl;
Examples 1806–2166, G is 2-(aminomethyl)-3-fluorophenyl;

Examples 2167–2527, G is 2-(aminomethyl)-4-fluorophenyl;
Examples 2528–2888, G is 4-Cl-2-pyridyl;
Examples 2889–3249, G is 4-chlorophenyl;
Examples 3250–3610, G is 3-amino-4-chloro-phenyl;
Examples 3611–3971, G is 3-amidino-phenyl;
Examples 3972–4332, G is 1-aminoisoquinolin-6-yl;
Examples 4333–4693, G is 1-aminoisoquinolin-7-yl;
Examples 4694–5054, G is 4-aminoquinazol-6-yl;
Examples 5055–5415, G is 4-aminoquinazol-7-yl;
Examples 5416–5776, G is 3-aminobenzisoxazol-5-yl;
Examples 5777–6137, G is 3-aminobenzisoxazol-6-yl; and,
Examples 6138–6498, G is 3-aminoindazol-5-yl.

Table 2

Examples 1–6498 of Table 1, wherein $G_1$ is $NH_2C(O)$.

Table 3

Examples 1–6498 of Table 1, wherein $G_1$ is $C(O)NH_2$.

TABLE 4

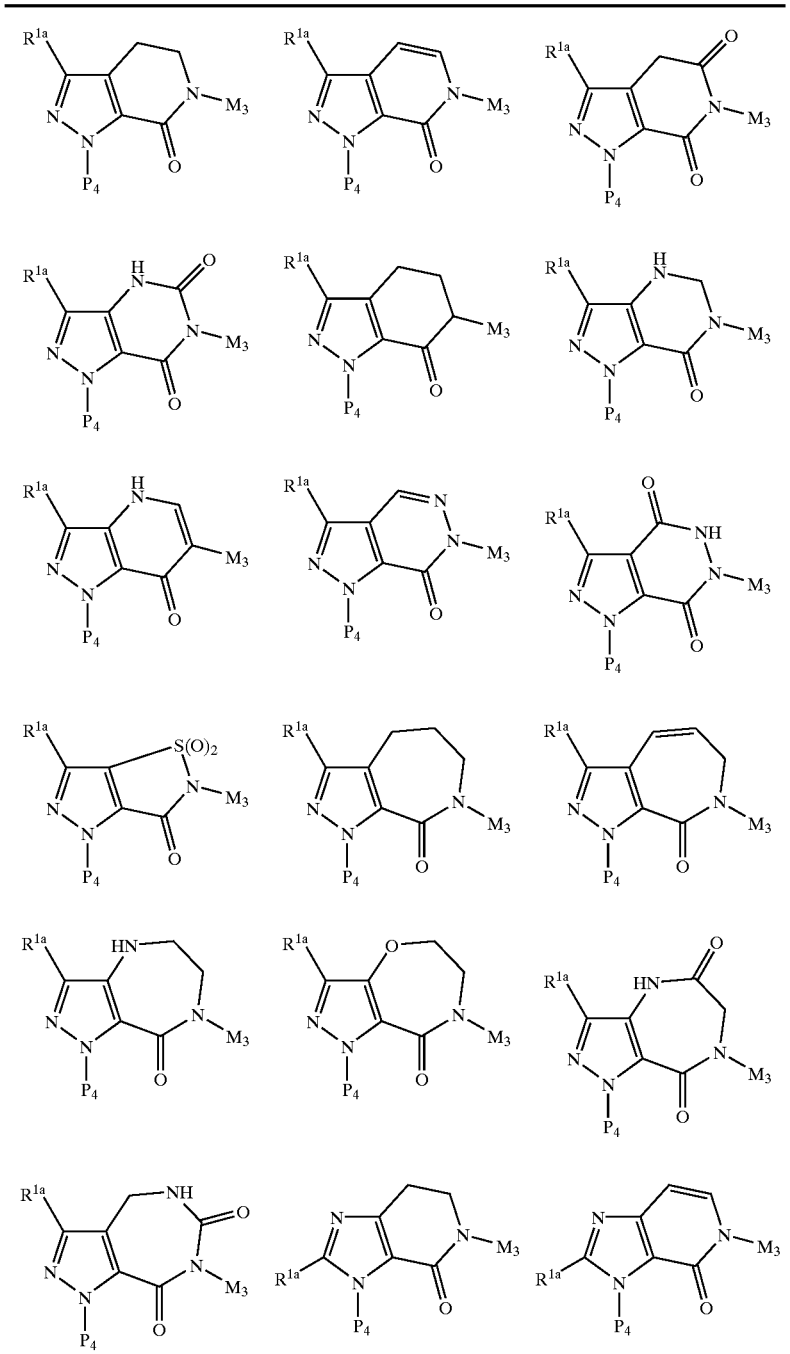

TABLE 4-continued
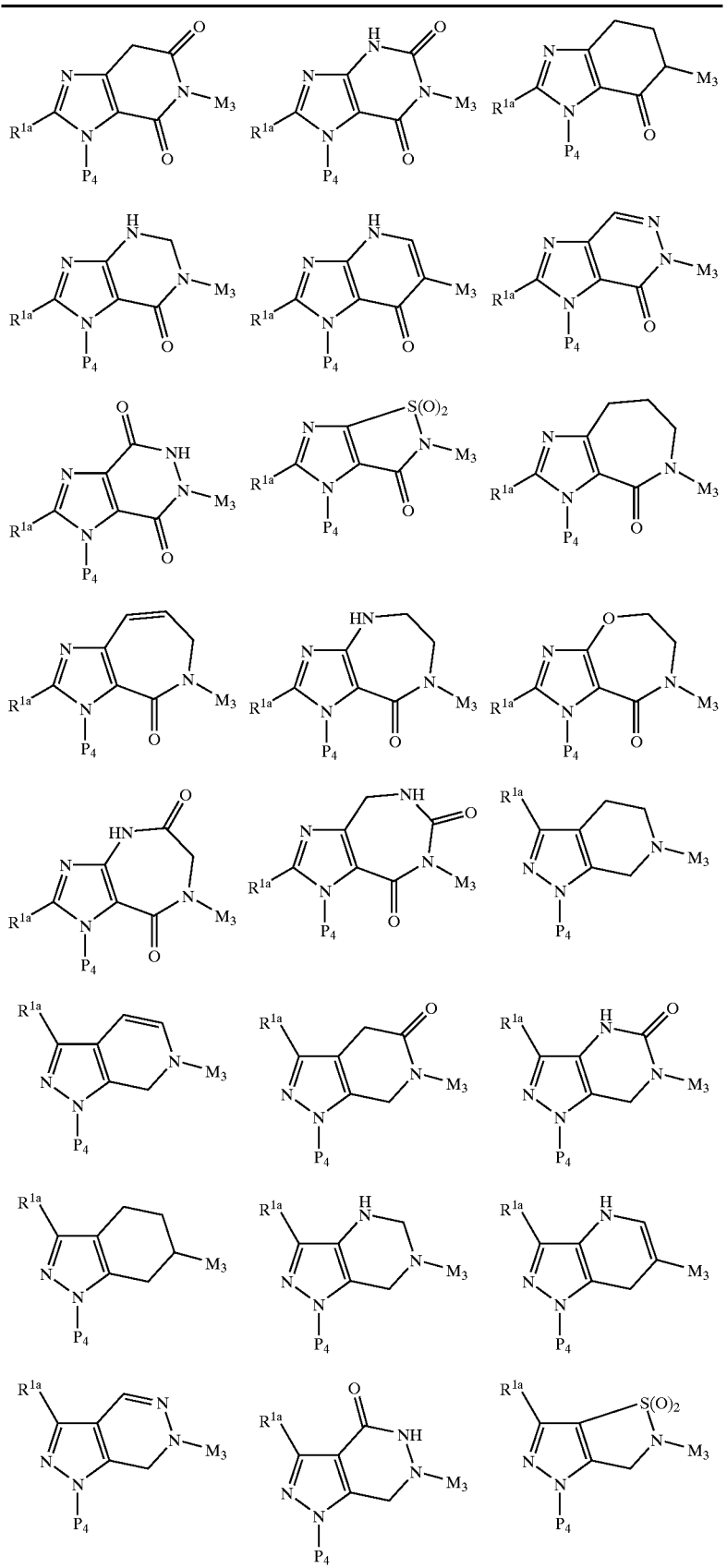

TABLE 4-continued
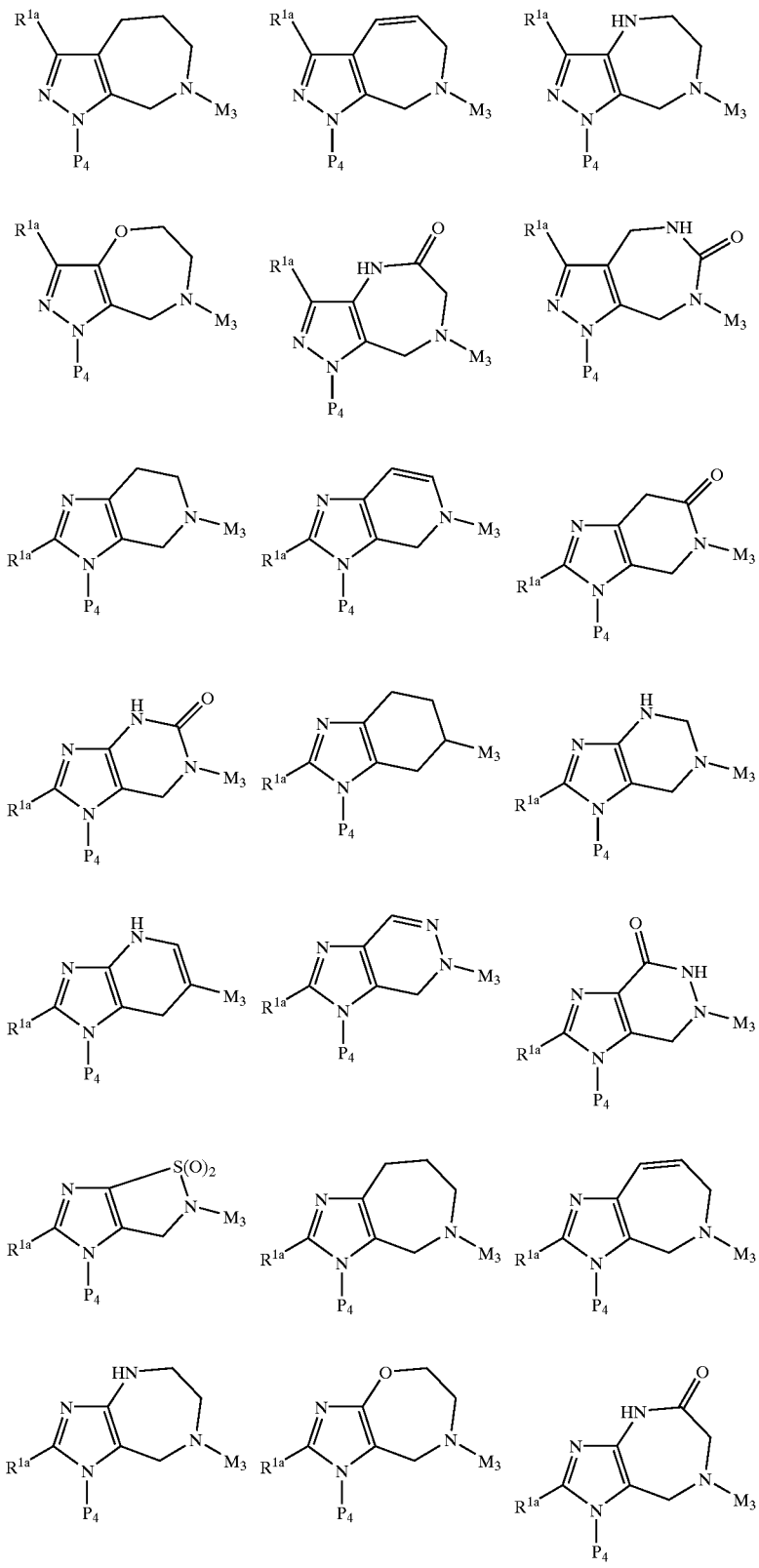

TABLE 4-continued

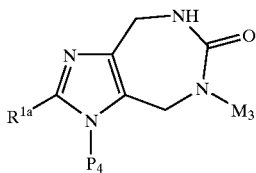

P$_4$ is Z-A-B, wherein Z is a bond;
M$_3$ is -G$_1$-G, wherein G$_1$ is a bond, NH$_2$C(O), or C(O)NH$_2$;
R$^{1a}$ is CH$_3$;
G is 4-(methoxy)phenyl;

Ex# A B 362. phenyl 2-(NH$_2$SO$_2$)phenyl
363. phenyl 2-(CH$_3$SO$_2$)phenyl
364. phenyl 3-NH$_2$SO$_{2-4}$-pyridyl
365. phenyl 3-CH$_3$SO$_{2-4}$-pyridyl
366. phenyl 2-(CH$_3$NH)phenyl
367. phenyl 3-((CH$_3$)$_2$NCH$_2$)-4-pyridyl
368. phenyl 2-(N-(3-R—HO-pyrrolidinyl)CH$_2$)phenyl
369. phenyl 2-(N-(4-HO-piperidinyl)CH$_2$)phenyl
370. phenyl 2-((CH$_3$)$_2$NCH$_2$)phenyl
371. phenyl 2-((CH$_3$)NHCH$_2$)phenyl
372. phenyl 2-((CH$_3$CH$_2$)NHCH$_2$)phenyl
373. phenyl 2-((CH$_3$CH$_2$)$_2$NCH$_2$)phenyl
374. phenyl 2-((CH$_3$CH$_2$)N(CH$_3$)CH$_2$)phenyl
375. phenyl 2-(((CH$_3$)$_2$CH)NHCH$_2$)phenyl
376. phenyl 2-(((CH$_3$)$_2$CH)$_2$NCH$_2$)phenyl
377. phenyl 2-((cyclopropyl)NHCH$_2$)phenyl
378. phenyl 2-((cyclopropyl)$_2$NCH$_2$)phenyl
379. phenyl 2-((cyclobutyl)NHCH$_2$)phenyl
380. phenyl 2-((cyclobutyl)$_2$NCH$_2$)phenyl
381. phenyl 2-((cyclopentyl)NHCH$_2$)phenyl
382. phenyl 2-((cyclopentyl)$_2$NCH$_2$)phenyl
383. phenyl 2-((cyclohexyl)NHCH$_2$)phenyl
384. phenyl 2-((cyclohexyl)$_2$NCH$_2$)phenyl
385. phenyl 1-CH$_{3-2}$-imidazolyl
386. phenyl 2-CH$_{3-1}$-imidazolyl
387. phenyl 2-((CH$_3$)$_2$NCH$_2$)-1-imidazolyl
388. phenyl 2-((CH$_3$)NHCH$_2$)-1-imidazolyl
389. phenyl 2-((CH$_3$CH$_2$)NHCH$_2$)-1-imidazolyl
390. phenyl 2-((CH$_3$CH$_2$)$_2$NCH$_2$)-1-imidazolyl
391. phenyl 2-((CH$_3$CH$_2$)N(CH$_3$)CH$_2$)-1-imidazolyl
392. phenyl 2-(((CH$_3$)$_2$CH)NHCH$_2$)-1-imidazolyl
393. phenyl 2-(((CH$_3$)$_2$CH)$_2$NCH$_2$)-1-imidazolyl
394. phenyl 2-((cyclopropyl)NHCH$_2$)-1-imidazolyl
395. phenyl 2-((cyclopropyl)$_2$NCH$_2$)-1-imidazolyl
396. phenyl 2-((cyclobutyl)NHCH$_2$)-1-imidazolyl
397. phenyl 2-((cyclobutyl)$_2$NCH$_2$)-1-imidazolyl
398. phenyl 2-((cyclopentyl)NHCH$_2$)-1-imidazolyl
399. phenyl 2-((cyclopentyl)$_2$NCH$_2$)-1-imidazolyl
400. phenyl 2-((cyclohexyl)NHCH$_2$)-1-imidazolyl
401. phenyl 2-((cyclohexyl)$_2$NCH$_2$)-1-imidazolyl
402. 2-pyridyl 2-(NH$_2$SO$_2$)phenyl
403. 2-pyridyl 2-(CH$_3$SO$_2$)phenyl
404. 2-pyridyl 3-NH$_2$SO$_{2-4}$-pyridyl
405. 2-pyridyl 3-CH$_3$SO$_{2-4}$-pyridyl
406. 2-pyridyl 2-(CH$_3$NH)phenyl
407. 2-pyridyl 3-((CH$_3$)$_2$NCH$_2$)-4-pyridyl
408. 2-pyridyl 2-(N-(3-R—HO-pyrrolidinyl)CH$_2$)phenyl
409. 2-pyridyl 2-(N-(4-HO-piperidinyl)CH$_2$)phenyl
410. 2-pyridyl 2-((CH$_3$)$_2$NCH$_2$)phenyl
411. 2-pyridyl 2-((CH$_3$)NHCH$_2$)phenyl
412. 2-pyridyl 2-((CH$_3$CH$_2$)NHCH$_2$)phenyl
413. 2-pyridyl 2-((CH$_3$CH$_2$)$_2$NCH$_2$)phenyl
414. 2-pyridyl 2-((CH$_3$CH$_2$)N(CH$_3$)CH$_2$)phenyl
415. 2-pyridyl 2-(((CH$_3$)$_2$CH)NHCH$_2$)phenyl
416. 2-pyridyl 2-(((CH$_3$)$_2$CH)$_2$NCH$_2$)phenyl
417. 2-pyridyl 2-((cyclopropyl)NHCH$_2$)phenyl
418. 2-pyridyl 2-((cyclopropyl)$_2$NCH$_2$)phenyl
419. 2-pyridyl 2-((cyclobutyl)NHCH$_2$)phenyl
420. 2-pyridyl 2-((cyclobutyl)$_2$NCH$_2$)phenyl
421. 2-pyridyl 2-((cyclopentyl)NHCH$_2$)phenyl
422. 2-pyridyl 2-((cyclopentyl)$_2$NCH$_2$)phenyl
423. 2-pyridyl 2-((cyclohexyl)NHCH$_2$)phenyl
424. 2-pyridyl 2-((cyclohexyl)$_2$NCH$_2$)phenyl
425. 2-pyridyl 1-CH$_{3-2}$-imidazolyl
426. 2-pyridyl 2-CH$_{3-1}$-imidazolyl
427. 2-pyridyl 2-((CH$_3$)$_2$NCH$_2$)-1-imidazolyl
428. 2-pyridyl 2-((CH$_3$)NHCH$_2$)-1-imidazolyl
429. 2-pyridyl 2-((CH$_3$CH$_2$)NHCH$_2$)-1-imidazolyl
430. 2-pyridyl 2-((CH$_3$CH$_2$)$_2$NCH$_2$)-1-imidazolyl
431. 2-pyridyl 2-((CH$_3$CH$_2$)N(CH$_3$)CH$_2$)-1-imidazolyl
432. 2-pyridyl 2-(((CH$_3$)$_2$CH)NHCH$_2$)-1-imidazolyl
433. 2-pyridyl 2-(((CH$_3$)$_2$CH)$_2$NCH$_2$)-1-imidazolyl
434. 2-pyridyl 2-((cyclopropyl)NHCH$_2$)-1-imidazolyl
435. 2-pyridyl 2-((cyclopropyl)$_2$NCH$_2$)-1-imidazolyl
436. 2-pyridyl 2-((cyclobutyl)NHCH$_2$)-1-imidazolyl
437. 2-pyridyl 2-((cyclobutyl)$_2$NCH$_2$)-1-imidazolyl
438. 2-pyridyl 2-((cyclopentyl)NHCH$_2$)-1-imidazolyl
439. 2-pyridyl 2-((cyclopentyl)$_2$NCH$_2$)-1-imidazolyl
440. 2-pyridyl 2-((cyclohexyl)NHCH$_2$)-1-imidazolyl
441. 2-pyridyl 2-((cyclohexyl)$_2$NCH$_2$)-1-imidazolyl
442. 3-pyridyl 2-(NH$_2$SO$_2$)phenyl
443. 3-pyridyl 2-(CH$_3$SO$_2$)phenyl
444. 3-pyridyl 3-NH$_2$SO$_{2-4}$-pyridyl
445. 3-pyridyl 3-CH$_3$SO$_{2-4}$-pyridyl
446. 3-pyridyl 2-(CH$_3$NH)phenyl
447. 3-pyridyl 3-((CH$_3$)$_2$NCH$_2$)-4-pyridyl
448. 3-pyridyl 2-(N-(3-R—HO-pyrrolidinyl)CH$_2$)phenyl
449. 3-pyridyl 2-(N-(4-HO-piperidinyl)CH$_2$)phenyl
450. 3-pyridyl 2-((CH$_3$)$_2$NCH$_2$)phenyl
451. 3-pyridyl 2-((CH$_3$)NHCH$_2$)phenyl
452. 3-pyridyl 2-((CH$_3$CH$_2$)NHCH$_2$)phenyl
453. 3-pyridyl 2-((CH$_3$CH$_2$)$_2$NCH$_2$)phenyl
454. 3-pyridyl 2-((CH$_3$CH$_2$)N(CH$_3$)CH$_2$)phenyl
455. 3-pyridyl 2-(((CH$_3$)$_2$CH)NHCH$_2$)phenyl
456. 3-pyridyl 2-(((CH$_3$)$_2$CH)$_2$NCH$_2$)phenyl
457. 3-pyridyl 2-((cyclopropyl)NHCH$_2$)phenyl
458. 3-pyridyl 2-((cyclopropyl)$_2$NCH$_2$)phenyl
459. 3-pyridyl 2-((cyclobutyl)NHCH$_2$)phenyl
460. 3-pyridyl 2-((cyclobutyl)$_2$NCH$_2$)phenyl
461. 3-pyridyl 2-((cyclopentyl)NHCH$_2$)phenyl
462. 3-pyridyl 2-((cyclopentyl)$_2$NCH$_2$)phenyl
463. 3-pyridyl 2-((cyclohexyl)NHCH$_2$)phenyl
464. 3-pyridyl 2-((cyclohexyl)$_2$NCH$_2$)phenyl
465. 3-pyridyl 1-CH$_{3-2}$-imidazolyl
466. 3-pyridyl 2-CH$_{3-1}$-imidazolyl 467. 3-pyridyl 2-((CH$_3$)$_2$NCH$_2$)-1-imidazolyl
468. 3-pyridyl 2-((CH$_3$)NHCH$_2$)-1-imidazolyl
469. 3-pyridyl 2-((CH$_3$CH$_2$)NHCH$_2$)-1-imidazolyl
470. 3-pyridyl 2-((CH$_3$CH$_2$)$_2$NCH$_2$)-1-imidazolyl
471. 3-pyridyl 2-((CH$_3$CH$_2$) N(H$_3$)CH$_2$)-1-imidazolyl
472. 3-pyridyl 2-(((CH$_3$)$_2$CH)NHCH$_2$)-1-imidazolyl
473. 3-pyridyl 2-(((CH$_3$)$_2$CH)$_2$NCH$_2$)-1-imidazolyl
474. 3-pyridyl 2-((cyclopropyl)NHCH$_2$)-1-imidazolyl
475. 3-pyridyl 2-((cyclopropyl)$_2$NCH$_2$)-1-imidazolyl
476. 3-pyridyl 2-((cyclobutyl)NHCH$_2$)-1-imidazolyl
477. 3-pyridyl 2-((cyclobutyl)$_2$NCH$_2$)-1-imidazolyl
478. 3-pyridyl 2-((cyclopentyl)NHCH$_2$)-1-imidazolyl
479. 3-pyridyl 2-((cyclopentyl)$_2$NCH$_2$)-1-imidazolyl
480. 3-pyridyl 2-((cyclohexyl)NHCH$_2$)-1-imidazolyl
481. 3-pyridyl 2-((cyclohexyl)$_2$NCH$_2$)-1-imidazolyl
482. 2-pyrimidyl 2-(NH$_2$SO$_2$)phenyl
483. 2-pyrimidyl 2-(CH$_3$SO$_2$)phenyl
484. 2-pyrimidyl 3-NH$_2$SO$_{2-4}$-pyridyl
485. 2-pyrimidyl 3-CH$_3$SO$_{2-4}$-pyridyl
486. 2-pyrimidyl 2-(CH$_3$NH)phenyl
487. 2-pyrimidyl 3-((CH$_3$)$_2$NCH$_2$)-4-pyridyl
488. 2-pyrimidyl 2-(N-(3-R—HO-pyrrolidinyl)CH$_2$)phenyl
489. 2-pyrimidyl 2-(N-(4-HO-piperidinyl)CH$_2$)phenyl
490. 2-pyrimidyl 2-((CH$_3$)$_2$NCH$_2$)phenyl
491. 2-pyrimidyl 2-((CH$_3$)NHCH$_2$)phenyl
492. 2-pyrimidyl 2-((CH$_3$CH$_2$)NHCH$_2$)phenyl
493. 2-pyrimidyl 2-((CH$_3$CH$_2$)$_2$NCH$_2$)phenyl
494. 2-pyrimidyl 2-((CH$_3$CH$_2$)N(CH$_3$)CH$_2$)phenyl
495. 2-pyrimidyl 2-(((CH$_3$)$_2$CH)NHCH$_2$)phenyl
496. 2-pyrimidyl 2-(((CH$_3$)$_2$CH)$_2$NCH$_2$)phenyl
497. 2-pyrimidyl 2-((cyclopropyl)NHCH$_2$)phenyl
498. 2-pyrimidyl 2-((cyclopropyl)$_2$NCH$_2$)phenyl
499. 2-pyrimidyl 2-((cyclobutyl)NHCH$_2$)phenyl
500. 2-pyrimidyl 2-((cyclobutyl)$_2$NCH$_2$)phenyl
501. 2-pyrimidyl 2-((cyclopentyl)NHCH$_2$)phenyl
502. 2-pyrimidyl 2-((cyclopentyl)$_2$NCH$_2$)phenyl
503. 2-pyrimidyl 2-((cyclohexyl)NHCH$_2$)phenyl
504. 2-pyrimidyl 2-((cyclohexyl)$_2$NCH$_2$)phenyl
505. 2-pyrimidyl 1-CH$_{3-2}$-imidazolyl
506. 2-pyrimidyl 2-CH$_{3-1}$-imidazolyl
507. 2-pyrimidyl 2-((CH$_3$)$_2$NCH$_2$)-1-imidazolyl
508. 2-pyrimidyl 2-((CH$_3$)NHCH$_2$)-1-imidazolyl
509. 2-pyrimidyl 2-((CH$_3$CH$_2$)NHCH$_2$)-1-i-midazolyl
510. 2-pyrimidyl 2-((CH$_3$CH$_2$)$_2$NCH$_2$)-1-imidazolyl
511. 2-pyrimidyl 2-((CH$_3$CH$_2$)N(CH$_3$)CH$_2$)-1-imidazolyl
512. 2-pyrimidyl 2-(((CH$_3$)$_2$CH)NHCH$_2$)-1-imidazolyl
513. 2-pyrimidyl 2-(((CH$_3$)$_2$CH)$_2$NCH$_2$)-1-imidazolyl
514. 2-pyrimidyl 2-((cyclopropyl)NHCH$_2$)-1-imidazolyl
515. 2-pyrimidyl 2-((cyclopropyl)$_2$NCH$_2$)-1-imidazolyl
516. 2-pyrimidyl 2-((cyclobutyl)NHCH$_2$)-1-imidazolyl
517. 2-pyrimidyl 2-((cyclobutyl)$_2$NCH$_2$)-1-imidazolyl
518. 2-pyrimidyl 2-((cyclopentyl)NHCH$_2$)-1-imidazolyl
519. 2-pyrimidyl 2-((cyclopentyl)$_2$NCH$_2$)-1-imidazolyl
520. 2-pyrimidyl 2-((cyclohexyl)NHCH$_2$)-1-imidazolyl
521. 2-pyrimidyl 2-((cyclohexyl)$_2$NCH$_2$)-1-imidazolyl
522. 5-pyrimidyl 2-(NH$_2$SO$_2$)phenyl
523. 5-pyrimidyl 2-(CH$_3$SO$_2$)phenyl
524. 5-pyrimidyl 3-NH$_2$SO$_{2-4}$-pyridyl
525. 5-pyrimidyl 3-CH$_3$SO$_{2-4}$-pyridyl
526. 5-pyrimidyl 2-(CH$_3$NH)phenyl
527. 5-pyrimidyl 3-((CH$_3$)$_2$NCH$_2$)-4-pyridyl
528. 5-pyrimidyl 2-(N-(3-R—HO-pyrrolidinyl)CH$_2$)phenyl
529. 5-pyrimidyl 2-(N-(4-HO-piperidinyl)CH$_2$)phenyl
530. 5-pyrimidyl 2-((CH$_3$)$_2$NCH$_2$)phenyl
531. 5-pyrimidyl 2-((CH$_3$)NHCH$_2$)phenyl
532. 5-pyrimidyl 2-((CH$_3$CH$_2$)NHCH$_2$)phenyl
533. 5-pyrimidyl 2-((CH$_3$CH$_2$)$_2$NCH$_2$)phenyl
534. 5-pyrimidyl 2-((CH$_3$CH$_2$)N(CH$_3$)CH$_2$)phenyl
535. 5-pyrimidyl 2-(((CH$_3$)$_2$CH)NHCH$_2$)phenyl
536. 5-pyrimidyl 2-(((CH$_3$)$_2$CH)$_2$NCH$_2$)phenyl
537. 5-pyrimidyl 2-((cyclopropyl)NHCH$_2$)phenyl
538. 5-pyrimidyl 2-((cyclopropyl)$_2$NCH$_2$)phenyl
539. 5-pyrimidyl 2-((cyclobutyl)NHCH$_2$)phenyl
540. 5-pyrimidyl 2-((cyclobutyl)$_2$NCH$_2$)phenyl
541. 5-pyrimidyl 2-((cyclopentyl)NHCH$_2$)phenyl
542. 5-pyrimidyl 2-((cyclopentyl)$_2$NCH$_2$)phenyl
543. 5-pyrimidyl 2-((cyclohexyl)NHCH$_2$)phenyl
544. 5-pyrimidyl 2-((cyclohexyl)$_2$NCH$_2$)phenyl
545. 5-pyrimidyl 1-CH$_{3-2}$-imidazolyl
546. 5-pyrimidyl 2-CH$_{3-1}$-imidazolyl
547. 5-pyrimidyl 2-((CH$_3$)$_2$NCH$_2$)-1-imidazolyl
548. 5-pyrimidyl 2-((CH$_3$)NHCH$_2$)-1-imidazolyl
549. 5-pyrimidyl 2-((CH$_3$CH$_2$)NHCH$_2$)-1-imidazolyl
550. 5-pyrimidyl 2-((CH$_3$CH$_2$)$_2$NCH$_2$)-1-imidazolyl
551. 5-pyrimidyl 2-((CH$_3$CH$_2$)N(CH$_3$)CH$_2$)-1-imidazolyl
552. 5-pyrimidyl 2-(((CH$_3$)$_2$CH)NHCH$_2$)-1-imidazolyl
553. 5-pyrimidyl 2-(((CH$_3$)$_2$CH)$_2$NCH$_2$)-1-imidazolyl
554. 5-pyrimidyl 2-((cyclopropyl)NHCH$_2$)-1-imidazolyl
555. 5-pyrimidyl 2-((cyclopropyl)$_2$NCH$_2$)-1-imidazolyl
556. 5-pyrimidyl 2-((cyclobutyl)NHCH$_2$)-1-imidazolyl
557. 5-pyrimidyl 2-((cyclobutyl)$_2$NCH$_2$)-1-imidazolyl
558. 5-pyrimidyl 2-((cyclopentyl)NHCH$_2$)-1-imidazolyl
559. 5-pyrimidyl 2-((cyclopentyl)$_2$NCH$_2$)-1-imidazolyl
560. 5-pyrimidyl 2-((cyclohexyl)NHCH$_2$)-1-imidazolyl
561. 5-pyrimidyl 2-((cyclohexyl)$_2$NCH$_2$)-1-imidazolyl
562. 2-Cl-phenyl 2-(NH$_2$So$_2$)phenyl
563. 2-Cl-phenyl 2-(CH$_3$SO$_2$)phenyl
564. 2-Cl-phenyl 3-NH$_2$SO$_{2-4}$-pyridyl
565. 2-Cl-phenyl 3-CH$_3$SO$_{2-4}$-pyridyl
566. 2-Cl-phenyl 2-(CH$_3$NH)phenyl
567. 2-Cl-phenyl 3-((CH$_3$)$_2$NCH$_2$)-4-pyridyl
568. 2-Cl-phenyl 2-(N-(3-R-HO-pyrrolidinyl)CH$_2$)phenyl
569. 2-Cl-phenyl 2-(N-(4-HO-piperidinyl)CH$_2$)phenyl
570. 2-Cl-phenyl 2-((CH$_3$)$_2$NCH$_2$)phenyl
571. 2-Cl-phenyl 2-((CH$_3$)NHCH$_2$)phenyl
572. 2-Cl-phenyl 2-((CH$_3$CH$_2$)NHCH$_2$)phenyl
573. 2-Cl-phenyl 2-((CH$_3$CH$_2$)$_2$NCH$_2$)phenyl
574. 2-Cl-phenyl 2-((CH$_3$CH$_2$)N(CH$_3$)CH$_2$)phenyl
575. 2-Cl-phenyl 2-(((CH$_3$)$_2$CH)NHCH$_2$)phenyl
576. 2-Cl-phenyl 2-(((CH$_3$)$_2$CH)$_2$NCH$_2$)phenyl
577. 2-Cl-phenyl 2-((cyclopropyl)NHCH$_2$)phenyl
578. 2-Cl-phenyl 2-((cyclopropyl)$_2$NCH$_2$)phenyl
579. 2-Cl-phenyl 2-((cyclobutyl)NHCH$_2$)phenyl
580. 2-Cl-phenyl 2-((cyclobutyl)$_2$NCH$_2$)phenyl
581. 2-Cl-phenyl 2-((cyclopentyl)NHCH$_2$)phenyl
582. 2-Cl-phenyl 2-((cyclopentyl)$_2$NCH$_2$)phenyl
583. 2-Cl-phenyl 2-((cyclohexyl)NHCH$_2$)phenyl
584. 2-Cl-phenyl 2-((cyclohexyl)$_2$NCH$_2$)phenyl
585. 2-Cl-phenyl 1-CH$_{3-2}$-imidazolyl
586. 2-Cl-phenyl 2-CH$_{3-1}$-imidazolyl
587. 2-Cl-phenyl 2-((CH$_3$)$_2$NCH$_2$)-1-imidazolyl
588. 2-Cl-phenyl 2-((CH$_3$)NHCH$_2$)-1-imidazolyl
589. 2-Cl-phenyl 2-((CH$_3$CH$_2$)NHCH$_2$)-1-imidazolyl
590. 2-Cl-phenyl 2-((CH$_3$CH$_2$)$_2$NCH$_2$)-1-imidazolyl
591. 2-Cl-phenyl 2-((CH$_3$CH$_2$)N(CH$_3$)CH$_2$)-1-imidazolyl
592. 2-Cl-phenyl 2-(((CH$_3$)$_2$C)NH)CH$_2$)-1-imidazolyl
593. 2-Cl-phenyl 2-(((CH$_3$)$_2$CH)$_2$NCH$_2$)-1-imidazolyl
594. 2-Cl-phenyl 2-((cyclopropyl)NHCH$_2$)-1-imidazolyl
595. 2-Cl-phenyl 2-((cyclopropyl)$_2$NCH$_2$)-1-imidazolyl
596. 2-Cl-phenyl 2-((cyclobutyl)NHCH$_2$)-1-imidazolyl
597. 2-Cl-phenyl 2-((cyclobutyl)$_2$NCH$_2$)-1-imidazolyl
598. 2-Cl-phenyl 2-((cyclopentyl)NHCH$_2$)-1-imidazolyl
599. 2-Cl-phenyl 2-((cyclopentyl)$_2$NCH$_2$)-1-imidazolyl
600. 2-Cl-phenyl 2-((cyclohexyl)NHCH$_2$)-1-imidazolyl 601. 2-Cl-phenyl 2-((cyclohexyl)$_2$NCH$_2$)-1-imidazolyl
602. 2-F-phenyl 2-(NH$_2$SO$_2$)phenyl
603. 2-F-phenyl 2-(CH$_3$SO$_2$)phenyl
604. 2-F-phenyl 3-NH$_2$SO$_{2-4}$-pyridyl
605. 2-F-phenyl 3-CH$_3$SO$_{2-4}$-pyridyl
606. 2-F-phenyl 2-(CH$_3$NH)phenyl
607. 2-F-phenyl 3-((CH$_3$)$_2$NCH$_2$)-4-pyridyl
608. 2-F-phenyl 2-(N-(3-R—HO-pyrrolidinyl)CH$_2$)phenyl
609. 2-F-phenyl 2-(N-(4-HO-piperidinyl)CH$_2$)phenyl
610. 2-F-phenyl 2-((CH$_3$)$_2$NCH$_2$)phenyl
611. 2-F-phenyl 2-((CH$_3$)NHCH$_2$)phenyl
612. 2-F-phenyl 2-((CH$_3$CH$_2$)NHCH$_2$)phenyl
613. 2-F-phenyl 2-((CH$_3$CH$_2$)$_2$NCH$_2$)phenyl
614. 2-F-phenyl 2-((CH$_3$CH$_2$)N(CH$_3$)CH$_2$)phenyl
615. 2-F-phenyl 2-(((CH$_3$)$_2$CH)NHCH$_2$)phenyl
616. 2-F-phenyl 2-(((CH$_3$)$_2$CH)$_2$NCH$_2$)phenyl
617. 2-F-phenyl 2-((cyclopropyl)NHCH$_2$)phenyl
618. 2-F-phenyl 2-((cyclopropyl)$_2$NCH$_2$)phenyl
619. 2-F-phenyl 2-((cyclobutyl)NHCH$_2$)phenyl
620. 2-F-phenyl 2-((cyclobutyl)$_2$NCH$_2$)phenyl
621. 2-F-phenyl 2-((cyclopentyl)NHCH$_2$)phenyl
622. 2-F-phenyl 2-((cyclopentyl)$_2$NCH$_2$)phenyl
623. 2-F-phenyl 2-((cyclohexyl)NHCH$_2$)phenyl
624. 2-F-phenyl 2-((cyclohexyl)$_2$NCH$_2$)phenyl
625. 2-F-phenyl 1-CH$_{3-2}$-imidazolyl
626. 2-F-phenyl 2-CH$_{3-1}$-imidazolyl
627. 2-F-phenyl 2-((CH$_3$)$_2$NCH$_2$)-1-imidazolyl
628. 2-F-phenyl 2-((CH$_3$)NHCH$_2$)-1-imidazolyl
629. 2-F-phenyl 2-((CH$_3$CH$_2$)NHCH$_2$)-1-imidazolyl
630. 2-F-phenyl 2-((CH$_3$CH$_2$)$_2$NCH$_2$)-1-imidazolyl
631. 2-F-phenyl 2-((CH$_3$CH$_2$)N(CH$_3$)CH$_2$)-1-imidazolyl
632. 2-F-phenyl 2-((((CH$_3$)$_2$CH)NHCH$_2$)-1-imidazolyl
633. 2-F-phenyl 2-(((CH$_3$)$_2$CH)$_2$NCH$_2$)-1-imidazolyl
634. 2-F-phenyl 2-((cyclopropyl)NHCH$_2$)-1-imidazolyl
635. 2-F-phenyl 2-((cyclopropyl)$_2$NCH$_2$)-1-imidazolyl
636. 2-F-phenyl 2-((cyclobutyl)NHCH$_2$)-1-imidazolyl
637. 2-F-phenyl 2-((cyclobutyl)$_2$NCH$_2$)-1-imidazolyl
638. 2-F-phenyl 2-((cyclopentyl)NHCH$_2$)-1-imidazolyl
639. 2-F-phenyl 2-((cyclopentyl)$_2$NCH$_2$)-1-imidazolyl
640. 2-F-phenyl 2-((cyclohexyl)NHCH$_2$)-1-imidazolyl
641. 2-F-phenyl 2-((cyclohexyl)$_2$NCH$_2$)-1-imidazolyl
642. 2,6-diF-phenyl 2-(NH$_2$SO$_2$)phenyl
643. 2,6-diF-phenyl 2-(CH$_3$SO$_2$)phenyl
644. 2,6-diF-phenyl 3-NH$_2$SO$_{2-4}$-pyridyl
645. 2,6-diF-phenyl 3-CH$_3$SO$_{2-4}$-pyridyl
646. 2,6-diF-phenyl 2-(CH$_3$NH)phenyl
647. 2,6-diF-phenyl 3-((CH$_3$)$_2$NCH$_2$)-4-pyridyl
648. 2,6-diF-phenyl 2-(N-(3-R—HO-pyrrolidinyl)CH$_2$)phenyl
649. 2,6-diF-phenyl 2-(N-(4-HO-piperidinyl)CH$_2$)phenyl
650. 2,6-diF-phenyl 2-((CH$_3$)$_2$NCH$_2$)phenyl
651. 2,6-diF-phenyl 2-((CH$_3$)NHCH$_2$)phenyl
652. 2,6-diF-phenyl 2-((CH$_3$CH$_2$)NHCH$_2$)phenyl
653. 2,6-diF-phenyl 2-((CH$_3$CH$_2$)$_2$NCH$_2$)phenyl
654. 2,6-diF-phenyl 2-((CH$_3$CH$_2$)N(CH$_3$)CH$_2$)phenyl
655. 2,6-diF-phenyl 2-(((CH$_3$)$_2$CH) NHCH$_2$)phenyl
656. 2,6-diF-phenyl 2-(((CH$_3$)$_2$CH)$_2$NCH$_2$)phenyl
657. 2,6-diF-phenyl 2-((cyclopropyl)NHCH$_2$)phenyl
658. 2,6-diF-phenyl 2-((cyclopropyl)$_2$NCH$_2$)phenyl
659. 2,6-diF-phenyl 2-((cyclobutyl)NHCH$_2$)phenyl
660. 2,6-diF-phenyl 2-((cyclobutyl)$_2$NCH$_2$)phenyl
661. 2,6-diF-phenyl 2-((cyclopentyl)NHCH$_2$)phenyl
662. 2,6-diF-phenyl 2-((cyclopentyl)$_2$NCH$_2$)phenyl
663. 2,6-diF-phenyl 2-((cyclohexyl)NHCH$_2$)phenyl
664. 2,6-diF-phenyl 2-((cyclohexyl)$_2$NCH$_2$)phenyl
665. 2,6-diF-phenyl 1-CH$_{3-2}$-imidazolyl
666. 2,6-diF-phenyl 2-CH$_{3-1}$-imidazolyl
667. 2,6-diF-phenyl 2-((CH$_3$)$_2$NCH$_2$)-1-imidazolyl
668. 2,6-diF-phenyl 2-((CH$_3$)NHCH$_2$)-1-imidazolyl
669. 2,6-diF-phenyl 2-((CH$_3$CH$_2$)NHCH$_2$)-1-imidazolyl
670. 2,6-diF-phenyl 2-((CH$_3$CH$_2$)$_2$NCH$_2$)-1-imidazolyl
671. 2,6-diF-phenyl 2-((CH$_3$CH$_2$)N(CH$_3$)CH$_2$)-1-imidazolyl
672. 2,6-diF-phenyl 2-(((CH$_3$)$_2$CH)NHCH$_2$)-1-imidazolyl
673. 2,6-diF-phenyl 2-(((CH$_3$)$_2$CH)$_2$NCH$_2$)-1-imidazolyl
674. 2,6-diF-phenyl 2-((cyclopropyl)NHCH$_2$)-1-imidazolyl
675. 2,6-diF-phenyl 2-((cyclopropyl)$_2$NCH$_2$)-1-imidazolyl
676. 2,6-diF-phenyl 2-((cyclobutyl)NHCH$_2$)-1-imidazolyl
677. 2,6-diF-phenyl 2-((cyclobutyl)$_2$NCH$_2$)-1-imidazolyl
678. 2,6-diF-phenyl 2-((cyclopentyl)NHCH$_2$)-1-imidazolyl
679. 2,6-diF-phenyl 2-((cyclopentyl)$_2$NCH$_2$)-1-imidazolyl
680. 2,6-diF-phenyl 2-((cyclohexyl)NHCH$_2$)-1-imidazolyl
681. 2,6-diF-phenyl 2-((cyclohexyl)$_2$NCH$_2$)-1-imidazolyl
682. piperidinyl 2-(NH$_2$SO$_2$)phenyl
683. piperidinyl 2-(CH$_3$SO$_2$)phenyl
684. piperidinyl 3-NH$_2$SO$_{2-4}$-pyridyl
685. piperidinyl 3-CH$_3$SO$_{2-4}$-pyridyl
686. piperidinyl 2-(CH$_3$NH)phenyl
687. piperidinyl 3-((CH$_3$)$_2$NCH$_2$)-4-pyridyl
688. piperidinyl 2-(N-(3-R—HO-pyrrolidinyl)CH$_2$)phenyl
689. piperidinyl 2-(N-(4-HO-piperidinyl)CH$_2$)phenyl
690. piperidinyl 2-((CH$_3$)$_2$NCH$_2$)phenyl
691. piperidinyl 2-((CH$_3$)NHCH$_2$)phenyl
692. piperidinyl 2-((CH$_3$CH$_2$)NHCH$_2$)phenyl
693. piperidinyl 2-((CH$_3$CH$_2$)$_2$NCH$_2$)phenyl
694. piperidinyl 2-((CH$_3$CH$_2$)N(CH$_3$)CH$_2$)phenyl
695. piperidinyl 2-(((CH$_3$)$_2$CH)NHCH$_2$)phenyl
696. piperidinyl 2-(((CH$_3$)$_2$CH)$_2$NCH$_2$)phenyl
697. piperidinyl 2-((cyclopropyl)NHCH$_2$)phenyl
698. piperidinyl 2-((cyclopropyl)$_2$NCH$_2$)phenyl
699. piperidinyl 2-((cyclobutyl)NHCH$_2$)phenyl
700. piperidinyl 2-((cyclobutyl)$_2$NCH$_2$)phenyl
701. piperidinyl 2-((cyclopentyl)NHCH$_2$)phenyl
702. piperidinyl 2-((cyclopentyl)$_2$NCH$_2$)phenyl
703. piperidinyl 2-((cyclohexyl)NHCH$_2$)phenyl
704. piperidinyl 2-((cyclohexyl)$_2$NCH$_2$)phenyl
705. piperidinyl 1-CH$_{3-2}$-imidazolyl
706. piperidinyl 2-CH$_{3-1}$-imidazolyl
707. piperidinyl 2-((CH$_3$)$_2$NCH$_2$)-1-imidazolyl
708. piperidinyl 2-((CH$_3$)NHCH$_2$)-1-imidazolyl
709. piperidinyl 2-((CH$_3$CH$_2$)NHCH$_2$)-1-imidazolyl
710. piperidinyl 2-((CH$_3$CH$_2$)$_2$NCH$_2$)-1-imidazolyl
711. piperidinyl 2-((CH$_3$CH$_2$)N(CH$_3$)CH$_2$)-1-imidazolyl
712. piperidinyl 2-(((CH$_3$)$_2$CH)NHCH$_2$)-1-imidazolyl
713. piperidinyl 2-(((CH$_3$)$_2$CH)$_2$NCH$_2$)-1-imidazolyl
714. piperidinyl 2-((cyclopropyl)NHCH$_2$)-1-imidazolyl
715. piperidinyl 2-((cyclopropyl)$_2$NCH$_2$)-1-imidazolyl
716. piperidinyl 2-((cyclobutyl)NHCH$_2$)-1-imidazolyl
717. piperidinyl 2-((cyclobutyl)$_2$NCH$_2$)-1-imidazolyl
718. piperidinyl 2-((cyclopentyl)NHCH$_2$)-1-imidazolyl
719. piperidinyl 2-((cyclopentyl)$_2$NCH$_2$)-1-imidazolyl
720. piperidinyl 2-((cyclohexyl)NHCH$_2$)-1-imidazolyl
721. piperidinyl 2-((cyclohexyl)$_2$NCH2)-1-imidazolyl
722. piperidinyl isopropyl Examples 362–6498 use the corresponding A and B groups from Examples 1–361 and the recited G group.

Examples 362–722, G is 3-aminoindazol-6-yl;
Examples 723–1083, G is 3-amidophenyl;
Examples 1084–1444, G is 2-(aminomethyl)phenyl;
Examples 1445–1805, G is 3-(aminomethyl)phenyl;
Examples 1806–2166, G is 2-(aminomethyl)-3-fluorophenyl;
Examples 2167–2527, G is 2-(aminomethyl)-4-fluorophenyl;

Examples 2528–2888, G is 4-Cl-2-pyridyl;
Examples 2889–3249, G is 4-chlorophenyl;
Examples 3250–3610, G is 3-amino-4-chloro-phenyl;
Examples 3611–3971, G is 3-amidino-phenyl;
Examples 3972–4332, G is 1-aminoisoquinolin-6-yl;
Examples 4333–4693, G is 1-aminoisoquinolin-7-yl;
Examples 4694–5054, G is 4-aminoquinazol-6-yl;
Examples 5055–5415, G is 4-aminoquinazol-7-yl;
Examples 5416–5776, G is 3-aminobenzisoxazol-5-yl;
Examples 5777–6137, G is 3-aminobenzisoxazol-6-yl; and,
Examples 6138–6498, G is 3-aminoindazol-5-yl.

Table 5

Examples 1–6498 are the same as in Table 4, except that $R^{1a}$ is $CH_2CH_3$.

Table 6

Examples 1–6498 are the same as in Table 4, except that $R^{1a}$ is $CF_3$.

Table 7

Examples 1–6498 are the same as in Table 4, except that $R^{1a}$ is $SCH_3$.

Table 8

Examples 1–6498 are the same as in Table 4, except that $R^{1a}$ is $SOCH_3$.

Table 9

Examples 1–6498 are the same as in Table 4, except that $R^{1a}$ is $SO_2CH_3$.

Table 10

Examples 1–6498 are the same as in Table 4, except that $R^{1a}$ is Cl.

Table 11

Examples 1–6498 are the same as in Table 4, except that $R^{1a}$ is F.

Table 12

Examples 1–6498 are the same as in Table 4, except that $R^{1a}$ is $CO_2CH_3$.

Table 13

Examples 1–6498 are the same as in Table 4, except that $R^{1a}$ $CH_2OCH_3$.

Table 14

Examples 1–6498 are the same as in Table 4, except that $R^{1a}$ is $CONH_2$.

Table 15

Examples 1–6498 are the same as in Table 4, except that $R^{1a}$ is CN.

Table 16

Examples 1–6498 are the same as in Table 4, except that $R^{1a}$ is $CH_2NH_2$.

Table 17

Examples 1–6498 are the same as in Table 4, except that $R^{1a}$ is $CH_2NHSO_2CH_3$.

Utility

The compounds of this invention are useful as anticoagulants for the treatment or prevention of thromboembolic disorders in mammals. In general, a thromboembolic disorder is a circulatory disease caused by blood clots (i.e., diseases involving platelet activation and/or platelet aggregation). The term "thromboembolic disorders" as used herein includes arterial cardiovascular thromboembolic disorders, venous cardiovascular thromboembolic disorders, arterial cerebrovascular thromboembolic disorders, and venous cerebrovascular thromboembolic disorders. The term "thromboembolic disorders" as used herein includes specific disorders selected from, but not limited to, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous translumianl coronary angioplasty). The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:

$v_o$ is the velocity of the control in the absence of inhibitor;
$v_s$ is the velocity in the presence of inhibitor;
I is the concentration of inhibitor;
$K_i$ is the dissociation constant of the enzyme:inhibitor complex;
S is the concentration of substrate;
$K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine and clopidogrel, including pharmaceutically acceptable salts or prodrugs thereof. Ticlopidine and clopidogrel are also preferred compounds since they are known to be gentle on the gastro-intestinal tract in use. Still other suitable platelet inhibitory agents include IIb/IIIa antagonists, including tirofiban, eptifibatide, and abciximab, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics (or fibrinolytic) agents (or thrombolytics or fibrinolytics), as used herein, denotes agents that lyse blood clots (thrombi). Such agents include tissue plasminogen activator and modified forms thereof, anistreplase, urokinase or streptokinase, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P, and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but ratheR is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Numerous modifications and variations of the present invention are possible in light of the above teachings. It is therefore to be understood that within the scope of the appended claims, the invention may be practiced otherwise that as specifically described herein.

What is claimed is:

1. A compound of formula I:

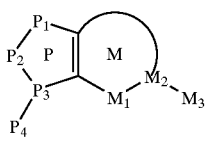

or a stereoisomer or pharmaceutically acceptable salt thereof, wherein;

ring M is substituted with 0–1 $R^{1a}$ and is selected from the group:

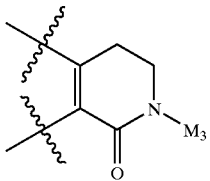 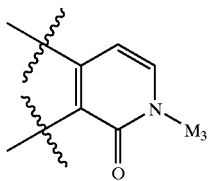

ring P, including $P_1$, $P_2$, $P_3$, and $P_4$ is:

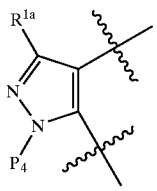

one of $P_4$ and $M_3$ is -Z-A-B and the other -$G_1$-G;
G is a group of formula IIa or IIb:

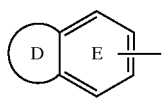

IIa

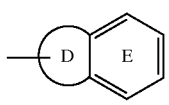

IIb ring D, including the two atoms of Ring E to which it is attached, is a 5–6 membered non-aromatic ring consisting of carbon atoms, 0–1 double bonds, and 0–2 heteroatoms selected from the group consisting of N, O, and $S(O)_p$, and D is substituted with 0–2 R;

alternatively, ring D, including the two atoms of Ring E to which it is attached, is a 5–6 membered aromatic system consisting of carbon atoms and 0–2 heteroatoms selected from the group consisting of N, O, and $S(O)_p$, and D is substituted with 0–2 R;

E is selected from phenyl, pyridyl, pyrimidyl, pyrazinyl, and pyridazinyl, and is substituted with 1–2 R;

alternatively, the bridging portion of ring D is absent, and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–2 R;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$, provided that $S(O)_pR^7$ forms other than $S(O)_2H$ or $S(O)H$;

alternatively, when 2 R groups are attached to adjacent atoms, they combine to form methylenedioxy or ethylenedioxy;

A is selected from:
 $C_{3-10}$ carbocycle substituted with 0–2 $R^4$, and
 5–12 membered heterocycle consisting of: carbon atoms and 1–4 heteroatoms selected from the group consisting of N, O, and $S(O)_p$ substituted with 0–2 $R^4$;

B is selected from phenyl, pyrrolidino, N-pyrrolidino-carbonyl morpholino, N-morpholino-carbonyl, 1,2,3-triazolyl, imidazolyl, and benzimidazolyl, and is substituted with 0–1 $R^{4a}$;

$G_1$ is absent or is selected from $(CR^3R^{3a})_{1-5}$, $(CR^3R^{3a})_{0-2}CR^3=CR^3(CR^3R^{3a})_{0-2}$, $(CR^3R^{3a})_{0-2}C\equiv C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uO(CR^3R^{3a})_w$, $(CR^3R^{3a})_uNR^3(CR^3R^{3a})_w$, $(CR^3R^{3a})_uC(O)NR^3(CR^3R^{3a})_w$, $(CR^3R^{3a})_uNR^3C(O)(CR^3R^{3a})_w$, $(CR^3R^{3a})_uOC(O)NR^3(CR^3R^{3a})_w$, $(CR^3R^{3a})_uNR^3C(O)O(CR^3R^{3a})_w$, $(CR^3R^{3a})_uNR^3C(O)NR^3(CR^3R^{3a})_w$, $(CR^3R^{3a})_uNR^3C(S)NR^3(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^3(CR^3R^{3a})_w$, $(CR^3R^{3a})_uNR^3S(O)_2(CR^3R^{3a})_w$, $(CR^3R^{3a})_uS(O)_2NR^3(CR^3R^{3a})_w$, and $(CR^3R^{3a})_uNR^3S(O)_2NR^3(CR^3R^{3a})_w$, wherein u+w total 0, 1, 2, 3, or 4, provided that $G_1$ does not form a N—N, N—O, N—S, $NCH_2N$, $NCH_2O$, or $NCH_2S$ bond with either group to which it is attached;

Z is selected from a bond, $-(CR^2R^{2a})_{1-4}-$, $(CR^2R^{2a})_qO(CR^2R^{2a})_{q1}$, $(CR^2R^{2a})_qNR^3(CR^2R^{2a})_{q1}$, $(CR^2R^{2a})_qC(O)(CR^2R^{2a})_{q1}$, $(CR^2R^{2a})_qC(O)O(CR^2R^{2a})_{q1}$, $(CR^2R^{2a})_qOC(O)(CR^2R^{2a})_{q1}$, $(CR^2R^{2a})_qC(O)NR^3(CR^2R^{2a})_{q1}$, $(CH_2)_qNR^3C(O)(CR^2R^{2a})_{q1}$, $(CR^2R^{2a})_qOC(O)O(CR^2R^{2a})_{q1}$, $(CH_2)_qOC(O)NR^3(CR^2R^{2a})_{q1}$, $(CR^2R^{2a})_qNR^3C(O)O(CR^2R^{2a})_{q1}$, $(CH_2)_qNR^3C(O)NR^3(CR^2R^{2a})_{q1}$, $(CR^2R^{2a})_qS(CR^2R^{2a})_{q1}$, $(CR^2R^{2a})_qS(O)(CR^2R^{2a})_{q1}$, $(CH_2)_qS(O)_2(CR^2R^{2a})_{q1}$, $(CR^2R^{2a})_qSO_2NR^3(CR^2R^{2a})_{q1}$, $(CH_2)_qNR^3SO_2(CR^2R^{2a})_{q1}$, and $(CR^2R^{2a})_qNR^3SO_2NR^3(CR^2R^{2a})_{q1}$, wherein q+q1 total 0, 1, or 2, provided that Z does not form a N—N, N—O, N—S, $NCH_2N$, $NCH_2O$, or $NCH_2S$ bond with either group to which it is attached;

R$^{1a}$ is selected from H, —(CH$_2$)$_r$—R$^{1b}$, —CH=CH—R$^{1b}$, NCH$_2$R$^{1c}$, OCH$_2$R$^{1c}$, SCH$_2$R$^{1c}$, NH(CH$_2$)$_2$(CH$_2$)$_r$R$^{1b}$, O(CH$_2$)$_2$(CH$_2$)$_r$R$^{1b}$, S(CH$_2$)$_2$(CH$_2$)$_r$R$^{1b}$, S(O)$_p$(CH$_2$)$_r$R$^{1d}$, O(CH$_2$)$_r$R$^{1d}$, NR$^3$(CH$_2$)$_r$R$^{1d}$, OC(O)NR$^3$(CH$_2$)$_r$R$^{1d}$, NR$^3$C(O)NR$^3$(CH$_2$)$_r$R$^{1d}$, NR$^3$C(O)O(CH$_2$)$_r$R$^{1d}$, and NR$^3$C(O)(CH$_2$)$_r$R$^{1d}$, provided that R$^{1a}$ forms other than an N-halo, N—N, N—S, N—O, or N—CN bond;

R$^{1b}$ is selected from H, C$_{1-3}$ alkyl, F, Cl, Br, I, —CN, —CHO, (CF$_2$)$_r$CF$_3$, (CH$_2$)$_r$OR$^2$, NR$^2$R$^{2a}$, C(O)R$^{2c}$, OC(O)R$^2$, (CF$_2$)$_r$CO$_2$R$^{2a}$, S(O)$_p$R$^{2b}$, NR$^2$(CH$_2$)$_r$OR$^2$, C(=NR$^2$C)NR$^2$R$^{2a}$, NR$^2$C(O)R$^{2b}$, NR$^2$C(O)NHR$^{2b}$, NR$^2$C(O)$_2$R$^{2a}$, OC(O)NR$^{2a}$R$^{2b}$, C(O)NR$^2$R$^{2a}$, C(O)NR$^2$(CH$_2$)$_r$OR$^2$, SO$_2$NR$^2$R$^{2a}$, NR$^2$SO$_2$R$^{2b}$, C$_{3-6}$ carbocycle substituted with 0–2 R$^{4a}$, and 5–10 membered heterocycle consisting of carbon atoms and from 1–4 heteroatoms selected from the group consisting of N, O, and S(O)$_p$ substituted with 0–2 R$^{4a}$, provided that R$^{1b}$ forms other than an N-halo, N—N, N—S, N—O, or N—CN bond;

R$^{1c}$ is selected from H, CH(CH$_2$OR$^2$)$_2$, C(O)R$^{2c}$, C(O)NR$^2$R$^{2a}$, S(O)R$^{2b}$, S(O)$_2$R$^{2b}$, and SO$_2$NR$^2$R$^{2a}$;

R$^{1d}$ is selected from C$_{3-6}$ carbocycle substituted with 0–2 R$^{4a}$ and 5–10 membered heterocycle consisting of carbon atoms and from 1–4 heteroatoms selected from the group consisting of N, O, and S(O)$_p$ substituted with 0–2 R$^{4a}$, provided that R$^{id}$ forms other than an N—N, N—S, or N—O bond;

R$^2$, at each occurrence, is selected from H, CF$_3$, C$_{1-6}$ alkyl, benzyl, C$_{3-6}$ carbocycle substituted with 0–2 R$^{4b}$, a C$_{3-6}$ carbocycle-CH$_2$— substituted with 0–2 R$^{4b}$, and 5–6 membered heterocycle consisting of: carbon atoms and 1–4 heteroatoms selected from the group consisting of N, O, and S(O)$_p$ substituted with 0–2 R$^{4b}$;

R$^{2a}$, at each occurrence, is selected from H, CF$_3$, C$_{1-6}$ alkyl, benzyl, C$_{3-6}$ carbocycle substituted with 0–2 R$^{4b}$, and 5–6 membered heterocycle consisting of: carbon atoms and 1–4 heteroatoms selected from the group consisting of N, O, and S(O)$_p$ substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocycle substituted with 0–2 R$^{4b}$, and 5–6 membered heterocycle consisting of: carbon atoms and 1–4 heteroatoms selected from the group consisting of N, O, and S(O)$_p$ substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocycle substituted with 0–2 R$^{4b}$, and 5–6 membered heterocyclic system containing from 1–4 heteroatoms selected from the group consisting of N, O, and S(O)$_p$ substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and consisting of: 0–1 additional heteroatoms selected from the group consisting of N, O, and S(O)$_p$;

R$^3$, at each occurrence, is selected from H, C$_{1-4}$ alkyl, and phenyl;

R$^{3a}$, at each occurrence, is selected from H, C$_{1-4}$ alkyl, benzyl, and phenyl;

R$^{3b}$, at each occurrence, is selected from H, C$_{1-4}$ alkyl, and phenyl;

R$^{3c}$, at each occurrence, is selected from C$_{1-4}$ alkyl, benzyl, and phenyl;

R$^{3d}$, at each occurrence, is selected from H, C$_{1-4}$ alkyl, C$_{1-4}$ alkyl-phenyl, and C(=O)R$^{3c}$;

R$^4$, at each occurrence, is selected from H, =O, (CH$_2$)$_r$OR$^2$, F, Cl, Br, I, C$_{1-4}$ alkyl, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, NR$^2$C(O)NR$^2$R$^{2a}$, C(=NR$^2$)NR$^2$R$^{2a}$, C(=NS(O)$_2$R$^5$)NR$^2$R$^{2a}$, NHC(=NR$^2$)NR$^2$R$^{2a}$, C(O)NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, NR$^2$SO$_2$R$^5$, S(O)$_p$R$^5$, (CF$_2$)$_r$CF$_3$, NCH$_2$R$^{1c}$, OCH$_2$R$^{1c}$, SCH$_2$R$^{1c}$, N(CH$_2$)$_2$(CH$_2$)$_r$R$^{1b}$, O(CH$_2$)$_2$(CH$_2$)$_r$R$^{1b}$, and S(CH$_2$)$_2$(CH$_2$)$_r$R$^{1b}$;

alternatively, one R$^4$ is a 5–6 membered aromatic heterocycle consisting of: carbon atoms and 1–4 heteroatoms selected from the group consisting of N, O, and S(O)$_p$;

R$^{4a}$, at each occurrence, is selected from H, =O, (CH$_2$)$_r$OR$^2$, (CH$_2$)$_r$—F, (CH$_2$)$_r$—Br, (CH$_2$)$_r$—Cl, Cl, Br, F, I, C$_{1-4}$ alkyl, s-CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, (CH$_2$)$_r$N=CHOR$^3$, C(O)NH(CH$_2$)$_2$NR$^2$R$^{2a}$, NR$^2$C(O)NR$^2$R$^{2a}$, C(=NR$^2$)NR$^2$R$^{2a}$, NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, C(O)NHSO$_2$—C$_{1-4}$ alkyl, NR$^2$SO$_2$R$^5$, S(O)$_p$R$^5$, and (CF$_2$)$_r$CF$_3$;

alternatively, one R$^{4a}$ is phenyl substituted with 0–1 R$^5$ or a 5–6 membered aromatic heterocycle consisting of: carbon atoms and 1–4 heteroatoms selected from the group consisting of N, O, and S(O)$_p$ substituted with 0–1 R$^5$;

R$^{4b}$, at each occurrence, is selected from H, =O, (CH$_2$)$_r$OR$^3$, F, Cl, Br, I, C$_{1-4}$ alkyl, —CN, NO$_2$, (CH$_2$)$_r$NR$^3$R$^{3a}$, (CH$_2$)$_r$C(O)R$^3$, (CH$_2$)$_r$C(O)OR$^{3c}$, NR$^3$C(O)R$^{3a}$, C(O)NR$^3$R$^{3a}$, NR$^3$C(O)NR$^3$R$^{3a}$, C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, and (CF$_2$)$_r$CF$_3$;

R$^5$, at each occurrence, is selected from H, C$_{1-6}$ alkyl, =O, (CH$_2$)$_r$OR$^3$, F, Cl, Br, I, C$_{1-4}$ alkyl, —CN, NO$_2$, (CH$_2$)$_r$NR$^3$R$^{3a}$, (CH$_2$)$_r$C(O)R$^3$, (CH$_2$)$_r$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, (CF$_2$)$_r$CF$_3$, phenyl substituted with 0–2 R$^6$, naphthyl substituted with 0–2 R$^6$, and benzyl substituted with 0–2 R$^6$;

R$^6$, at each occurrence, is selected from H, OH, (CH$_2$)$_r$OR$^2$, halo, C$_{1-4}$ alkyl, CN, NO$_2$, (CH$_2$)$_r$NR$^2$R$^{2a}$, (CH$_2$)$_r$ C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkylcarbonyl, C$_{1-6}$ alkoxy, C$_{1-4}$ alkoxycarbonyl, (CH$_2$)$_n$-phenyl, C$_{6-10}$ aryloxy, C$_{6-10}$ aryloxycarbonyl, C$_{6-10}$ arylmethylcarbonyl, C$_{1-4}$ alkylcarbonyloxy C$_{1-4}$ alkoxycarbonyl, C$_{6-10}$ arylcarbonyloxy C$_{1-4}$ alkoxycarbonyl, C$_{1-6}$ alkylaminocarbonyl, phenylaminocarbonyl, and phenyl C$_{1-4}$ alkoxycarbonyl;

R$^8$, at each occurrence, is selected from H, C$_{1-6}$ alkyl, and (CH$_2$)$_n$-phenyl;

alternatively, R$^7$ and R$^8$ combine to form a 5 or 6 membered saturated, ring which contains from 0–1 additional heteroatoms selected from the group consisting of N, O, and S(O)$_p$;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6;

t, at each occurrence, is selected from 0, 1, 2, and 3;

provided that:
(a) when $P_4$ is -Z-A-B and G is substituted with an amidino, guanidino, amino-ethylene, or amino-propylene group, any of which may be substituted or cyclized, then $G_1$ is present or Z is other than a bond or alkylene; and
(b) when $P_4$ is -$G_1$-G and $G_1$ is absent or alkylene, then Z is other than a bond or alkylene.

2. A compound according to claim 1, wherein:

G is selected from the group:

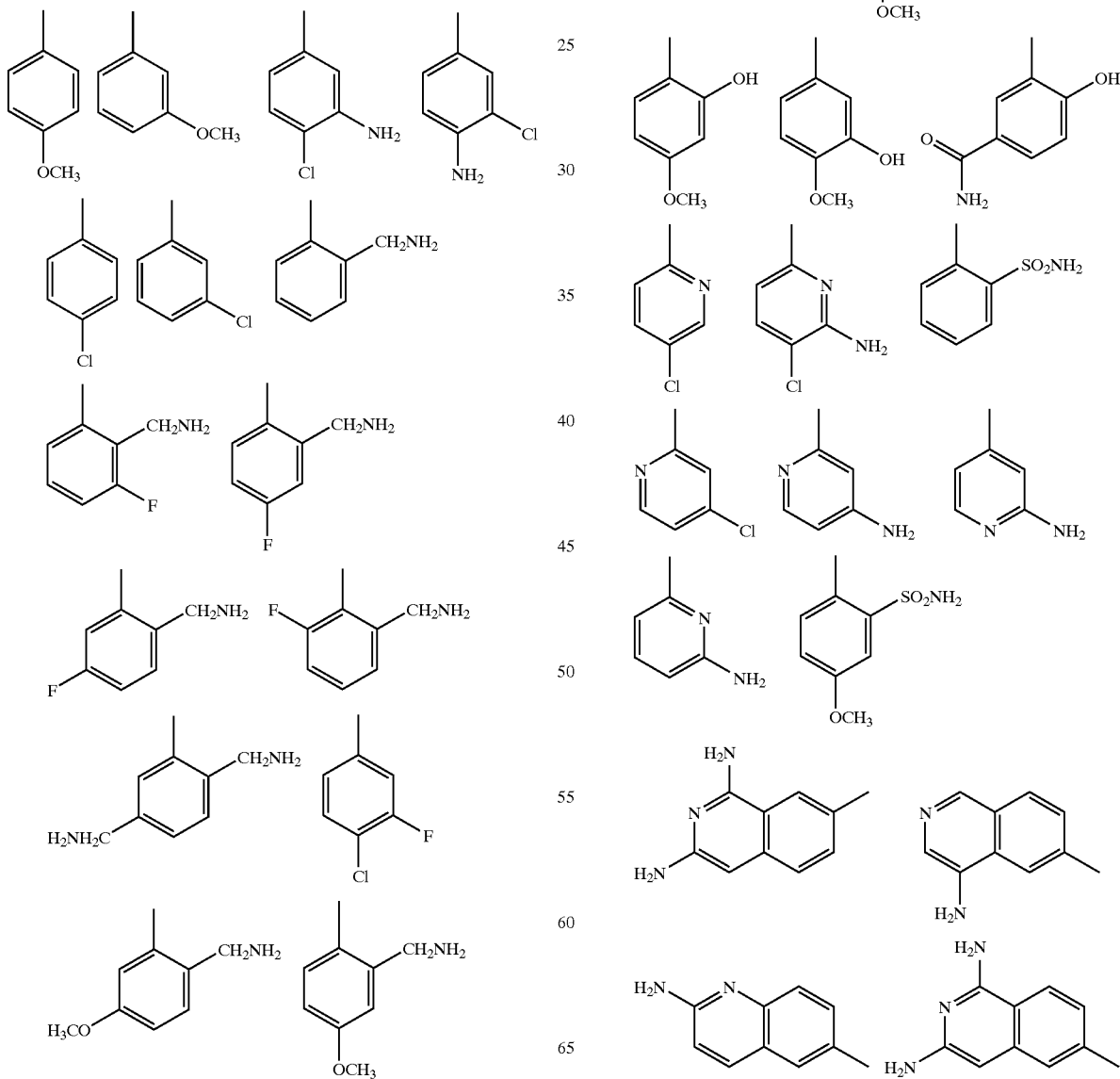

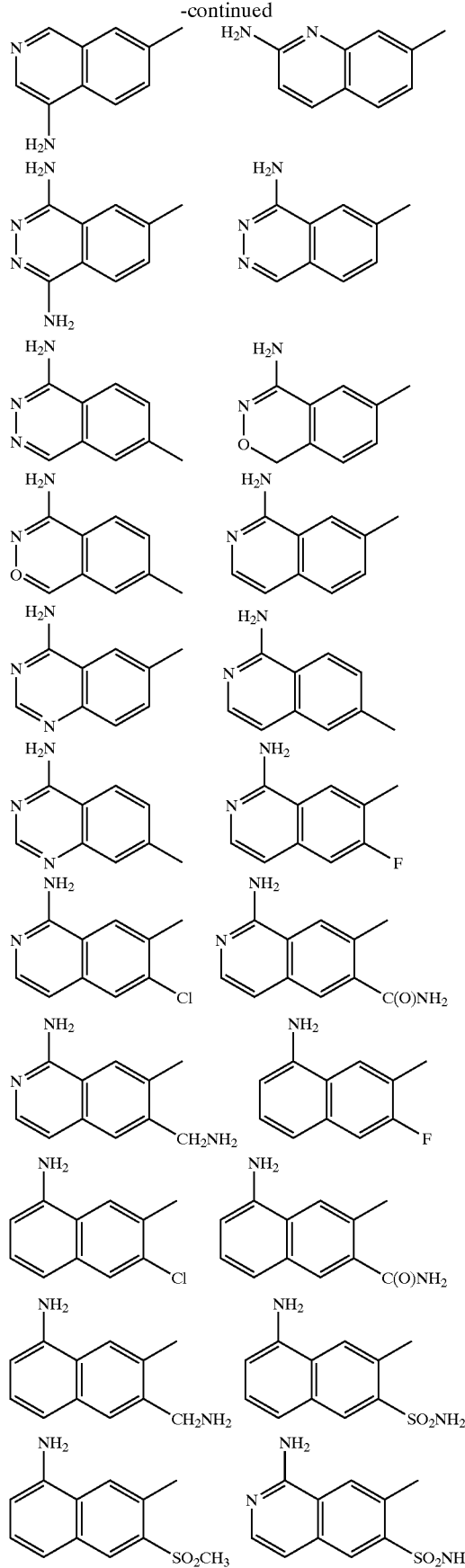
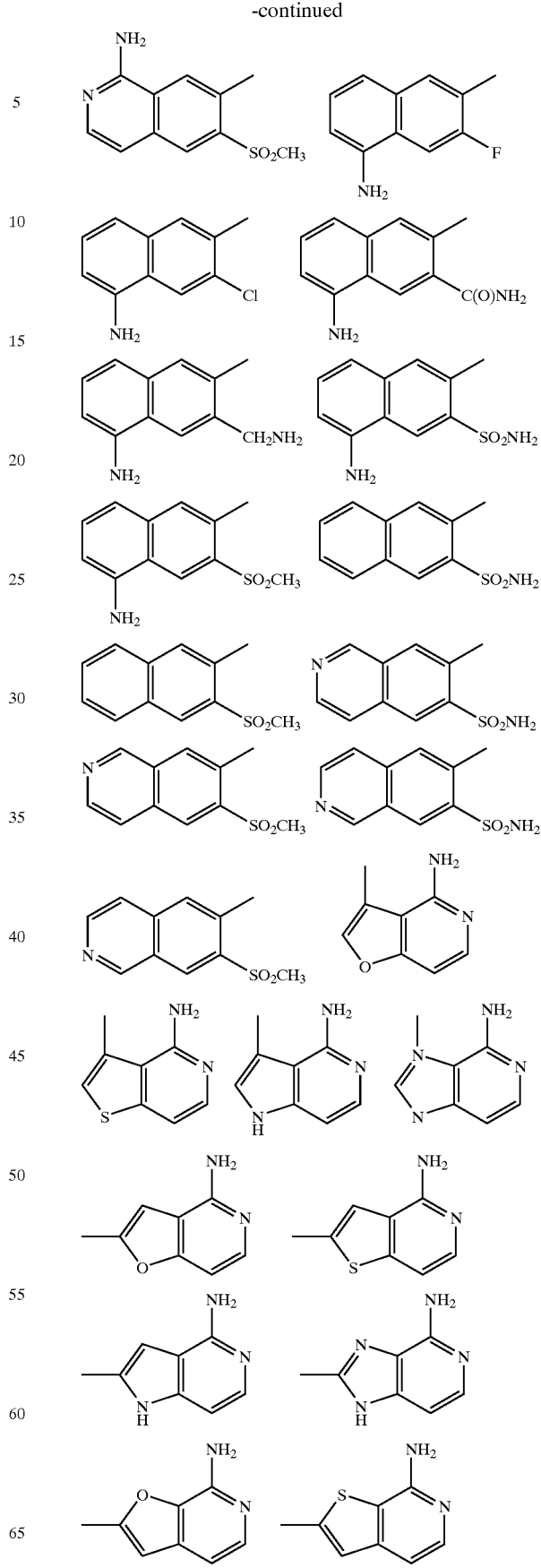

-continued

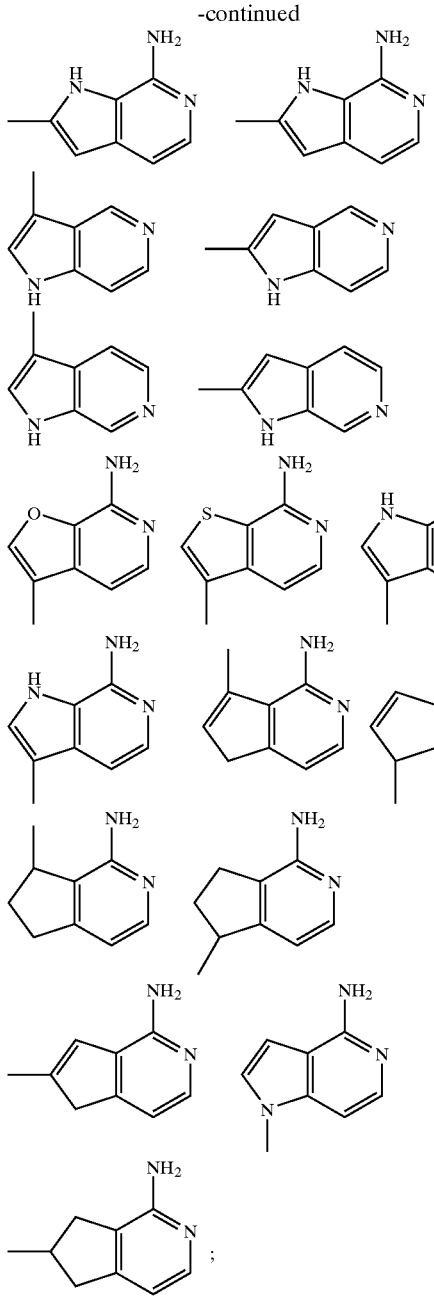

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

$G_1$ is absent or is selected from $(CR^3R^{3a})_{1-3}$, $(CR^3R^{3a})_u C(O)(CR^3R^{3a})_w$, $(CR^3R^{3a})_u O(CR^3R^{3a})_w$, $(CR^3R^{3a})_u NR^3(CR^3CR^{3a})_w$, $(CR^3R^{3a})_u C(O)NR^3(CR^3R^{3a})_w$, $(CR^3R^{3a})_u NR^3 C(O)(CR^3R^{3a})_w$, $(CR^3R^{3a})_u S(CR^3R^{3a})_w$, $(CR^3R^{3a})_u S(O)(CR^3R^{3a})_w$, $(CR^3R^{3a})_u S(O)_2(CR^3R^{3a})_w$, $(CR^3R^{3a})_u S(O)NR^3 (CR^3R^{3a})_w$, and $(CR^3R^{3a})_u S(O)_2NR^3(CR^3R^{3a})_w$, wherein u+w total 0, 1, or 2, provided that $G_1$ does not form a N—N, N—O, N—S, NCH$_2$N, NCH$_2$O, or NCH$_2$S bond with either group to which it is attached; and, Z is selected from a bond, CH$_2$O, OCH$_2$, NH, CH$_2$NH, NHCH$_2$, CH$_2$C(O), C(O)CH$_2$, C(O)NH, NHC(O), CH$_2$S(O)$_2$, S(O)$_2$(CH$_2$), SO$_2$NH, and NHSO$_2$, provided that Z does not form a N—N, N—O, N—S, NCH$_2$N, NCH$_2$O, or NCH$_2$S bond with either group to which it is attached.

3. A compound according to claim 2, wherein:
G is selected from the group:

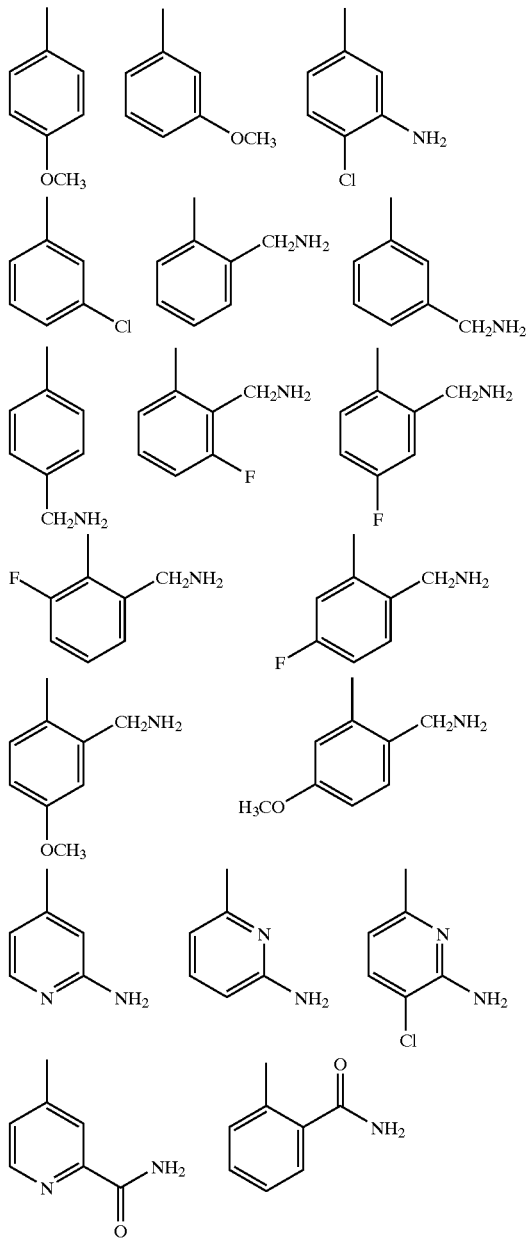

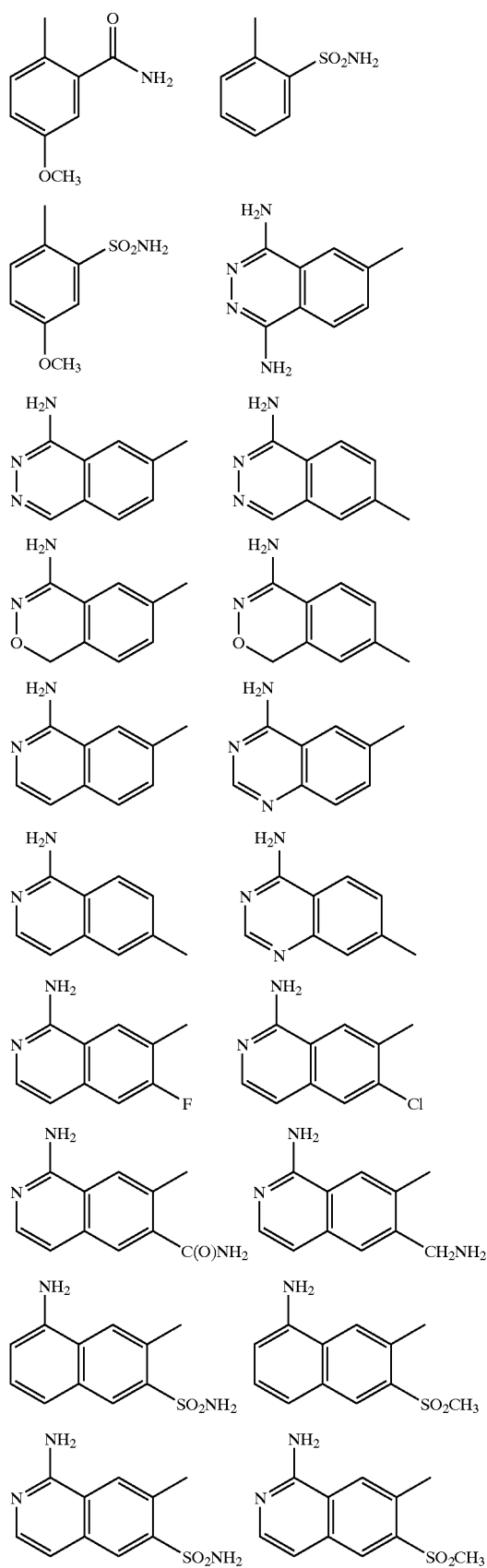
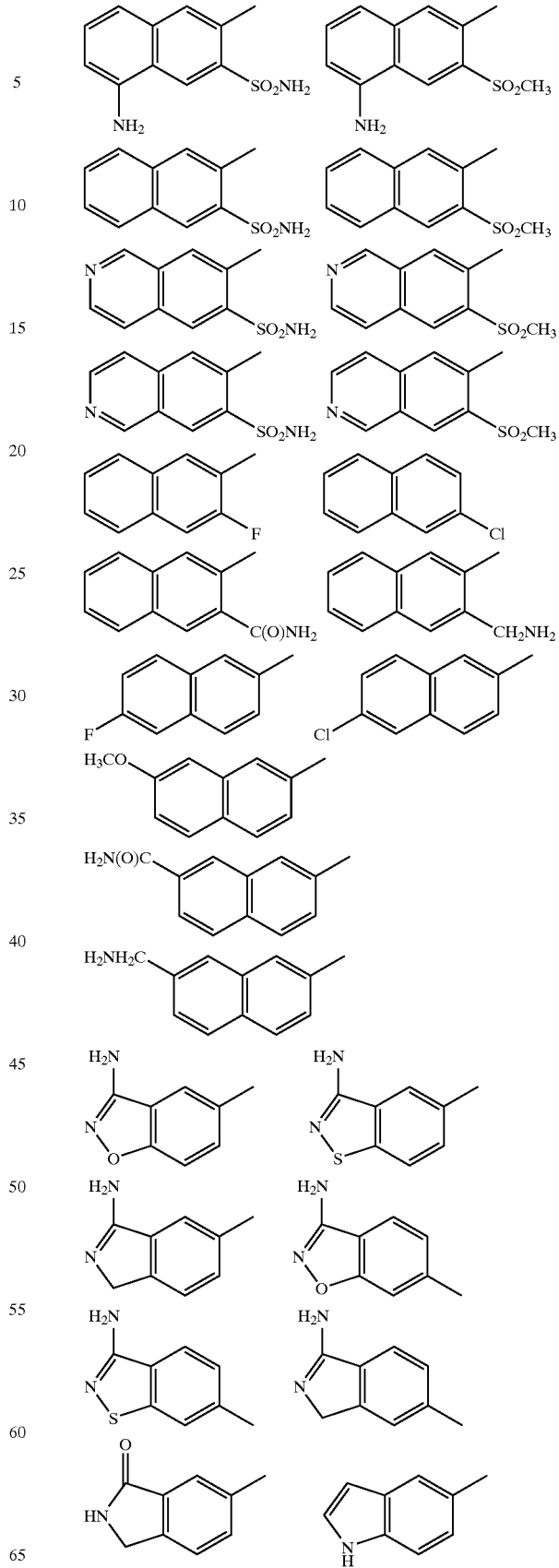

123
-continued

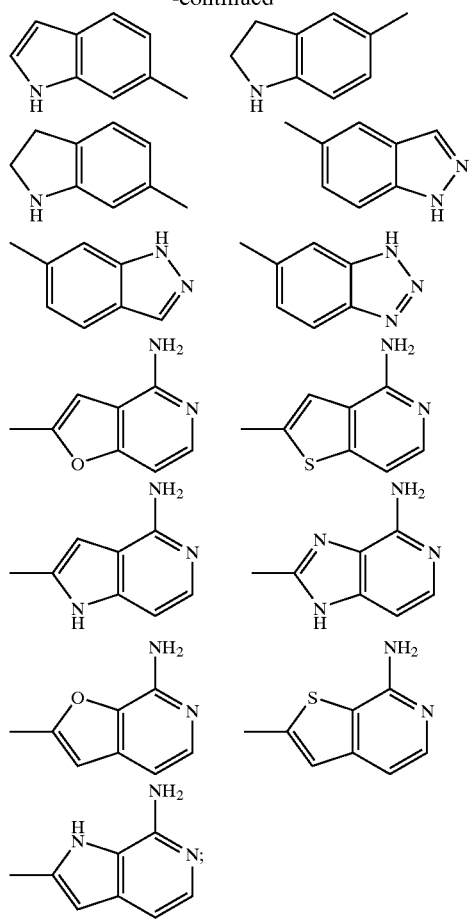

124
-continued

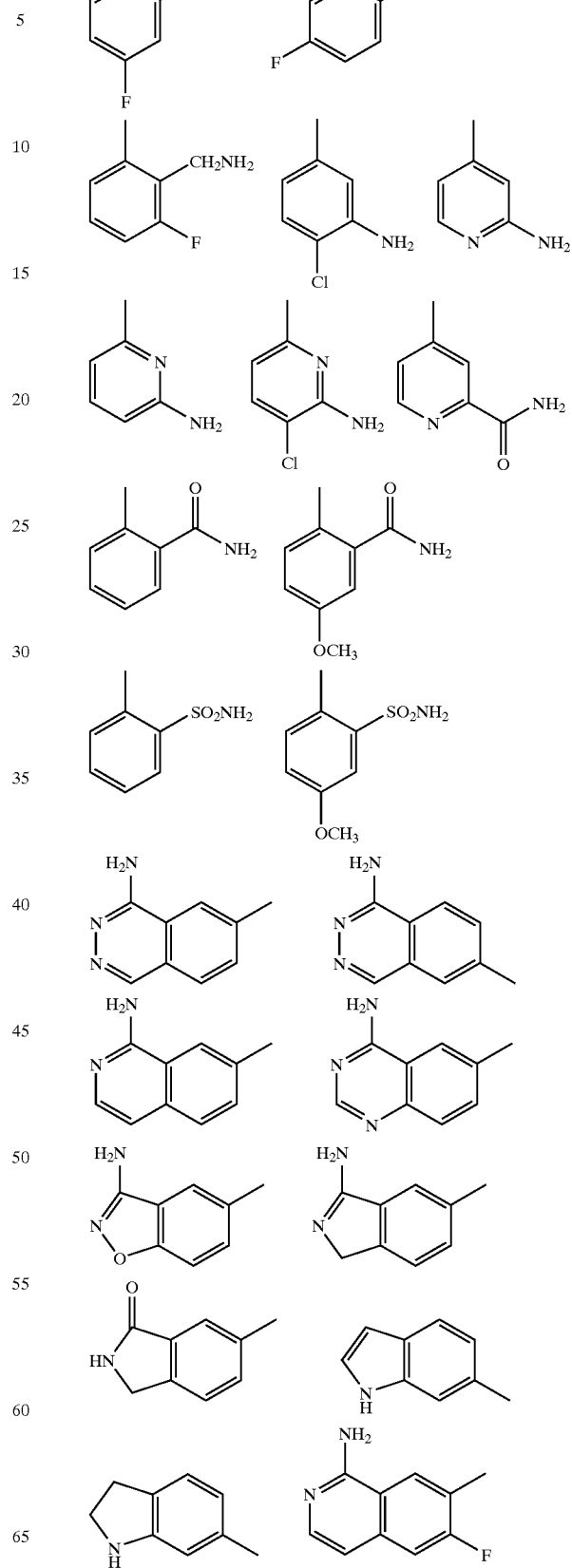

G₁ is absent or is selected from CH₂, CH₂CH₂, CH₂O, OCH₂, NH, CH₂NH, NHCH₂, CH₂C(O), C(O)CH₂, C(O)NH, NHC(O), CH₂S(O)₂, S(O)₂(CH₂), SO₂NH, and NHSO₂, provided that G₁ does not form a N—N, N—O, N—S, NCH₂N, NCH₂O, or NCH₂S bond with either group to which it is attached; and, Z is selected from a bond, CH₂O, OCH₂, NH, CH₂NH, NHCH₂, CH₂C(O), C(O)CH₂, C(O)NH, NHC(O), CH₂S(O)₂, S(O)₂(CH₂), SO₂NH, and NHSO₂, provided that Z does not form a N—N, N—O, N—S, NCH₂N, NCH₂O, or NCH₂S bond with either group to which it is attached.

4. A compound according to claim 3, wherein:
G is selected from:

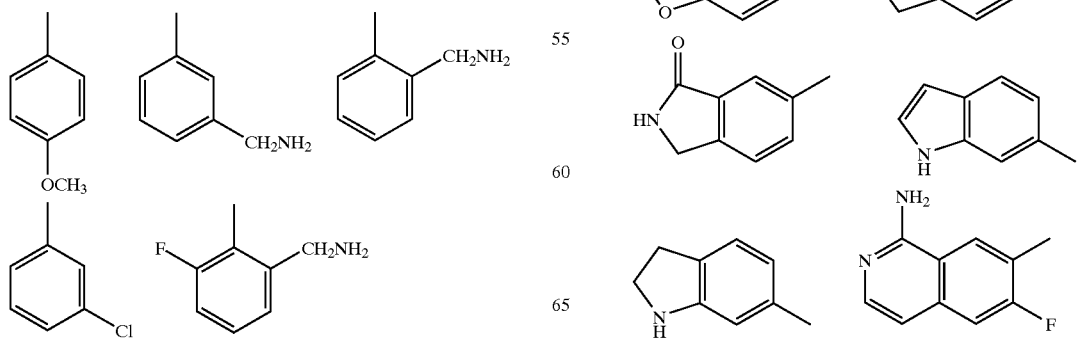

-continued

[Structure: 1-amino-6-chloro-7-methylisoquinoline]
[Structure: 1-amino-6-(C(O)NH2)-7-methylisoquinoline]
[Structure: 1-amino-6-(CH2NH2)-7-methylisoquinoline]; and, $G_1$ is absent.

5. A compound according to claim 4, wherein:

A is selected from phenyl, pyridyl, and pyrimidyl, and is substituted with 0–2 $R^4$;

$R^2$, at each occurrence, is selected from H, $CH_3$, $CH_2CH_3$, cyclopropylmethyl, cyclobutyl, and cyclopentyl;

$R_{2a}$, at each occurrence, is H or $CH_3$;

alternatively, $R^2$ and $R^{2a}$, together with the atom to which they are attached, combine to form pyrrolidine substituted with 0–2 $R^{4b}$ or piperidine substituted with 0–2 $R^{4b}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $(CH_2)_rOR^2$, $(CH_2)_rNR^2R^{2a}$, $S(O)_pR^5$, $SO_2NR^2R^{2a}$, and 1-$CF_3$-tetrazol-2-yl;

$R^{4b}$, at each occurrence, is selected from H, $CH_3$, and OH;

$R^5$, at each occurrence, is selected from $CF_3$, $C_{1-6}$ alkyl, phenyl, and benzyl; and, r, at each occurrence, is selected from 0, 1, and 2.

6. A compound according to claim 5, wherein:

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, and 2-(N-(3-hydroxypyrrolidinyl)methyl)phenyl.

7. A compound selected from the group:

[Two structures: pyrazolo-fused lactam cores with substituents $R^{1a}$, $M_3$, $P_4$]

wherein:

$R^{1a}$ is selected from $CH_3$, $CH_2CH_3$, $CF_3$, $SCH_3$, $SOCH_3$, $SO_2CH_3$, Cl, F, $CO_2CH_3$, $CH_2OCH_3$, $CONH_2$, CN, $CH_2NH_2$, and $CH_2NHSO_2CH_3$;

$P_4$ is Z-A-B;

Z is a bond;

$M_3$ is -$G_1$-G;

$G_1$ is selected from a bond, NHC(O), and C(O)NH;

A is selected from phenyl, 2-pyridyl, 3-pyridyl, 2-pyrimidyl, 5-pyrimidyl, 2-Cl-phenyl, 2-F-pheny, 2,6-diF-phenyl, and piperidinyl;

B is selected from 2-($NH_2SO_2$)phenyl, 2-($CH_3SO_2$)phenyl, 3-$NH_2SO_2$-4-pyridyl, 3-$CH_3SO_2$-4-pyridyl, 2-($CH_3NH$)phenyl, 3-(($CH_3$)$_2NCH_2$)-4-pyridyl, 2-(N-(3-R-HO-pyrrolidinyl)$CH_2$)phenyl, 2-(N-(4-HO-piperidinyl)$CH_2$)phenyl, 2-(($CH_3$)$_2NCH_2$)phenyl, 2-(($CH_3$)$NHCH_2$)phenyl, 2-(($CH_3CH_2$)$NHCH_2$)phenyl, 2-(($CH_3CH_2$)$_2NCH_2$)phenyl, 2-(($CH_3CH_2$)N($CH_3$)$CH_2$)phenyl, 2-((($CH_3$)$_2CH$)$NHCH_2$)phenyl, 2-((($CH_3$)$_2CH$)$_2NCH_2$)phenyl, 2-((cyclopropyl)$NHCH_2$)phenyl, 2-((cyclopropyl)$_2NCH_2$)phenyl, 2-((cyclobutyl)$NHCH_2$)phenyl, 2-((cyclobutyl)$_2NCH_2$)phenyl, 2-((cyclopentyl)$NHCH_2$)phenyl, 2-((cyclopentyl)$_2NCH_2$)phenyl, 2-((cyclohexyl)$NHCH_2$)phenyl, 2-((cyclohexyl)$_2NCH_2$)phenyl, 1-$CH_3$-2-imidazolyl, 2-$CH_3$-1-imidazolyl, 2-(($CH_3$)$_2NCH_2$)-1-imidazolyl, 2-(($CH_3$)$NHCH_2$)-1-imidazolyl, 2-(($CH_3CH_2$)$NHCH_2$)-1-imidazolyl, 2-(($CH_3CH_2$)$_2NCH_2$)-1-imidazolyl, 2-(($CH_3CH_2$)N($CH_3$)$CH_2$)-1-imidazolyl, 2-((($CH_3$)$_2CH$)$NHCH_2$)-1-imidazolyl, 2-((($CH_3$)$_2CH$)$_2NCH_2$)-1-imidazolyl, 2-((cyclopropyl)$NHCH_2$)-1-imidazolyl, 2-((cyclopropyl)$_2NCH_2$)-1-imidazolyl, 2-((cyclobutyl)$NHCH_2$)-1-imidazolyl, 2-((cyclobutyl)$_2NCH_2$)-1-imidazolyl, 2-((cyclopentyl)$NHCH_2$)-1-imidazolyl, 2-((cyclopentyl)$_2NCH_2$)-1-imidazolyl, 2-((cyclohexyl)$NHCH_2$)-1-imidazolyl, and 2-((cyclohexyl)$_2NCH_2$)-1-imidazolyl; and, G is selected from 4-(methoxy)phenyl, 3-aminoindazol-6-yl, 3-aminophenyl, 2-(aminomethyl)phenyl, 3-(aminomethyl)phenyl, 2-(aminomethyl)-3-fluorophenyl, 2-(aminomethyl)-4-fluorophenyl, 4-Cl-2-pyridyl, 4-chlorophyll, 3-amino-4-chloro-phenyl, 3-amidino-phenyl, 1-aminoisoquinolin-6-yl, 1-aminoisoquinolin-7-yl, 4-aminoquinazol-6-yl, 4-aminoquinazol-7-yl, 3-aminobenzisoxazol-5-yl, 3-aminobenzisoxazol-6-yl, and 3-aminoindazol-5-yl.

8. A pharmaceutical composition, comprising: a pharmaceutically acceptable carrier and a therapeutically effective amount of a compound of claim 1 or a pharmaceutically acceptable salt form thereof.

9. A pharmaceutical composition, comprising: a pharmaceutically acceptable carrier and a therapeutically effective amount of a compound of claim 2 or a pharmaceutically acceptable salt form thereof.

10. A pharmaceutical composition, comprising: a pharmaceutically acceptable carrier and a therapeutically effective amount of a compound of claim 3 or a pharmaceutically acceptable salt form thereof.

11. A pharmaceutical composition, comprising: a pharmaceutically acceptable carrier and a therapeutically effective amount of a compound of claim 4 or a pharmaceutically acceptable salt form thereof.

12. A pharmaceutical composition, comprising: a pharmaceutically acceptable carrier and a therapeutically effective amount of a compound of claim 5 or a pharmaceutically acceptable salt form thereof.

13. A pharmaceutical composition, comprising: a pharmaceutically acceptable carrier and a therapeutically effective amount of a compound of claim 6 or a pharmaceutically acceptable salt form thereof.

14. A pharmaceutical composition, comprising: a pharmaceutically acceptable carrier and a therapeutically effective amount of a compound of claim 7 or a pharmaceutically acceptable salt form thereof.

15. A method for treating a thromboembolic disorder, comprising: administering to a patient in need thereof a therapeutically effective amount of a compound of claim 1 or a pharmaceutically acceptable salt form thereof.

16. A method according to claim 15, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

17. A method according to claim 16, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

18. A method for treating a thromboembolic disorder, comprising: administering to a patient in need thereof a therapeutically effective amount of a compound of claim 2 or a pharmaceutically acceptable salt form thereof.

19. A method according to claim 18, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

20. A method according to claim 19, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

21. A method for treating a thromboembolic disorder, comprising: administering to a patient in need thereof a therapeutically effective amount of a compound of claim 3 or a pharmaceutically acceptable salt form thereof.

22. A method according to claim 21, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

23. A method according to claim 22, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (I) other procedures in which blood is exposed to an artificial surface that promotes thrombosis.

24. A method for treating a thromboembolic disorder, comprising: administering to a patient in need thereof a therapeutically effective amount of a compound of claim 4 or a pharmaceutically acceptable salt form thereof.

25. A method according to claim 24, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

26. A method according to claim 25, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

27. A method for treating a thromboembolic disorder, comprising: administering to a patient in need thereof a therapeutically effective amount of a compound of claim 5 or a pharmaceutically acceptable salt form thereof.

28. A method according to claim 27, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

29. A method according to claim 28, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

30. A method for treating a thromboembolic disorder, comprising: administering to a patient in need thereof a therapeutically effective amount of a compound of claim 6 or a pharmaceutically acceptable salt form thereof.

31. A method according to claim 30, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

32. A method according to claim 31, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

33. A method for treating a thromboembolic disorder, comprising: administering to a patient in need thereof a therapeutically effective amount of a compound of claim 7 or a pharmaceutically acceptable salt form thereof.

34. A method according to claim 33, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

35. A method according to claim 34, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

* * * * *